(12) United States Patent
Tsai

(10) Patent No.: US 8,716,355 B2
(45) Date of Patent: *May 6, 2014

(54) HYDROXYLATED TOLANS AND RELATED COMPOUNDS IN THE TREATMENT OF A CANCER

(75) Inventor: Chun-che Tsai, Kent, OH (US)

(73) Assignee: Kent State University, Kent, OH (US)

( * ) Notice: Subject to any disclaimer, the term of this patent is extended or adjusted under 35 U.S.C. 154(b) by 563 days.

This patent is subject to a terminal disclaimer.

(21) Appl. No.: 12/666,096

(22) PCT Filed: Jun. 20, 2008

(86) PCT No.: PCT/US2008/067733
§ 371 (c)(1),
(2), (4) Date: Feb. 11, 2011

(87) PCT Pub. No.: WO2008/157787
PCT Pub. Date: Dec. 24, 2008

(65) Prior Publication Data
US 2011/0130468 A1    Jun. 2, 2011

Related U.S. Application Data

(60) Provisional application No. 60/945,276, filed on Jun. 20, 2007.

(51) Int. Cl.
*A01N 31/00* (2006.01)
*A61K 31/045* (2006.01)

(52) U.S. Cl.
USPC .......................................... 514/738; 514/724

(58) Field of Classification Search
None
See application file for complete search history.

(56) References Cited

U.S. PATENT DOCUMENTS

| 6,008,260 A * | 12/1999 | Pezzuto et al. ................. 514/733 |
| 2002/0103262 A1* | 8/2002 | Docherty et al. ............. 514/733 |
| 2003/0073738 A1 | 4/2003 | Gilloteaux et al. |
| 2003/0203974 A1 | 10/2003 | Docherty et al. |
| 2005/0267175 A1 | 12/2005 | Shaw et al. |

OTHER PUBLICATIONS

Lin B. "A Novel Resveratrol Analog: Its Cell Cycle Inhibitory, Pro-Apoptotic and Anti-Inflammatory Activities on Human Tumor Cells". Diss. Abstr. Int. May 2006.*

* cited by examiner

*Primary Examiner* — Leslie A. Royds Draper
(74) *Attorney, Agent, or Firm* — Browdy and Neimark, PLLC

(57) ABSTRACT

Compounds of the hydroxytolan family kill tumor cells, inhibit tumor growth and development, and are thus useful in method for treating a tumor or cancer in subjects in need thereof. These compounds are also active in preventing or treating a variety of skin diseases and conditions. The most preferred hydroxytolan compounds are 4,4'-dihydroxytolan. (KST-201), 4 hydroxy 4' trifluoromethyltolan or 4' hydroxy 4 trifluoromethyltolan (KST-213), 3,4',5-trihydroxytolan or 3',4,5'-trihydroxytolan (KST-301) and 3,3',5,5'-tetrahydroxytolan (KST-401). The compounds and methods of using them alone and in combination with ascorbate and certain cyclic compounds to inhibit the development, growth or metastasis of tumor/cancer or preneoplastic cells, or to prevent or treat skin disorders in a subject are disclosed.

7 Claims, 10 Drawing Sheets

HYDROXYLATED TOLANS AND RELATED COMPOUNDS IN THE TREATMENT OF A CANCER

BACKGROUND OF THE INVENTION

1. Field of the Invention

The invention in the field of biochemistry and medicine relates to anti-cancer compounds of the hydroxytolan family, and methods of killing tumor cells, inhibiting tumor growth and development, and treating cancer in subjects in need thereof using these compounds alone or in combination with ascorbate and/or and certain cyclic compounds.

2. Description of the Background Art

It is believed that 554,740 Americans died from cancer in 1996. Ten years later, the National Cancer Institute estimated that 570,280 Americans would die of cancer annually. Existing cancer treatment technologies clearly are not adequate. Despite notable progress, there continues to exist a need for better drugs and therapeutic modalities to combat cancer and improve the quality and the duration of life of cancer patients. Of particular interest are orally active drugs that possesses antitumor activity either alone or in conjunction with other chemotherapeutic or anticancer agents.

More than 1 million new cases of skin cancer were diagnosed in the United States in 2006 (*Cancer Facts and Figures 2006*, American Cancer Society). About 112,000 of these new cases were melanoma of which about 44% cases were non-invasive and about 56% were invasive. The latter were distributed as ~55% in men and ~45% women. Human melanoma, a potentially preventable malignancy, is the most serious skin cancer and is among the most drug resistant of all malignancies (Yang, S et al., 2005, *Mol. Cancer. Ther.* 4: 1923-35). Excluding basal cell and squamous cell carcinomas, which together are the most common cancers in both sexes, these figures make invasive melanoma the fifth most common cancer in men and the seventh most common cancer in women. Furthermore, 7,910 Americans (~63% men and ~37% women) died of melanoma in 2006, representing one death every 67 minutes). Additional figures indicate that the incidence of melanoma has increased 690% from 1950 to 2001, while the overall mortality rate increased only 165% during this same period (The Lewin Group, Inc., *The Burden of Skin Diseases*, 2004; Soc. for Invest. Dermatol. and Amer. Acad. Dermatol., pp. 1-110). After breast cancer in premenopausal women (ages 30-34 years), melanoma has exhibited the fastest rate of increase in incidence in the United States, while rates for many other cancers are falling (Demierre, M.-F et al. 2003, *J. Clin. Oncol.* 21: 158-65). The lack of efficacy of current treatment protocols points to the need for the development of effective modalities for treating or preventing melanoma.

Uncontrolled imbalance between cell proliferation and cell differentiation or cell death may result in the development of malignant or cancerous clones of cells which are commonly less differentiated than their normal counterparts. Thus, promising targets for cancer intervention are induction of (i) differentiation of pre-malignant or malignant cells into more normal cells and (ii) tumor-specific cell death during the process of carcinogenesis or tumor development. Compounds which induce differentiation or cell death are candidates for cancer chemoprevention and/or chemotherapy (Hong W K and Sporn M B, *Science,* 1997, 278:1073-7; Suh N et al., *Anticancer Res.,* 1995, 15:233-9; Fimognari C et al., *Biochem Pharmacol.,* 2004, 68:1133-8).

In the last several years, hundreds of plant extracts have been evaluated for their potential as cancer chemopreventive agents and for their ability to induce cell death (Clement M V et al., *Blood,* 1998, 92:996-1002; Cooke D et al., *Eur J Canc.,* 2005, 41:1931-40). Because inflammation and reactive oxygen species (ROS) can be major determinants in the development of many diseases, including cancer, as well as in viral replication, plant polyphenols have been evaluated as chemopreventive agents because of their antioxidant, oxygen radical scavenging and anti-inflammatory activities.

Many of these compounds inhibit the cellular events associated with all 3 stages of carcinogenesis (initiation, promotion and progression). One strategy has employed phenolic compounds to counteract cancer formation by blocking one or several steps in this multistage process. A non-flavonoid polyphenol of the stilbene group, resveratrol (3,5,4'-trihydroxy-trans-stilbene, depicted below), is a typical example of such a compound. Resveratrol consists of two aromatic rings linked by an ethylene bridge with two hydroxyl groups at the 3 and 5 positions of one ring and one hydroxyl group at the 4' position of the other ring.

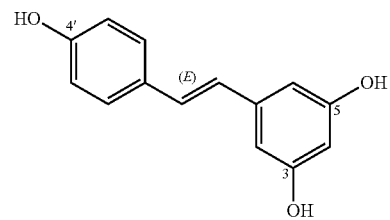

Resveratrol

Resveratrol occurs in a trans and a cis configuration, and as a glucoside. The trans isomer is most active while the cis-isomer is almost inactive in may types of biological and biochemical tests. Its diverse bioactivities include antioxidant action, modulation of lipid and lipoprotein metabolism, inhibition of platelet aggregation, vasorelaxing activity, anticancer activity and estrogenic activity (Aggarwal B B et al., *Anticancer Res.,* 2004, 24:2783-40; Fremont L., *Life Sci.,* 2000, 66:663-73). Resveratrol thus may act on cancer cells by promoting cell death, activating phase II detoxification and attenuating cell proliferation, DNA synthesis and inflammation (Aggarwal et al., supra; Aziz M H et al., *Int J Oncol.,* 2003 23:17-28; Dong Z., *Mutat Res.,* 2003, 523-524:145-50; Fremont L., supra; Gusman J et al., *Carcinogenesis,* 2001, 22:1111-7; Jang M et al., *Science,* 1997, 275:218-20; Savouret J F et al., *Biomed Pharmacother.,* 2002, 56:84-7; Signorelli P et al., *J Nutr Biochem.,* 2005, 16:449-66). The trans isomer of resveratrol blocks all 3 stages of carcinogenesis noted above.

Resveratrol was reported to inhibit cell proliferation and cause apoptotic cell death by modulating numerous mediators of cell cycle and survival signaling. Depending on concentrations, resveratrol "switched" cells between reversible cell cycle arrest and irreversible apoptosis. Specifically, resveratrol treatment blocked the cell cycle in the $G_0/G_1$, $G_1/S$ transition, S phase or $G_2/M$ phases by (a) suppressing cyclins and their corresponding kinases, (b) increasing p53 levels or (c) inhibiting DNA synthesis. Resveratrol also up-regulated pro-apoptotic members of the Bcl-2 family and down-regulated anti-apoptotic members of this family. Finally, resveratrol inhibits NF-κB and AP-1 signaling pathways, their upstream kinases and their downstream targets (including inducible cyclooxygenase-2, inducible nitric oxide synthase and matrix metalloprotease-9. Thus, resveratrol can inhibit proliferation and induce cell death.

Resveratrol is considered to be a phytoestrogen because of its structural homology to the estrogens, and its ability to compete with estrogens for binding to estrogen receptors and to activate receptor-mediated gene transcription. However, resveratrol also manifests anti-estrogen function and can inhibit hormone-induced carcinogenesis with agonistic or antagonistic hormonal activity depending on the intake concentration, tissue-specific expression of estrogen receptors, cofactors present for DNA binding and different gene promoters (Aggarwal et al., supra; Fremont, supra). Likewise, resveratrol represses transcription or translation of different classes of androgen up-regulated genes via a reduction in androgen receptor (AR) content (Mitchell S H et al., *Canc Res*, 1999, 59:5892-5).

While the antitumor mechanisms of resveratrol are pleiotropic, and it appears to be a promising antitumor agent in part because it affects the 3 stages of carcinogenesis, its use has been hampered by its relatively low aqueous solubility and its apparent lack of selectivity or specificity for tumor cells. Resveratrol is also significantly toxic to normal cells (Aggarwal et al., supra). The present invention is directed primarily to a distinct class of diphenol compounds, the tolans, and their advantageous properties as anti-cancer agents when compared to resveratrol.

A number of stilbenes that are tubulin-binding agents, e.g., combretastatin AI, combretastatin A4 (Chaplin, D J et al., *Brit J. Canc* 27, S86-88 (1996)) and combretastatin A4 phosphate (Chaplin, D J et al., *Anticancer Res* 19(1A), 189-96, (1999)) selectively damage neovasculature of solid tumors in animal models. Other analogues of combretastatin A4 show activity in assays of cytotoxicity in vitro and in animal tumour models. See, for example Cushman, M et al., 1991, *J. Med. Chem.* 34:2579-88; Ohsumi, K. et al., 1998, *J. Med. Chem.* 41:3022-32; Hatanaka T et al., 1998, *Bioorg Med Chem. Lett.* 8:3371-4; Woods, J A et al. 1995, *Brit. J. Canc* 71:705-11). However, it is not apparent whether such compounds act through direct effects on tumor tissue or on by selective anti-vascular mechanisms. International Patent Pub. WO 01/12579 discloses a series of cis-stilbenes with vascular damaging activity, particularly targeting newly-formed vascular endothelium, especially that associated with solid tumors. Such compounds were said to be useful in the prophylaxis and treatment of cancer (sold tumors) and in other diseases associated with undesired neovascularization such as diabetic retinopathy, psoriasis, rheumatoid arthritis, macular degeneration and the formation of atherosclerotic plaque.

U.S. Pat. Nos. 6,599,945 and 7,094,809 (co-invented by the present inventor) disclose several hydroxytolan compounds and their use in inhibiting the formation of infectious herpes virus particles or for treating gonorrhea caused by *Neisseria gonorrhoeae*. However the potential utility of these, or any other hydroxytolans as anti-cancer agents was unknown until the making of the present invention. U.S. Pat. Nos. 6,197,834 and 6,355,692 disclose certain hydroxylated stilbenes, and specifically resveratrol, for similar uses. The use of resveratrol in suppressing or treating cancer is also disclosed in U.S. Pat. No. 6,008,260. None of these references directed to resveratrol disclose the hydroxytolans of the present invention nor suggest the notion of their use as anti-cancer agents.

Vitamin C/Ascorbate

The chemical structure of Vitamin C (sodium ascorbate) is shown below:

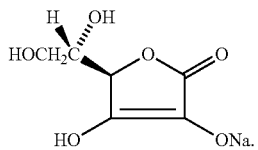

Vitamin C (abbreviated herein as "VitC" or "VC") acts as a pro-oxidant, and has been evaluated as an antitumor agent. Several in vitro studies demonstrated that VC selectively accumulated in, and was toxic to, a variety of human tumor cells in culture. These included malignant melanoma cells, leukemia cells, neuroblastoma cells, ascites tumor cells as well as acute lymphoblastic leukemia, epidermoid carcinoma and fibrosarcoma cells.

Several case reports describe favorable outcomes in cancer patients undergoing high dose intravenous VC therapy. E. Cameron and L. Pauling (*Proc Natl Acad Sci USA* 73:3685-9, 1976) reported the effect of administering supplemental ascorbate (10 g/day intravenously (i.v.) for 10 days followed by 10 g/day orally thereafter) to 100 terminal cancer patients as part of routine management of these patients. The "controls," 1000 subjects matched for age and sex, were left untreated. These were individuals who suffered from cancer of the same primary organ type and histological type as the patient group. The mean survival time (MST) for ascorbate-treated subjects (>210 days) was more than 4.2 times greater than that of the controls (50 days) ($p<<0.0001$). Six of the 100 treated subjects had ovarian cancer. When their progress was compared to that of disease-matched controls, the MST of 148 days was twice as long as the controls (MST: 71 days; $p<0.005$). The results suggested that VC may be of value in the treatment of advanced ovarian cancer. Two later randomized, double-blind, placebo-controlled, clinical trials (Creagen et al., *New Eng. J. Med.* 301:687-690, 1979; Moertel et al., *New Eng. J. Med.* 312:137-141, 1985) that were designed to evaluate the effectiveness of 10 g of oral VC in patients with advanced cancer, reported no benefits of oral VC treatment. More recently, these studies have been criticized (Riordan et al., *Med. Hypotheses* 44:207-213, 1995) because the oral VC dose of 10 g/day is not believed to be sufficient to achieve plasma concentrations that were found to be cytotoxic for tumor cells in culture. Finally, a number of case studies (Riordan et al., supra; Riordan et al., *P.R. Health Sci. J.* 23:115-118, 2004; Drisko et al., *J. Am. Coll. Nutr.* 22:118-23, 2003) reported the effects of high i.v. doses of VC in patients with breast, colorectal, ovarian, pancreatic, renal cell carcinoma. VC doses ranged from 10 to 100 g given twice per week with the majority of doses being 60-70 g per infusion. The results of these case reports suggested that high i.v. doses of VC do not interfere with conventional anticancer therapy; are generally not toxic to cancer patients with normal renal function; and induce a small number of complete remissions. This high dose i.v. regimen of VC administration, while manifesting antitumor activity, is financially burdened an inconvenient as it requires additional doctor visits.

VC usage in humans is well-documented, and the vitamin is well tolerated in animals. Mice given daily VC doses of 6.5 g/Kg body weight for 6 weeks and 2 g/Kg for 2 years showed no abnormal rates of mortality, weight changes, blood chemistry, hematology, histology, or other pathologies (Klenner, F R, 1951, *South Med J* 113:101-7). This reference includes a table of therapeutic doses ranging from 35 g/day for a 220 pound man to 1.2 g/day in infants. Also indicated were maintenance doses of 60 mg/kg/day (i.e., about 2180 mg/day) and 75 mg/day for these respective groups. The only systemic toxicity noted at these doses has been diarrhea/gastrointestinal upset, in which case the doses are injected, bypassing these complications.

NF-κB (Nuclear Factor-Kappa B)

NF-κB is a protein complex transcription factor. NF-κB and its inhibitor IκB form an inactive complex in the cytoplasm. Activation occurs by phosphorylation, ubiquitination and degradation of IκB, which then releases active NF-κB into the nucleus where it regulates the expression of target genes leading to a variety of cellular effects. Constitutively active NF-κB activates expression of genes that keep cells proliferating and protect them from conditions that would otherwise induce death.

Dysregulation of NF-κB has been linked to cancer. In tumor cells, NF-κB is active either due to mutations in genes encoding the NF-κB transcription factors themselves or in genes that control NF-κB activity (such as IκB genes). Some tumor cells secrete factors that activate NF-κB. Blocking NF-κB can stop tumor cell proliferation, induce cell death or increase the cells' sensitivity to the action of antitumor agents. Thus, NF-κB is a subject of active research as a target for anti-cancer therapy. As noted, The NF-κB family members play multiple roles in the regulation of immune and inflammatory responses, developmental processes in addition to cancer.

U.S. Pat. No. 6,410,516 (Jun. 25, 2002) to Baltimore et al. discloses—constitutive and tissue-specific protein factors that bind to transcriptional regulatory elements of Immunoglobulin (Ig_genes (promoter and enhancer). NF-κB, the gene encoding NF-kB, IκB and the gene encoding IκB are useful for enhancing transcription of Ig genes. Recent work by the laboratories of Karin, Ben-Neriah and others has highlighted the importance of NF-κB in inflammation as well as cancer, and has underscored the value of therapies that regulate NF-κB activity (Pikarsky E, Ben-Neriah Y., *Eur J Cancer.* 2006 42:779-84. Häcker H, Karin M., Sci STKE. 2006 Oct. 17; Karin M., *Nature.* 2006, 441:431-6; Karin M., *Mol. Carcinog.* 2006 45:355-61; Luo J L et al., *J Clin Immunol.* 2005, 25:541-50; Luo J L et al., *J Clin Invest.* 2005 115:2625-32; Karin M, Greten F R., *Nat Rev Immunol.* 2005; 5:749-59; Greten F R, Karin M. *Cancer Lett.* 2004; 206:193-9; Karin M et al., Nat Rev Drug Discov. 2004, 3:17-26; Lin A, Karin M., Semin Cancer Biol. 2003, 13:107-14; Amit S, Ben-Neriah Y. Semin Cancer Biol. 2003, 13:15-28; Karin M et al., Nat Rev Cancer. 2002; 2:301-10; Karin M, Lin A. Nat. Immunol. 2002, 3:221-7).

The discovery that activation of NF-κB nuclear translocation can be separated from the elevation of oxidant stress provides a basis for developing strategies for NF-κB inhibition. NF-κB has been shown as the only biomarker that can predict a risk of progression or recurrence of prostate cancer. US Patent Pub. 20050026196 discloses NF-κB as a prognostic marker for prostate cancer and for predicting risk of progression or recurrence by measuring the proportion of NF-κB localized in the nuclei of a tumor sample compared to total NF-κB in the tumor sample. Drugs which inhibit NF-κB within tumor cells are believed to be potentially useful anti-cancer therapeutics.

As noted above, resveratrol is widely recognized to have anti-cancer activity that also inhibits NF-κB. The present inventor discovered new compounds that may be considered resveratrol analogs; their actions on NF-κB activity are disclosed herein.

None of the documents cited above disclose or suggest the specific pharmaceutical compositions, methods and uses of the compounds that are disclosed and claimed herein. To the extent that any specific disclosure in these publications or other publications may be considered to anticipate any generic aspect of the present invention, the disclosure of the present invention should be understood to include a proviso or provisos that exclude any such species that were previously disclosed. The aspects of the present invention which are not anticipated by the disclosure of said publications are also unobvious from the disclosure of these publications, due at least in part to the unexpectedly superior results disclosed or alleged herein. One advantage of the present invention is that the hydroxytolan or other polyphenolic described herein acting in concert with Vitamin C or other ascorbates, including salts, with or without a cyclic compound described below, provides an improved anti-cancer composition or improved method for combination anti-cancer therapy.

Citation of the above documents is not intended as an admission that any of the foregoing is pertinent prior art. All statements as to the date or representation as to the contents of these documents is based on the information available to the applicant and does not constitute any admission as to the correctness of the dates or contents of these documents.

SUMMARY OF THE INVENTION

The present invention is directed to a composition useful for killing or inhibiting the growth of tumor or cancer cells and/or inhibiting tumor angiogenesis and for treating cancer in a subject in need thereof, which composition comprises a compound of formula I:

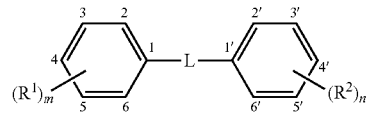

Formula I wherein:

L represents a linkage between the two phenyl rings selected from a —C≡C— acetylene linkage, a —C=C— ethylene linkage or a —C—C— ethane linkage $R^1$ and $R^2$ are, independently substituents at any available position of the phenyl rings;

m and n are, independently, 0, 1, 2, 3, 4 or 5 representing the number of $R^1$ and $R^2$ substituents of the rings, respectively, and at least one of m or n must be ≥1;

wherein $R^1$ and/or $R^2$ is:

—OH, a halogen, a haloalkyl group with one C atom substituted with from 1 to 3 halogen atoms, a $C_1$-$C_6$ alkyl, $C_2$-$C_6$ alkenyl, or $C_2$-$C_6$ alkynyl group, —$OR^3$, wherein $R^3$ is a $C_1$-$C_6$ alkyl, $C_2$-$C_6$ alkenyl, or $C_2$-$C_6$ alkynyl group; and wherein at least one occurrence of $R^1$ or $R^2$ is —OH, with the following provisos:

(a) when L is —C≡C—, the compound of Formula I is a trans-stilbene and is not resveratrol;

(b) when L is —C≡C—, the compound is not KST-201, KST-213, KST-301 or KST-401 (which compounds are defined below); and (c) when L is —C—C—, the compound is not a 1-(2,6-dichloro-4-hydroxyphenyl)-2-phenylethane.

Most preferably in the above composition, L is —C≡C—.

The trans stereoisomer of the above compounds is preferred to the cis isomer.

Another preferred composition comprises one or more hydroxylated tolans, and one or more hydroxylated stilbenes and/or one or more hydroxylated diphenylethanes in accordance with Formula I and the above structural specifications.

Also provide herein is a pharmaceutical composition that comprises a composition as described above comprising one or more of the active compounds described and a pharmaceutically acceptable carrier or excipient. The pharmaceutical composition may be formulated so that one or more of the components, e.g., the compound of Formula I, the ascorbate or VC, or the cyclic, compound (Hc/OH), preferably heterocyclic compound, is formulated for parenteral, oral or topical administration.

The present invention provides a method of inhibiting the development, growth or metastasis of tumor or cancer cells or cells of a precancerous lesion, in a subject, administering to a subject in need thereof, an effective growth-inhibiting or metastasis-inhibiting amount of one or more of a first compound of Formula I. (By "first compound" is intended one of a possible series of compounds that may be given with "a second compound" which generally refers to compounds of a different class; see below.)

Formula I

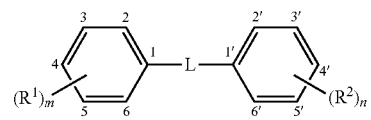

wherein:

L represents a linkage between the two phenyl rings selected from a —C≡C— acetylene linkage, a —C═C— ethylene linkage or a —C—C— ethane linkage $R^1$ and $R^2$ are, independently substituents at any available position of the phenyl rings;

m and n are, independently, 0, 1, 2, 3, 4 or 5 representing the number of $R^1$ and $R^2$ substituents of the rings, respectively, and at least one of m or n must be ≥1;

wherein $R^1$ and/or $R^2$ is:
—OH,
a halogen,
a haloalkyl group with one C atom substituted with from 1 to 3 halogen atoms,
a $C_1$-$C_6$ alkyl, $C_2$-$C_6$ alkenyl, or $C_2$-$C_6$ alkynyl group,
—$OR^3$, wherein $R^3$ is a $C_1$-$C_6$ alkyl, $C_2$-$C_6$ alkenyl, or $C_2$-$C_6$ alkynyl group; and
wherein at least one occurrence of $R^1$ or $R^2$ is —OH,
with the proviso that when L is —C═C—, the compound of Formula I is a cis-stilbene and is not resveratrol, and when L is —C—C—, the compound is not a 1-(2,6-dichloro-4-hydroxyphenyl)-2-phenylethane.

In one preferred embodiment of the above method, the compound is a trans stereoisomer.

In a preferred embodiment of the above method, L is —C≡C— in Formula I. Preferred among these are hydroxytolans. Particular preferred hydroxytolans are KST-201, the structural formula of which is Formula II

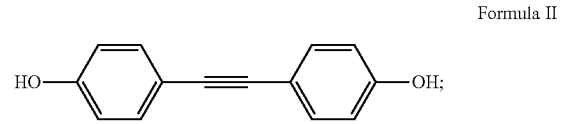

KST-213, the structural formula of which is

Formula III

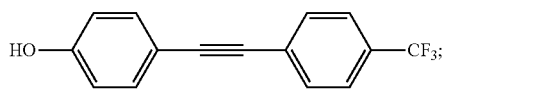

KST-301), the structural formula of which is:

Formula IV

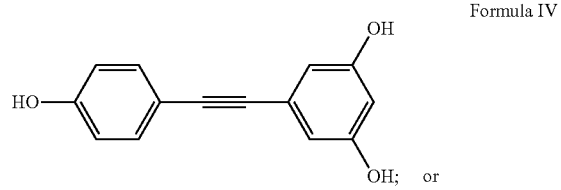 [SMILES: Oc1ccc(C#Cc2cc(O)cc(O)c2)cc1]

KST-401, the structural formula of which is

Formula V

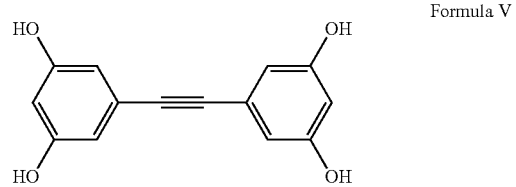 [SMILES: Oc1cc(O)cc(C#Cc2cc(O)cc(O)c2)c1]

A list of the alternate names used herein of certain preferred hydroxytolan compounds.

| Inventor's Internal Designation | From SAR Tables | Chemical name |
|---|---|---|
| KST-201* | Tolan-2 | 4,4'-dihydroxytolan |
| KST-301 | Tolan-3 | 3,4',5-trihydroxytolan or 3',4,5'-trihydroxytolan |
| KST-401 | Tolan-4 | 3,3',5,5'-tetrahydroxytolan |
| KST-213 | Tolan-11 | 4-hydroxy-4'-trifluromethyltolan or 4'-hydroxy-4-trifluromethyltolan |

*in some uses of this designation, the hyphen may be omitted or replaced by a space In the above method, the administering preferably results in killing of primary or metastatic tumor or cancer cells.

In the above method, the composition is preferably administered orally, intravenously, intraperitoneally, topically, intrathecally, intramuscularly, subcutaneously, transdermally, intranasally or rectally.

The present invention also provides a method of inhibiting the development, growth or metastasis of tumor or cancer cells, or cells of a precancerous lesion, in a subject, comprising administering to the subject in need thereof, a combination that comprises (a) an effective amount of a first compound, that is a compound of Formula I as described above, preferably one in which L is —C≡C—, more preferably a compound selected from KST-201, KST-213, KST-301 and KST-401, as described.

(b) an amount of a second compound which is effective in combination with the first compound to kill, or inhibit the growth of the cells, wherein the second compound is
  (i) sodium ascorbate (VC), which may be in bisulfite form; or
  (ii) a cyclic compound with a keto or hydroxyl group in a ring system.

The genus of such cyclic compounds is abbreviate herein "Hc/OH"

As an alternative embodiment to use of a single "second compound" as above, the compound of Formula I is combined with both an effective amount of VC as the second compound, and an effective amount of a third compound that is the Hc/OH compound.

When the second compound is VC, the first compound and VC are administered in a preferred ratio of the VC to the first compound of between about 50 and about 900. More preferably, the ratio is between about 100 and about 600.

When the second compound is the Hc/OH compound, the first compound and the Hc/OH are administered in a ratio of the third compound to the first compound of between about 50 and about 900. More preferably, the ratio is between about 100 and about 600.

In the above method that includes use of both VC and an Hc/OH, the ratio of the VC to the Hc/OH is preferably in the range of between about 50:1 and about 500:1, preferably between about 100:1 and about 300:1

The amount of the VC administered orally to the subject per day is preferably between about 15 mg and 1 g per kg body weight, and the amount of the Hc/OH administered per day is preferably between about 30 μg and about 20 mg per kg body weight.

In another embodiment, a subject is (a) pretreated with the above "second compound" (whether VC or the Hc/OH compound), followed by (b) treatment with the first compound, preferably the hydroxylated tolan, or a combination of the first compound and VC with or without the Hc/OH compound.

As noted, the invention is directed to the above method which comprises administering to the subject the first compound and the combination of the second and the third compound, wherein the presence of the Hc/OH compound increases the killing or growth inhibition by a statistically significant amount, at least about 10% over that produced by administration of the combination of the first compound and VC, or alternatively, VC increases the killing or growth inhibition by a statistically significant amount, at least about 10% over that produced by administration of the combination of the first compound and the Hc/OH compound.

The increases in killing or growth inhibition, indicated as 10% above, is preferably greater, for example, at least about 20%, preferably at least about 30%, more preferably at least about 40%, or at least about 50%, or at least about 60%, or at least about 70%, or at least about 80%, or at least about 90% or at least about 100%. All intermediate values in the above ranges are also contemplated.

In the above method, the administering of the combination of compounds results in killing of primary or metastatic tumor/cancer cells or cells of a precancerous lesion.

Using "HT" in this sentence to refer to a hydroxylated tolan or any Formula I compound, the combinations of compounds that are useful in the present pharmaceutical compositions and treatment methods include: {HT+VC}, {VC+Hc/OH}, {HT+VC+Hc/OH}.

In the foregoing method of administering the first, the second and, optionally, the third compound, the first compound, the second compound and, if present, the third compound, may be administered by the same or by different routes, which route are preferably oral, intravenous, intraperitoneal, topical, intrathecal, intramuscular, subcutaneous, transdermal, rectal, and intranasal.

In the above method, the administering is preferably oral, intravenous or intraperitoneal. As a result of administering the compound of Formula I or any of the above combination of compounds, as described above, the cells being killed or the tumor being treated include both solid tumors or cancers, and hematological malignancies:

Preferably, cells being killed or inhibited are, for example, breast cancer cells, colon cancer cells, prostate cancer cells, lymphoma cells, leukemia cells, lung cancer cells, head or neck cancer cells, brain tumor cells, ovarian cancer cells, liver cancer cells, neuroblastoma cells, medulloblastoma cells, squamous cell carcinoma cells, carcinoma in situ cells or basal cell carcinoma cells. The cells being killed or inhibited may be cancer cells that developed from an identifiable or recognized precancerous lesion or they may be cells of the precancerous lesion, for example actinic keratosis. Treatment that results in the killing or inhibition of these precancerous cells will treat the actinic keratosis and/or inhibit the development of squamous cell carcinoma from the actinic keratosis.

Preferably, the tumor or cancer being treated in the subject is, accordingly, breast cancer, colon cancer, prostate cancer, lymphoma, leukemia, lung cancer, head or neck cancer, a brain tumor, ovarian cancer, liver cancer, neuroblastoma, medulloblastoma, squamous cell carcinoma, carcinoma in situ or basal cell carcinoma.

The method is expected to result in:
(1) a partial response, characterized as at least a 50% decrease in the sum of the products of maximal perpendicular diameters of all measurable tumor lesions without evidence of new lesions or progression of any preexisting lesions, or
(2) a complete response characterized as the disappearance of all evidence of the cancer or tumor for at least one month.

Also provided is a method of inhibiting tumor angiogenesis in a subject which comprises administering to a subject in need thereof an angiogenesis-inhibiting effective amount of a compound of Formula I, as set forth above, wherein L, the R groups, and m and n are also as set forth above. Preferably in L is —C≡C—. The preferred compounds for the above anti-angiogenic method are KST-201, KST-213, KST-301 and KST-401. In this method the administering is preferably by a route selected from the group consisting of oral, intravenous, intraperitoneal, topical, intrathecal, intramuscular, subcutaneous, transdermal, rectal, and intranasal. As above, the tumor cells are from a subject bearing, (i) a solid tumor or cancer or (ii) a hematological malignancy, with preferred tumor types as described above. Also, all the combinations of compounds described above are intended in such anti-angiogenic methods.

In one embodiment of the above method, the subject is administered as a first compound, one or more hydroxytolan compounds of Formula I, another compound that is a hydroxystilbene (L is a —C=C— linkage in Formula I) or a diphenyl ethane compound (L is a —C—C— linkage in Formula I. The additional compound may be administered by the same route or a different route as the hydroxytolan compound or compounds. In one embodiment, the genus of compounds included in the method excludes resveratrol.

Also provide is a method of inhibiting the development, growth or metastasis of tumor or cancer cells, in a subject, or inhibiting tumor angiogenesis in a subject, comprising administering to the subject in need thereof, an effective growth-inhibiting, metastasis-inhibiting or angiogenesis-inhibiting amount of (i) a hydroxylated tolan, (ii) a hydroxylated stilbene, (iii) a hydroxylated diphenyl ethane in accordance with Formula I, or (iv) any combination of (i)-(iii). In a specific embodiment, the above method excludes resveratrol as a compound to be administered.

One embodiment of the present invention is a topical pharmaceutical composition comprising a compound of the present invention, as described above, including a pharmacologically acceptable salt, ester, amide, prodrug or analogue of the disclosed compound, and a combination of any of the foregoing. More preferably, the compound is a hydroxylated tolan, such as one or more of KST-201, KST-213, KST-301 or KST-401. However, as discussed in detail elsewhere herein, those skilled in the art will appreciate that other compounds of Formula I may also be used. Such a composition is used in a method to preventing and/or treat (including alleviation of symptoms) a skin condition, disorder or disease that includes, but not limited to, a form of skin cancer. This method comprises administering to a susceptible or affected subject, preferably by application to the skin, the above topical pharmaceutical composition that comprises a therapeutically effective amount of an active compound as described herein. The skin conditions, disorders or diseases treatable in accordance with this invention include, without limitation, psoriasis, contact dermatitis (irritant-induced or allergic), atopic dermatitis (allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, undesired skin changes resulting from natural aging and the like.

The present invention is also directed to methods of treating cells infected with a virus, such as HSV-1, with the compositions disclosed herein to limit the size of lesions, promote healing, and inhibit viral production and spread.

The present invention also provides uses of the compounds disclosed herein in the preparation of a pharmaceutical composition or manufacture of a medicament for inhibiting the development, growth or metastasis of tumor or cancer cells, or cells of a precancerous lesion, in a subject (or for any other uses disclosed herein.) Also included is a use of manufacture of medicament for treating cells infected with a virus to limit the size of lesions, promote healing, and inhibit viral production or spread.

DESCRIPTION OF THE PREFERRED EMBODIMENTS

Figure 1:
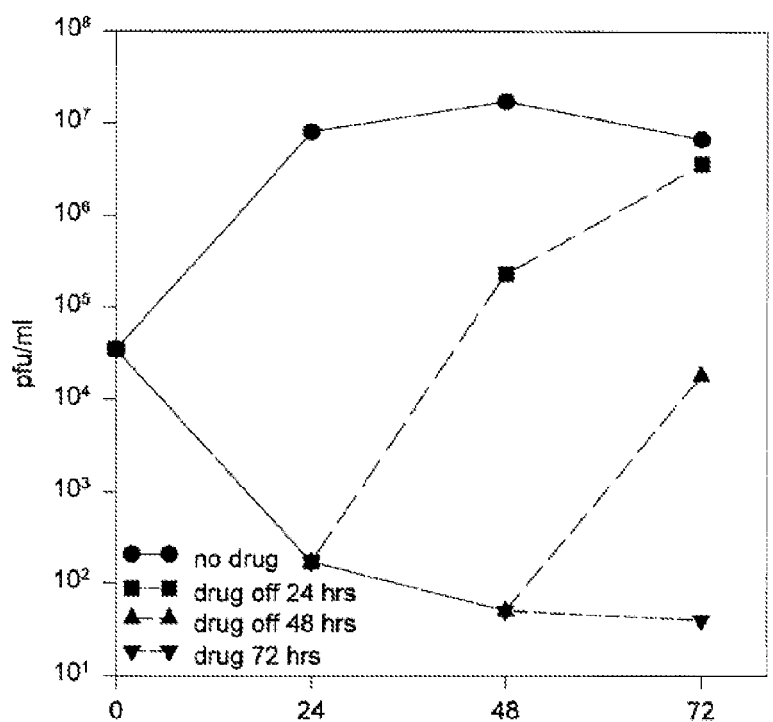
FIG. 1. Reversibility of KST-301/Tolan-3 Inhibition of HSV-1. HSV-1 infected Vero cells were treated with 350 µM Tolan-3 for 24 h. Subsequently, the compound was removed and replaced with culture medium alone, and the incubated continued for 48 or 72 hrs. In a second experiment, HSV-1 infected Vero cells were incubated with 350 µM Tolan-3 for 48 h. Thereafter, the Tolan-3 was removed and replaced by medium and the incubation continued for an additional 24 h. Viral titers were calculated by a standard plaque assay.

The present inventor has discovered that certain compounds not heretofore known to have anti-cancer activity are useful in slowing the killing of cancer cells in vitro and in vivo and slowing the progression of tumor growth or metastasis. The inventor made the surprising discovery that modifying polyphenolic compounds by altering the number and/or position of the hydroxyl groups on the rings, and/or changing the chemical structure of the linkage between the aromatic rings, in particular to a —C≡C— acetylene linkage (i.e., tolans) results in compounds which kill cancer cells more rapidly and effectively while maintaining low toxicity to normal cells.

The present invention provides novel compounds and pharmaceutical compositions thereof which inhibit cancer cell growth and induce cancer cell death as well as methods of using such compositions to treat any of a number of forms of cancer, including bladder, prostate and ovarian cancer.

As disclosed herein, a series of novel phenolic compounds (tolans) have been evaluated for their antitumor activity against a battery of human tumor cell lines and normal human fibroblasts. These novel phenolic compounds preferentially kill cancer cells faster and at lower doses than does resveratrol (as described above).

The compound resveratrol is depicted above. Studies of structure-activity relationships (SAR) of resveratrol and its analogs revealed the functional groups and chemical structures essential to their bioactivities. Employing such an intelligent design approach, the present inventor found that certain "modifications" of resveratrol yielded some of the novel compounds with unexpected properties as disclosed herein. Such modifications of the two aromatic rings included:

(1) alteration of the number and/or position of the hydroxyl groups on either ring.
(2) replacement of the hydroxyl groups on either ring with other substituents.

Most importantly, changing the linkage between the two aromatic rings led to the design of a novel series of tolan compounds, most preferably hydroxytolans. These, including hydroxytolans produced and tested in U.S. Pat. Nos. 6,599,945 and 7,094,809 were found to have anti-cancer activity with an improved side effect profile compared to resveratrol.

As discussed in more detail below, the present invention provides a method of affecting cancer cells in a desirable manner and thereby treating cancer using one or more members of the hydroxytolan series described herein. The compounds may be administered orally, intravenously, intraparatoneally or intranasally (among other routes) to kill or inhibit the growth or metastasis of malignant neoplastic cells (i.e., cancer cells). These compounds exhibit specific antitumor activity against human bladder, ovarian and prostate tumor cells, as exemplified herein.

While the inventor does not wish to be bound by any mechanistic explanation of these effects or outcomes, nor must they be, it is believed that antitumor activity is related to redox cycling and the possible generation of peroxides and other reactive oxygen species (ROS) as well as the inhibition of tyrosine kinases and subsequent membrane lipid alterations, and DNA destruction in cancer cells which tend to be catalase-deficient.

Hydroxylated Tolans

The structural skeleton of the preferred compounds of the present invention, the hydroxylated tolans, comprises two aromatic rings joined by an acetylene bridge. The compounds preferred for the methods and uses of the present invention are described by Formula I,

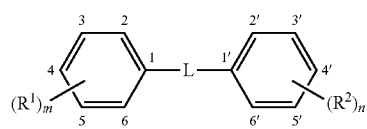

Formula I wherein:

L represents a linkage between the two phenyl rings and is preferably a —C≡C— acetylene linkage (tolans), though it may be a —C=C— ethylene linkage (stilbenes) or a —C—C— ethane linkage (diphenyl ethane derivatives).

$R^1$ and $R^2$ are substituents at any available ring position;

m and n is the integer 0, 1, 2, 3, 4 or 5 representing the number of aromatic ring $R^1$ and $R^2$ substituents, respectively.

Preferred, though non-limiting examples of phenyl ring substituents $R^1$ and $R^2$ are:

(i) OH,
(ii) a halogen,
(iii) a haloalkyl group wherein one C atom is substituted with from 1 to 3 halogens; the halogen is preferably F, Cl and Br, most preferably F, so that most preferred haloalkyl substituents are $CH_2F$, $CHF_2$ and $CF_3$;
(iv) a $C_1$-$C_6$ alkyl (referred to also as "lower alkyl"), $C_2$-$C_6$ alkenyl ("lower alkenyl"), or $C_2$-$C_6$ alkynyl ("lower alkynyl")
(v) $OR^3$, wherein $R^3$ is a lower alkyl, lower alkenyl, or lower alkynyl.

When m or n is 2 or greater, the $R^1$ and $R^2$ substituents may be the same or different. For example, if m=2, the ring may be disubstituted with one —OH group and one haloalkyl group, etc.

When L is —C≡C—, at least one of $R^1$ or $R^2$ is OH (and m or n is 1).

The present invention includes methods of using similar substituents of stilbenes (where L is —C=C— in Formula I) and diphenylethanes (where L is —C—C— in Formula I). In these embodiments, at least one of $R^1$ or $R^2$ is OH (and m or n is 1) so that the class of intended compounds for use as anticancer agents are hydroxystilbenes and hydroxyphenyl ethanes. These may be combined with hydroxytolans in the present compositions and such combinations used to inhibit cancer cells or treat cancer.

The most preferred compounds for use in the present methods, the chemical moieties of which were disclosed in U.S. Pat. Nos. 6,599,945 and 7,094,809, are shown below, and written in terms of the features of Formula I. Each is a hydroxylated tolan in which L is a —C≡C— linkage:

(A) KST-201, shown below in Formula II:
m=1 and n=1 (in Formula I);
$R^1$ is an OH group at ring position 4;
$R^2$ is an OH group at ring position 4';

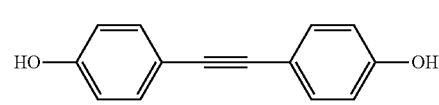

Formula II

A chemical name for this compound is 4,4'-dihydroxytolan.

(B) KST-213, shown below in Formula III:
m=1 and n=1 (in Formula I);
R¹ is an OH group at position 4 and R² is a CF₃ at position 4', or alternatively
R¹ is a CF₃ at position 4 and R² is an OH at position 4'.

Formula III

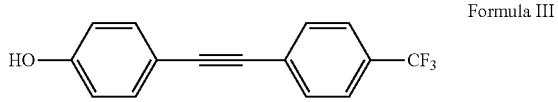 [SMILES: Oc1ccc(C#Cc2ccc(C(F)(F)F)cc2)cc1]

Chemical names for this compound are 4-hydroxy-4'-trifluoromethyltolan and 4'-hydroxy-4-trifluoromethyltolan.

(C) KST-301, shown below in Formula IV:
m=2 and n=1 (in Formula I);
R¹ is an OH group at positions 3 and 5 and R² is an OH group at position 4' or, alternatively,
m=1 and n=2, and
R¹ is an OH group at position 4 and R² represents OH groups at positions 3' and 5'.

Formula IV

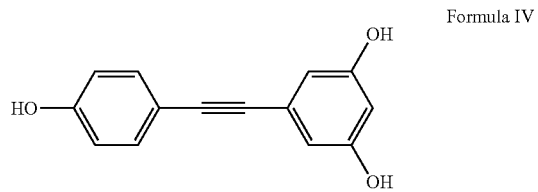 [SMILES: Oc1ccc(C#Cc2cc(O)cc(O)c2)cc1]

Chemical names for this compound are 3,4',5-trihydroxytolan and 3',4,5'-trihydroxytolan.

(D) KST-401, shown below in Formula V:
m=2 and n=2 (in Formula I);
R¹ represents OH groups at positions 3 and 5 and R² represents OH groups at positions 3' and 5'

Formula V

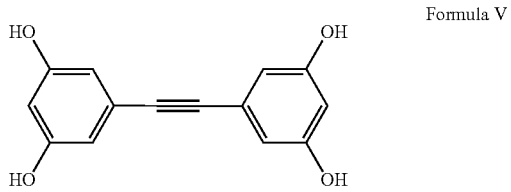 [SMILES: Oc1cc(O)cc(C#Cc2cc(O)cc(O)c2)c1]

A chemical name for this compound is 3,3',5,5'-tetrahydroxytolan.

Other compounds included within the scope of the present methods and uses are compounds of Formula I wherein L is a —C=C— or a —C—C—, and m, n, R¹ and R² are as described above.

The present invention is also directed to novel organic compounds among those disclosed above, and to pharmaceutical compositions that comprise these compounds. For the sake of convenience, these compounds will be referred to herein collectively as "active compounds," though it is to be understood that the other compounds with which they are combined, admixed, etc., in various embodiments disclosed herein are also "active" in a biological or pharmacological sense. As is disclosed in more detail below, the active compounds of this invention are typically admixed with one or more pharmaceutically acceptable carriers and/or excipients that are well known in the art for human and veterinary uses to make a pharmaceutical composition or a therapeutic composition (which terms are used interchangeably).

U.S. Pat. Nos. 6,599,945 and 7,094,809 described above disclose KST-201, KST-301, KST-401 and KST-213 and describe their use in methods of inhibiting the formation of infectious herpes virus particles or for treating gonorrhea caused by *Neisseria gonorrhoeae*. Synthesis of KST-213 is shown, although no biological activity for this compound was identified. None of these documents (not the other documents focused on resveratrol) disclose or suggest the specific compounds and methods and uses of the compounds that are claimed herein. To the extent that any specific disclosure in these publications or other publications may be considered to anticipate any generic aspect of the present invention, the disclosure of the present invention should be understood to include a proviso or provisos that exclude of disclaim any such species that were previously disclosed. The aspects of the present invention which are not anticipated by the disclosure of said publications are also unobvious from the disclosure of these publications, due at least in part to the unexpectedly superior results disclosed or alleged herein.

Development of Novel Compounds from Quantitative Structure Activity Relationships (QSAR)

The anti-inflammatory activities of resveratrol are believed to be due to its ability to inhibit the NF-κB and AP-1 signaling pathways, their upstream kinases and their downstream targets—including inducible cyclooxygenase-2 (COX2), inducible nitric oxide synthase (NOS) and matrix metalloprotease-9 (MMP9)). Because of these properties, resveratrol inhibits proliferation and induces cell death. However, this compound's relatively short half-life in vivo and its tendency to assume the cis-isomer conformation, has prompted the need to discover or synthesize more potent analogues or derivatives. The present inventor exploited Structure-Activity Relationship (SAR) and Structure-activity Map (SAM) studies.

SAMs, an application of SAR studies were employed to investigate the correlation of structure and bioactivity for resveratrol analogs. This is an efficient method for representing and visualizing a huge amount of information in a chemical database, and a simple approach for grouping and ordering molecules. By comparing the grouped topological isomers, it is useful to determine trends of particular bioactivities relevant to chemical structures (Tsai C C, et al., 1987, *Stud, Phys Theor Chem* 51:231-6; Parakulam, R R et al. 1999, *SAR and QSAR in Envir Res* 10:175-206). Similarity of chemical structures presented in the same group is expected to expose critical sites responsible for a biological property.

Number of atoms and bonds, NAB, is a topological molecular descriptor used to quantify the chemical structure. It is an integer value that denotes the number of non-hydrogen atoms and bonds in a molecule, classifying molecules into topological isomer groups (Parakulam et al., supra.). Plotting NAB of molecules of interest against their biological activities, for instance 50% effective dose ($ED_{50}$) or percent inhibition, generates SAMs. Original bioactivity data and chemical structures of resveratrol (and its analogs) were obtained from published papers which discussed certain properties such as antioxidant action, inhibition of nitric oxide production and anti-allergic action (Choa, D.-I. et al., 2002, *Life Sci* 71:2071-82; Cheong, H et al., 1999, *Planta Medica* 65:266-8; Lu, M et al., 2002, *Pharmazie* 57:474-8; Stivala, L A et al., 2001, *J Biol Chem* 276:22586-94).

SAMs are used to compare the grouped topological isomers for determination of trends of particular bioactivities relevant to chemical structures, and then critical sites responsible for a biological property, anticancer action in this study, might be obtained. This is the basis for further prediction and design of the new compounds.

The antioxidant activity of resveratrol analogs has been evaluated by analysis of: a.) the inhibition of citronellal thermo-oxidation, b.) the reduction of 2,2-diphenyl-1-picryl-hydrazyl radical (DPPH) and c.) the protection against lipid peroxidation. SAMs were prepared using the data of Stivala et al. supra, with the antioxidant activity being plotted against NAB (Table 1). The efficient quantity (EQ) of citronellal indicates the concentration needed for the compound to double the half-life of citronellal during the process of degradation due to heating and oxygenation. The efficient concentrations to reach 50% inhibition ($EC_{50}$) of microsomes and DPPH represent the concentrations required to decrease the initial amount of lipid peroxidation in rat liver microsomes and DPPH by 50%. The lower the EQ or $EC_{50}$, the more efficient the antioxidant activity. Among all six analogs (stilbenes and one diphenyl ethane), resveratrol was located at the lowest position in both SAMs of citronellal thermo-oxidation and the protection against lipid peroxidation, and almost the lowest in the map of the reduction of DPPH suggesting the most effective antioxidant property. Moreover, the results indicated the essential free 4'-hydroxyl group for antioxidant activity that could be enhanced by free 3- and 5-hydroxyl groups, and the compound with double bond and trans-conformation presented stronger activity compared with those with single bond and cis-conformation in the linker portion.

TABLE 1

NAB and Quantified Antioxidant Activities of Resveratrol and Its Analogues

| Compound | Structure | No. of non-H atoms | No. of non-H bonds | NAB | Citronellal EQ | Microsomes EC50 | DPPH EC50 |
|---|---|---|---|---|---|---|---|
| trans-3,4',5-Trihydroxystilbene | | 17 | 18 | 35 | 135 | 0.77 | 24.5 |
| cis-3,4',5-Trihydroxystilbene | | 17 | 18 | 35 | 241 | 1.10 | 24.1 |
| 3,5-Dihydroxy-4'-methoxystilbene | | 18 | 19 | 37 | 661 | 2.40 | 48.6 |
| 3,5-Dimethoxy-4'-hydroxystilbene | | 19 | 20 | 39 | 355 | 1.22 | 30.1 |
| 3,4',5-Trimethoxystilbene | | 20 | 21 | 41 | 1000 | | |

TABLE 1-continued

NAB and Quantified Antioxidant Activities of Resveratrol and Its Analogues

| Compound | | No. of non-H atoms | No. of non-H bonds | NAB | Antioxiant activities | | |
|---|---|---|---|---|---|---|---|
| | | | | | Citronellal EQ | Microsomes EC50 | DPPH EC50 |
| α,β-Dihydro-3,4',5-trihydroxystilbene | [structure] | 17 | 18 | 35 | 260 | 1.57 | 106.8 |

Another evaluation was performed on data of Lu et al., supra, who synthesized six hydroxystilbenes and then evaluated their antioxidant activities resveratrol by measuring inhibition of lipid peroxidation induced in different rat-organ homogenates by $Fe^{2+}$ and Vitamin C or via rat erythrocyte (RBC) hemolysis induced by $H_2O_2$. Lipid peroxidation induced by $Fe^{2+}$ with Vitamin C was determined by the levels of malondialdehyde (MDA) produced (Table 2-4). Inhibition ratio versus NAB was plotted as a structure-activity map. To summarize, the ortho- or para-conformation of hydroxyl groups seemed necessary for effective antioxidant activity, and the presence of a 4'-hydroxyl group increased activity.

Using the information derived from these SAMs and others (not shown), several new compounds (A series) were synthesized that contained a different number of hydroxyl groups on various positions on both of the aromatic rings while the double bonded linker was maintained. A second set of compounds (B series) was also synthesized that maintained the hydroxylation pattern of the A series, but also replaced the double bonded linker with a triple bonded linker. Despite the change in the linker from double bonded in the A series to triple bonded in the B series, the compounds with the corresponding hydroxylation patterns in the A series and B series would have the same NAB.

TABLE 2

NAB and inhibitory potency of lipid peroxidation of resveratrol and its analogs

| Compound | | No. of non-H atoms | No. of non-H bonds | NAB | Inhibition (%) of $Fe^{2+}$ – VitC induced level of MDA at 15 μM | | |
|---|---|---|---|---|---|---|---|
| | | | | | In rat brain | In rat liver | In rat kidney |
| trans-4-Hydroxystilbene | [structure] | 15 | 16 | 31 | 43.36 | 32.85 | 29.23 |
| trans-4,4'-Dihydroxystilbene | [structure] | 16 | 17 | 33 | 90.66 | 68.37 | 85.23 |
| trans-3,5-Dihydroxystilbene | [structure] | 16 | 17 | 33 | 12.24 | 24.82 | 0.62 |

TABLE 2-continued

NAB and inhibitory potency of lipid peroxidation of resveratrol and its analogs

| Compound | Structure | No. of non-H atoms | No. of non-H bonds | NAB | Inhibition (%) of $Fe^{2+}$ – VitC induced level of MDA at 15 μM | | |
|---|---|---|---|---|---|---|---|
| | | | | | In rat brain | In rat liver | In rat kidney |
| trans-2,4-Dihydroxystilbene | | 16 | 17 | 33 | 55.19 | 42.58 | 39.08 |
| trans-3,4-Dihydroxystilbene | | 16 | 17 | 33 | 96.68 | 99.27 | 89.23 |
| trans-3,4',5-Trihydroxystilbene | | 17 | 18 | 35 | 83.20 | 50.36 | 62.15 |
| trans-2,4,4'-Trihydrostilbene | | 17 | 18 | 35 | 94.40 | 92.46 | 87.69 |

TABLE 3

NAB and inhibitory potency of lipid peroxidation of resveratrol and its analogs

| Compound | Structure | No. of non-H atoms | No. of non-H bonds | NAB | Inhibition (%) of autooxidation MDA level at 7.5 μM | | |
|---|---|---|---|---|---|---|---|
| | | | | | In rat brain | In rat liver | In rat kidney |
| trans-4-Hydroxystilbene | | 15 | 16 | 31 | 6.64 | −2.31 | 19.88 |
| trans-4,4'-Dihydroxystilbene | | 16 | 17 | 33 | 85.31 | 89.23 | 62.11 |

TABLE 3-continued

NAB and inhibitory potency of lipid peroxidation of resveratrol and its analogs

| Compound | No. of non-H atoms | No. of non-H bonds | NAB | Inhibition (%) of autooxidation MDA level at 7.5 μM | | |
|---|---|---|---|---|---|---|
| | | | | In rat brain | In rat liver | In rat kidney |
| trans-3,5-Dihydroxystilbene | 16 | 17 | 33 | −5.24 | −5.38 | 14.91 |
| trans-2,4-Dihydroxystilbene | 16 | 17 | 33 | 30.07 | 42.31 | 32.27 |
| trans-3,4-Dihydroxystilbene | 16 | 17 | 33 | | | |
| trans-3,4',5-Trihydroxystilbene | 17 | 18 | 35 | 69.93 | 67.69 | 40.37 |
| trans-2,4,4'-Trihydroxystilbene | 17 | 18 | 35 | 90.91 | 93.85 | 66.46 |

TABLE 4

NAB and inhibitory potency of lipid peroxidation of resveratrol and its analogs

| Compound | No. of non-H atoms | No. of non-H bonds | NAB | Inhibition (%) of RBC hemolysis induced by $H_2O_2$ at 4 μM |
|---|---|---|---|---|
| trans-4-Hydroxystilbene | 15 | 16 | 31 | −5.14 |

TABLE 4-continued

NAB and inhibitory potency of lipid peroxidation of resveratrol and its analogs

| Compound | No. of non-H atoms | No. of non-H bonds | NAB | Inhibition (%) of RBC hemolysis induced by $H_2O_2$ at 4 μM |
|---|---|---|---|---|
| trans-4,4'-Dihydroxystilbene | 16 | 17 | 33 | 67.17 |
| trans-3,5-Dihydroxystilbene | 16 | 17 | 33 | 19.97 |
| trans-2,4-Dihydroxystilbene | 16 | 17 | 33 | 43.72 |
| trans-3,4-Dihydroxystilbene | 16 | 17 | 33 | 97.58 |
| trans-3,4',5-Trihydroxystilbene | 17 | 18 | 35 | 45.23 |
| trans-2,4,4'-Trihydroxystilbene | 17 | 18 | 35 | 81.85 |

These new compounds and resveratrol were evaluated for their cytotoxicity against Vero cells and antiviral activity against cells and animals infected with Herpes Simplex Virus-Type 1 (HSV-1). See Example II for tumor cell cytotoxicity of these compounds.

Approaches to Synthesis of Hydroxylated and Poly-Hydroxylated Tolans

The synthetic schemes described below are those used by the present inventor and colleagues in producing the indicated compounds. They are not intended here as exclusive approaches or schemes; more efficient methods, currently known or yet to be discovered may also be used, Rather these are illustrative of the inventor's preferred methods. A general scheme for preparing polyhydroxylated tolans is shown below.

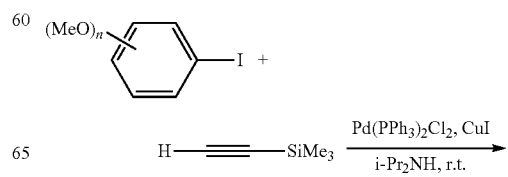

-continued

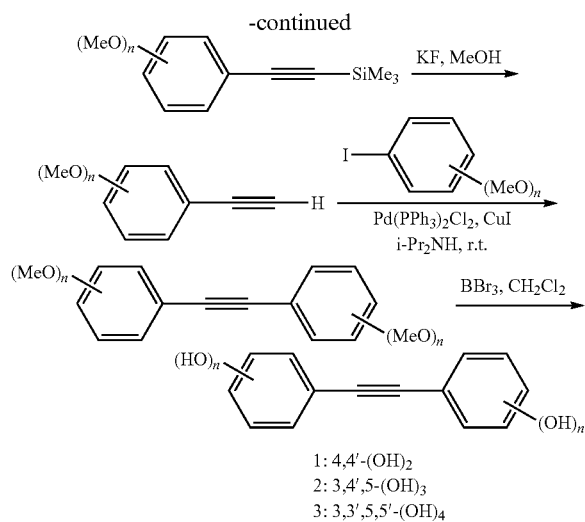

1: 4,4'-(OH)$_2$
2: 3,4',5-(OH)$_3$
3: 3,3',5,5'-(OH)$_4$

A. Synthesis of 3,5-dimethoxyiodobenzene from 3,5-dimethoxyaniline

In a 500 ml, 3-necked, round-bottomed flask equipped with a thermometer, a mechanical stirrer and an addition funnel was placed HCl (12 M, 100 ml, 1.2 mol) and crushed ice (100 g). The flask was immersed in a dry ice-Me$_2$CO cooling bath, and 3,5-dimethoxyaniline (15.3 g, 100 mmol) was added with stirring. To this cold mixture NaNO$_2$ (8.4 g, 120 mmol) in 40 ml H$_2$O was added dropwise at such a rate to maintain the temperature of the reaction mixture between −10° C. and −5° C. throughout the addition. The reaction mixture was stirred for 1 hour between 0° C. and 5° C. The red dark solution of the diazonium salt was added to a well-stirred solution of KI (83 g, 500 mmol) in 200 ml H$_2$O at room temperature. The mixture was stirred for 2 hours, and then allowed to stand overnight. The resulting solution was extracted with ether (200 ml×4). The pooled organic extracts were washed with brine (200 ml×2) and an aqueous saturated Na$_2$S$_2$O$_3$ solution (200 ml×2), dried over MgSO$_4$, filtered and concentrated to a small volume. Silica gel was added, and the mixture evaporated to dryness. This preloaded silica gel was placed on a pad of silica gel and eluted with petroleum to give 17.5 g (66%) of a colorless solid, 3,5-dimethoxyiodobenzene. $^1$HNMR (CDCl$_3$, 300 Mz): δ ppm: 6.85 (2H, d, J=2.3, Ar—H), 6.40 (1H, t, J=2.3, Ar—H), 3.76 (s, 6H, 2CH$_3$O).

B. Synthesis of Arylethynyltrimethylsilanes from Ethynyltrimethylsilane and Aryl Iodides General Procedure:

To a solution of aryl methoxy substituted aryl iodide (40 mmol) in isopropylamine (250 ml) were added Pd(PPh$_3$)$_2$Cl$_2$ (0.4 mmol) and CuI (0.8 mmol), then trimethylsilylacetylene (44 mmol). The reaction mixture was stirred at ambient temperature for 2 to 4 hours under a slow stream of nitrogen. The reaction mixture was filtered and the residues were washed with ethyl acetate, and the solvent evaporated from the combined filtrates. The crude product was purified by column chromatography on silica gel using petroleum/ethyl acetate as an eluent to give the methoxy substituted arylethylyl trimethylsilanes.

(1) 2-(4-methoxyphenyl)-1-trimethylsilyl-ethyne

Purified by column chromatography on silica gel using petroleum ether as an eluent to give 2-(4-methoxyphenyl)-1-trimethylsilyl-ethyne (96% yield) as a light yellow oil.

(2) 2-(3,5-dimethoxyphenyl)-1-trimethylsilyl-ethyne

Purified by column chromatography on silica gel using petroleum ether as an eluent to give 2.2 g (94%) light yellow needles.

$T_{GC}$=5.39 ($T_{init}$=50° C.). $^1$HNMR (CDCl$_3$, 300 Mz): δ ppm: 6.6 (s, 2H, Ar—H), 6.43 (s, 1H, Ar—H), 3.77 (s, 6H, 2CH$_3$), 0.24 (s, 9H, SiMe$_3$).

C. Synthesis of Methoxy Substituted Arylacetylenes

To a solution of arylethynyltrimethylsilanes (30 mmol) in methanol (30 ml) was added potassium fluoride (3.5 g, 60 mmol). The reaction mixture was stirred at room temperature for 2 hours. After removal of methanol, the product was extracted with ether (100 ml×3) and purified by chromatography on silica gel using petroleum ether as eluent to afford pure products.

(1) p-Methoxyethynylbenzene

Pale yellow oil was obtained in 92% yield. $^1$HNMR (CDCl$_3$, 300 Mz): δ ppm: 7.94 (d, 2H, J=8.98, Ar—H), 6.83 (d, 2H, J=8.55, Ar—H), 3.80 (s, 3H, Ch$_3$O), 3.00 (s, 1H—H).

(2) 3,5-Methoxyrthylnylbenzene

Pale yellow needle was obtained in 91% yield. $^1$HNMR (CDCl$_3$, 300 Mz): δ ppm: 7.94 (d, 2H, J=2.4, Ar—H), 6.83 (d, 2H, J=2.3, Ar—H), 3.78 (s, 6H, 2Ch$_3$O), 3.94 (s, 1H—H).

D. Synthesis of Methoxytolans

General Procedure:

To a solution of methoxyethynylbenzenes (20 mmol) and methoxy substituted aryl iodide (22 mmol) in isopropylamine (120 ml) were added Pd(PPH$_3$)$_2$Cl$_2$ (0.2 mmol) and CuI (0.4 mmol). The reaction mixture was stirred at ambient temperature for 6 hours under a slow stream of nitrogen. The reaction mixture was filtered and the residues were washed with ethyl acetate and the solvent evaporated from the combined filtrates. The crude product was purified by column chromatography on silica gel using petroleum ether/ethyl acetate (9:1) as an eluent to give methoxytolans.

(1) 3,4',5-Trimethoxyltolan

A pale yellow oil was obtained in 93% yield. $^1$HNMR (CDCl$_3$, 300 Mz): δ ppm: 7.46 (d, 2H, J=8.6, Ar—H), 6.88 (d, 2H, J=8.8, Ar—H), 6.66 (d, 2H, J=2.3, Ar—H), 6.44 (t, 2H, J=2.3, Ar—H), 3.83 (s, 3H, CH$_3$O), 3.80 (s, 6H, 2CH$_3$O).

(2) 3,3',5,5'-Tetramethoxytolan

A colorless needle crystal was obtained in 85% yield. $^1$HNMR (CDCl$_3$, 300 Mz): δ ppm: 6.69 (d, 4H, J=2.3, Ar—H), 6.46 (d, 2H, J=2.3, Ar—H), 6.66 (d, 2H, J=2.3, Ar—H), 3.80 (s, 12H, 4CH$_3$O).

(3) 4,4'-Dimethoxytolan

A colorless needle crystal was obtained in 91% yield. $^1$HNMR (CDCl$_3$, 300 Mz): δ ppm: 7.46 (d, 4H, J=8.7, Ar—H), 6.87 (d, 2H, J=8.7, Ar—H), 3.82 (s, 6H, 2CH$_3$O).

E. Synthesis of Hydroxytolans

General Procedure:

In a dry 250 ml, 3-necked, round-bottomed flask was placed a solution of methoxytolans (10 mmol) in anhydrous methylene chloride under N$_2$. The reaction mixture was cooled to below −20° C., and BBr$_3$ (20 mmol×the number of methoxy groups) was added by syringe. Then the reaction mixture was permitted to warm up to room temperature and stirred for over 24 hours. The reaction mixture (a reddish clear solution) was then poured into ice-water and stirred. After sufficient stirring, an aqueous NaHCO$_3$ solution was added to adjust the pH of the mixture to between 7 and 8. Then the mixture was extracted with ethyl acetate 3-4 times. The organic layer was washed with brine and dried over MgSO$_4$. Solvent was removed under reduced pressure. The red brown color crude product was purified by column chromatography on silica gel using petroleum/ethyl acetate (1:1) as an eluent to give hydroxytolans.

(1) 3,4',5-Trihydroxytolan

A pale yellow solid was obtained in 82% yield. $^1$HNMR (CDCl$_3$, 300 Mz): δ ppm: 9.89 (s, 1H, OH), 9.45 (s, 2h, 2-OH), 7.33 (d, 2H, J=8.65, Ar—H), 6.78 (d, 2H, J=8.63, Ar—H), 6.31 (d, 2H, J=2.2, Ar—H), 6.23 (d, 2H, J=2.2, Ar—H).

(2) 3,3',5,5'-Tetrahydroxytolan

A pale red solid was obtained in 92% yield. $^1$HNMR (CDCl$_3$, 300 Mz): δ ppm: 9.49 (s, 4H, 4-OH), 6.33 (d, 4H, J=2.2, Ar—H), 6.25 (t, 2H, J=2.2, Ar—H).

(3) 4,4'-Dihydroxytolan

A white solid was obtained in 93% yield. $^1$HNMR (CDCl$_3$, 300 Mz): δ ppm: 9.82 (s, 2H, 2-OH), 7.31 (d, 4H, J=8.7, Ar—H), 6.77 (d, 4H, J=8.7, Ar—H).

References: 1. Ali, M A et al., *Chem Pharm Bull*, 1992, 40:1130-6; 2. Pavia, M R et al., *Bioorg Med Chem*, 1996; 4:659-66. 3. Jeffery, T, *Tetrahedron Lett*, 1994, 35:3051-4. 4. Jeffery, T et al., *Tetrahedron Lett*, 1994, 35:4103-6. 5. Schmidt-Radde, R H et al., *J Am Chem Soc*, 1992, 114:9713-15; 6. Schumm, J S et al., *Angew Chem, Int Ed Eng.*, 1994, 33:1360-3; 7. Pal, M et al., *J Chem Soc Perkin Trans*, 1996, 1:449-51; 8. Bumagin, N A et al., *Russ J Org Chem*, 1996, 32:996-1000; 9. Bumagin, N A et al., *Tetrahedron Lett*, 1996, 37:897-900; 10. Meier H et al., *J Org. Chem.*, 1997, 62:4821-6.

Approaches to Synthesis of 4-Hydroxy-4'-trifluoromethyltolan (KST-213)

As above, the synthetic schemes described below are those used by the present inventor and colleagues in producing the indicated compounds. They are not intended here as exclusive approaches or schemes, but rather are illustrative of preferred methods.

A synthetic scheme for the preparation of 4-hydroxy-4'-trifluoromethyltolan (KST-213) is shown in the diagram below. Synthetic details of the specific reaction steps are described below. Most of these reactions are readily accomplished with high yields (over 90%). All products are preferably purified by column chromatography and characterized by GC and $^1$HNMR spectrometry.

1. 1-Iodo-4-tetrahydropyranyloxybenzene 1

To a stirred solution of 4-iodophenol (11.0 g, 50 mmol) in CH$_2$Cl$_2$ (50 ml) cooled with an ice bath, dihydropyran (5.0 g, 60 mmol) was added dropwise over 10 min at 0° C. to 5° C. After the solution became clear, toluenesulfonic acid, TsOH (10 mg) was added. The solution was stirred at 20° C. for 15 min. Then it was quenched by addition of NaHCO$_3$ (1 g) and 3 drops of water, and after stirring for 5 min at 20° C., the solvent was removed in vacuo and the residue was purified by column chromatography on silica gel with petroleum ether as eluent to give 14.0 g (92%) of 1 as colorless crystal; mp 66° C.; δ$_H$(CDCl$_3$, 300 MHz): 7.55 (d, J=8.3, 2H, Ar—H), 6.83 (d, J=8.4, 2H, Ar—H), 5.37 (t, J=3.1, 1H, OCHO), 3.86 (m, 1H, THP), 3.59 (m, 1H, THP), 1.87~1.58 (m, 6H, THP).

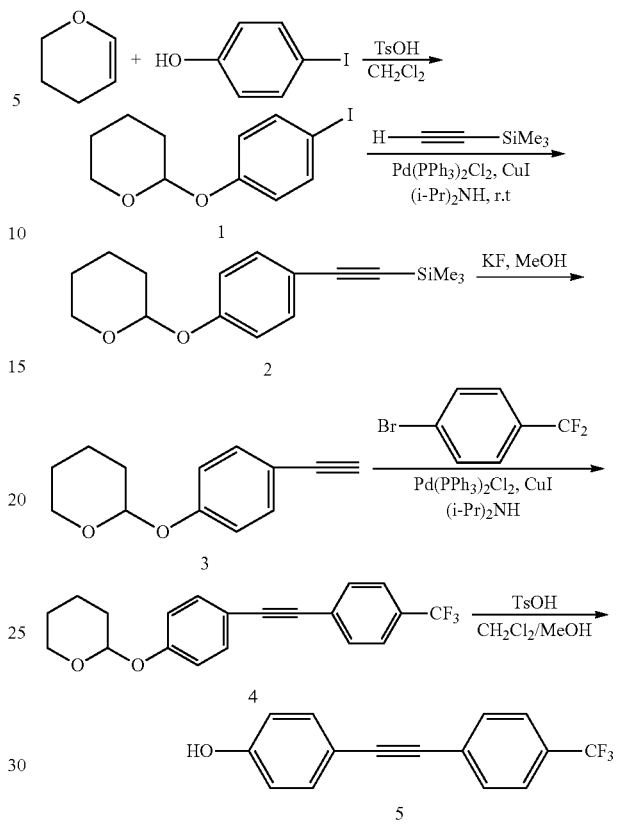

2. 4-Tetrahydropyranyloxy-1-(trimethylsilylethynyl)benzene 2

To a degassed solution of compound I (9.12 g, 30 mmol) in diisopropylamine (180 ml) under nitrogen, Pd(PPh$_3$)$_2$Cl$_2$ (140 mg, 0.2 mmol) and CuI (78 mg, 0.4 mmol) were added. Then trimethylsilyl acetylene (3.3 g, 33 mmol) was added dropwise to this clear solution. The reaction mixture was stirred for 2 hours at room temperature. The salt formed during the reaction procedure was filtered off and washed well with ethyl acetate. The filtrate was evaporated to dryness and hydrolyzed with concentrated hydrochloric acid (5 ml), water (25 ml) and crushed ice (10 g), then extracted with ethyl acetate. The combined organic paste was washed with brine and dried with MgSO$_4$. The solvent was removed in vacuo and the residue was purified by column chromatography (petroleum ether-ethyl acetate=9:1) to give a yellow oil of 2. Yield 7.9 g (96%); δ$_H$(CDCl$_3$, 300 MHz): 7.39 (d, J=8.7, 2H, Ar—H), 6.97 (d, J=8.6, 2H, Ar—H), 5.41 (t, J=3.1, 1H, OCHO), 3.84 (m, 1H, THP), 3.59 (m, 1H, THP), 1.86~1.61 (m, 6H, THP), 0.23 (s, 9H, 3 CH$_3$).

3. 4-Tetrahydropyranyloxyphenylacetylene 3

KF (9.3 g, 160 mmol) was added to a stirred solution of 2 (22.6 g, 80 mmol) in MeOH (150 ml). The reaction mixture was stirred at room temperature for about 4 hours. After the reaction finished (GC shows no starting material remaining), the solvent was removed under reduced pressure on a rotary evaporator. The residue was purified by column chromatography on silica gel (petroleum ether-ethyl acetate=9:1) to give a pale yellow crystals of 3. Yield 15.7 g (97%); mp 65° C., δ$_H$(CDCl$_3$, 300 MHz): 7.42 (d, J=8.7, 2H, Ar—H), 7.00 (d, J=8.7, 2H, Ar—H), 5.43 (t, J=3.2, 1H, OCHO), 3.87 (m, 1H, THP), 3.60 (m, 1H, THP), 2.99 (s, 1H, C≡C—H), 1.96~1.56 (m, 6H, THP).

4. 4-Tetrahydropyranyloxy-4'-trifluormethyltolan 4

A solution of 3 (12.1 g, 60 mmol) and 4-bromobenzotrifluoride (14.85 g, 66 mmol) in diisopropylamine (250 ml) was heated to 30° C. under nitrogen, and the solution was degassed. Then Pd(PPh$_3$)$_2$Cl$_2$ (210 mg, 0.3 mmol) and copper (I) iodide (114 mg, 0.6 mmol) were added to this clear solution. The reaction mixture was stirred for 2 hours at 80° C., and then cooled to room temperature. The salt formed during the reaction procedure was filtered off and washed well with ethyl acetate. The filtrate was evaporated to dryness and hydrolyzed with concentrated hydrochloric acid (10 ml), water (100 ml) and crushed ice (50 g), then extracted with ethyl acetate. The combined organic paste was washed with brine and dried over MgSO$_4$. The solvent was removed in vacuo and the residue was purified by column chromatography (petroleum ether-ethyl acetate=9:1) to give a pale yellow crystals of 4. Yield 16.6 g (80%); mp 112~113° C.; $\delta_H$(CDCl$_3$, 300 MHz): 7.59 (s, 4H, Ar—H), 7.48 (d, J=8.7, 2H, Ar—H), 7.04 (d, J=8.7, 2H, Ar—H), 5.46 (t, J=3.1, 1H, OCHO), 3.89 (m, 1H, THP), 3.62 (m, 1H, THP), 1.86~1.62 (m, 6H, THP).

5. 5-Hydroxy-4'-trifluoromethyltolan 5

Compound 4 (13.84 g, 40 mmol), CH$_2$Cl$_2$ (75 ml) and MeOH (125 ml) were placed in a 250 ml round-bottomed flask, then TsOH (0.4 g, 0.4 mmol) was added. The reaction mixture was stirred at 30° C. for 1 hour. When the reaction was finished (TLC showed no starting material remaining), the solvent was removed by rotary evaporation and the residue was dissolved in EtOAc and filtered through silica gel. The solvent was removed and the solid was recrystallized from solvents of ethyl acetate and hexane (1:5) to give a pale yellow crystal 9.5 g (90%), mp 131-132° C., $\delta_H$(CDCl$_3$, 300 MHz): 7.59 (s, 4H, Ar—H), 7.44 (d, J=8.7, 2H, Ar—H), 6.82 (d, J=8.7, 2H, Ar—H), 5.16 (s, 1H, OH).

References: Shen, D et al., *J Matter Chem.*, 1999, 9:661. 2. Praefcke, K et al., *Angew. Chem. Int. Ed. Engl.*, 1990, 29:177; 3. Bouchta, A et al., *Liq Crystals*, 1992, 12:575; 4. Hsieh, C J et al., *Liq. Crystals*, 1994, 16:469

Synthesis for other tolans, stilbene derivatives and diphenylethane derivatives utilize methods that are known in the art, and are thus not reiterated here.

Combinations of the Above Polyphenolic Compounds with Ascorbate and Heterocycles The present inventor has discovered that a combination of ascorbate or ascorbate+a Hc/OH with certain hydroxytolans compounds not heretofore known to have anticancer activity are useful in killing cancer cells in vitro and in vivo and slowing the progression of tumor growth or metastasis. The inventor made the surprising discovery that modifying polyphenolic compounds by altering the number and/or position of the hydroxyl groups on the rings, and/or changing the chemical structure of the linkage between the aromatic rings, in particular to a —C≡C— (acetylene) linkage, results in compounds which, in combination with ascorbate kill cancer cells more rapidly and effectively while maintaining low toxicity to normal cells.

The invention disclosed herein exemplifies the surprising discovery that combining a conjugated polyhydroxylated, polycyclic compounds, particularly a hydroxytolan, with sodium ascorbate results in more rapid and effective killing of tumor cells.

One embodiment of the present pharmaceutical compositions and methods include a cyclic compound, preferably a heterocyclic compound, with a keto or hydroxyl group in a ring system, so that it can interact with ascorbate and achieve effects as have been described elsewhere for Vitamin K$_3$ and its analogues. Such cyclic compounds include benzoquinones, anthraquinones, naphthoquinone, pyrroles, furans, thiophenes imidazole, oxazole, thiazole, pyrazole, pyridines, pyrimidines, purines, quinolines (including but not limited to 8-hydroxyquinoline, aminoquinolines, chloroquine, bicinchoninic acid, cinchophen, clioquinol, mefloquine, primaquine, quninidine, quinine, topotecan), isoquinolines, carbazoles, indoles, picolines, tetracyclines, alkaloids, niacin, vitamin D, vitamin E, vitamin B$_1$, riboflavin, vitamin B$_6$, flavin mononucleotide (FMN), flavin adenine dinucleotide (FAD), vitamin B$_{12}$, terpenes, steroids, nicotinic acid, nicotinamide, NADH, NADP$^+$, NAD$^+$, dioxetanes, phenanthridines, acridines, ellipticines, fluorescein, azines, xanthenes, thioxanthenes, oxazines, thiazines, rhodamines, phycoerythrins, cyanines.

Cancer, Tumors and Neoplastic Cells

The present invention is directed to cancer treatment methods that include "monotherapy" with one (or more) hydroxytolans and related active compounds (stilbene and diphenylethane derivatives). Such treatment attenuates, retards, inhibits, decreases, impedes, or reverses, etc., tumor development and growth, at least in part by killing the cancer cells. The ability of the present compositions and methods to act in a preventative manner results in substantially reduced size of tumor, and even its elimination, thereby preventing, attenuating or reversing any pathological effects of the tumor or cancer on the patient.

Also intended is the use of the present formulations in conjunction with other conventional cancer treatment, including chemotherapy, radiotherapy, biotherapy and surgery or any combination thereof.

When used as a supplemental treatment, the method of the present invention, because of its nontoxic nature, can be initiated before the start of the conventional treatment, continued during intervals between subsequent recurring rounds of conventional therapy, and may be continued after cessation of conventional therapy.

Thus, the present methods are directed to the killing of neoplastic of cancer or metastatic cells and the treatment of any of a number of cancers, including solid tumors and leukemias and lymphomas. A "neoplastic" cell exhibits uncontrolled proliferation. Generally, progeny of a neoplastic cell are also neoplastic and do not undergo terminal differentiation in vivo in response to physiological signals. Neoplastic cells include cells that are also described as cancer cells, cancerous cells and transformed cells. Neoplastic cells may occur as single, isolated cells in the body or aggregated, either homogeneously (with other neoplastic cells) or heterogeneously, with other cell types, as in a tumor or other collection of cells. A "tumor" is a collection of cells (neoplastic or otherwise) in which at least some of the cells are in physical contact with one another, typically by sharing a common extracellular matrix. The terms "cancer," "carcinoma," and "cancerous" when used herein refer to or describe the physiological condition, preferably in a mammalian subject, that is typically characterized by unregulated, neoplastic cell growth.

Treatment of cancer, a tumor, a premalignant disease or a hyperproliferative disorder by the present compositions includes the killing, inhibiting or slowing the growth of the relevant target cells, or inhibiting the increase in size of a tumor or cancerous growth. This includes reducing cell numbers, or preventing metastasis. "Treatment" as used herein is not meant to imply or require total cure or disappearance of cancer or a growing tumor. "Treatment" or "treating" is also intended to include prophylaxis, i.e., the prevention of development of a tumor or cancer, either a primary tumor, or more commonly a metastatic tumor or a recurrent tumor at the same or a different site from the primary tumor.

Malignant and metastatic diseases and conditions (tumors and cancer) which can be treated in accordance with the present invention include, but are not limited to, solid tumors, e.g., carcinomas, sarcomas, lymphomas and other malignant or nonmalignant tumors such as those listed below. For a review of such disorders, see any textbook of clinical oncology, e.g., DeVita, V T et al., (eds), *Cancer: Principles and Practice of Oncology*, 7th Edition, Lippincott Williams & Wilkins; 2004).

Examples of types of cancers that are successfully treated by the present compositions and methods are presented in the list below and in Table 5, which is not intended to be limiting. Thus the present invention is directed to the treatment of pancreatic carcinomas, renal cell carcinomas, small cell lung carcinoma, non-small cell lung carcinoma, prostatic carcinoma, bladder carcinoma, colorectal carcinomas, breast, ovarian, endometrial and cervical cancers, gastric adenocarcinoma, primary hepatocellular carcinoma, genitourinary adenocarcinoma, thyroid adenoma and adenocarcinoma, melanoma, retinoblastoma, neuroblastoma, mycosis fungoides, pancreatic carcinoma, prostatic carcinoma, bladder carcinoma, myeloma, diffuse histiocytic and other lymphomas, Wilms' tumor, Hodgkin's disease, adrenal tumors (adrenocortical or adrenomedullary), osteogenic sarcoma, soft tissue sarcoma, Ewing's sarcoma, rhabdomyosarcoma and acute or chronic leukemias, islet cell cancer, cervical, testicular, adrenocortical, or adrenomedullary cancers, choriocarcinoma, embryonal rhabdomyosarcoma, Kaposi's sarcoma, etc.

Diseases of the Skin

In addition to the uses in the context of cancer, the pharmaceutical compositions of the invention are useful for treating humans and animals suffering from or prone to certain skin conditions, disorders or diseases associated with or caused by inflammation or by similar processes such as those that occur in inflammatory cells, as well as conditions related to solar damage or natural aging. For example, the compositions have utility in preventing or treating psoriasis, contact dermatitis (irritant-induced or allergic), atopic dermatitis (e.g., allergic eczema), actinic keratosis, keratinization disorders (including eczema), epidermolysis bullosa diseases (including pemphigus), exfoliative dermatitis, seborrheic dermatitis, erythemas (including erythema multiforme and erythema nodosum), damage caused by the sun or other light sources, discoid lupus erythematosus, dermatomyositis, and undesired skin changes resulting from natural aging. For detailed descriptions of such skin disorders, see, for example, Rook's Textbook of Dermatology, D. A. Burns et al., eds., 7th ed (or later), Blackwell Publishing Limited, 2004.

TABLE 5

List of Cancers/Tumors acoustic neuroma
Adenocarcinoma
angiosarcoma
Astrocytoma
basal cell carcinoma
bile duct carcinoma
bladder carcinoma
breast cancer
bronchogenic carcinoma
cervical cancer
Chondrosarcoma
Choriocarcinoma
colorectal carcinomas TABLE 5-continued List of Cancers/Tumors Craniopharyngioma
Cystadenocarcinoma
Embryonal carcinoma
Endotheliosarcoma
ependymoma
esophageal carcinoma
Ewing's tumor
Fibrosarcoma
gastric carcinoma
Glioma/glioblastoma
Head and neck cancers
Hemangioblastoma
Hepatocellular carcinoma
Hepatoma
Kaposi's sarcoma
leiomyosarcoma
liposarcoma
lung carcinoma
lymphangiosarcoma
lymphangioendotheliosarcoma
Lymphoma
Leukemia
medullary carcinoma
medulloblastoma
Melanoma
meningioma
mesothelioma
Multiple myeloma
Myxosarcoma
Nasopharyngeal carcinoma
Neuroblastoma
oligodendroglioma
osteogenic sarcoma
ovarian cancer
pancreatic cancer
papillary adenocarcinomas
pinealoma
prostate cancer
renal cell carcinoma
retinoblastoma
rhabdomyosarcoma
sebaceous gland carcinoma
seminoma
small cell lung carcinoma
squamous cell carcinoma
sweat gland carcinoma
Synovioma
testicular tumor
Thyroid cancer
Wilms' tumor The methods and compositions of the present invention are also used to treat precancers and prevent their progression to cancer, as indicated above.

During cancer progression, distinctive lesions occur that persist for a time and have a set of characteristic properties that permit them to be detected, diagnosed, prevented, and treated. A recent publication (Berman, J et al., 2006, *Cancer Detec Prevent.* 30:387-94, incorporated by reference in its entirety) summarized results of a consensus conference held in 2004 sponsored by the National Cancer Institute to develop a newer definition of precancers. The participants developed a working definition for the precancers that clinicians and researchers can use to distinguish precancers from non-neoplastic changes and from other types of changes that might be encountered during "cancer progression." This definition modified and made more general an earlier definition that had been proposed for endometrial intraepithelial neoplasia (e.g., Mutter G L et al., In: Crum C P et al., eds. *Diagnostic gynecologic and obstetric pathology*. Philadelphia: Saunders, 2006). All of the following five criteria were considered to apply in defining precancer:

(1) Evidence exists that the precancer is associated with an increased risk of cancer.
(2) When a precancer progresses to cancer, the resulting cancer arises from cells within the precancer.
(3) A precancer is different from the normal tissue from which it arises.
(4) A precancer is different from the cancer into which it develops, although it has some, but not all, of the molecular and phenotypic properties that characterize the cancer.
(5) There is a method by which the precancer can be diagnosed.

These five criteria were considered to represent the minimal set of conditions, necessary and sufficient, for a lesion detected by any method to be considered a precancer. All of the criteria must apply concurrently. The different kinds of precancers may vary in every biologic feature except those specified in the definition (identifiable lesions that precede the development of cancer). It is notable that the definition has no required morphologic criteria. Most earlier definitions of precancers presumed specific morphologic features that permitted them to be recognized. The specific diagnostic criteria are not limiting, so that cytogenetic, molecular, and even behavioral (phenotypic) properties are considered. A number of issues remained open after this conference.

While a number of human cancers have an identifiable precancer (see Table 6 below) it is expected that information regarding putative nonepithelial precancers will emerge as new genomic, proteomic, and functional data are generated in these non-epithelial models. Although the best examples of precancers today are epithelial, the definition adopted above is sufficiently general and open ended to be applicable to non-epithelial precancers.

Precancers are not obligate lesions preceding cancers. For example, adenomas are precancerous lesions that may lead to the development of colorectal carcinoma. However, it is not known whether every colorectal carcinoma is preceded by an adenoma, or whether some cases of colorectal carcinoma arise ab initio from a single transformed cell that appeared within a population of normal cells, and which was not associated with an identifiable precancerous lesion. Obviously, the practical benefits of precancer detection and therapy are diminished when the interval between the appearance of a precancer and its progression to an invasive cancer is brief.

At the histological level, epithelial precancers are relatively easy to define and to diagnose. Most are characterized as foci of atypical cells confined within the normal anatomic boundary of the epithelial compartment (i.e., the basement membrane). Atypical cells that have penetrated the basement membrane are considered malignant because they are invasive. The term "intraepithelial neoplasia" describes these lesions and includes specific criteria for their diagnosis. Despite certain open issues, precancers have distinctive biological properties that serve to separate them from the cancers, even if there is no intraepithelial compartment that can be examined for invasion. Some of the general properties of precancers that would apply to non-epithelial and epithelial precancers are as follows.

Regression—not all precancers progress to cancer. The regression rate of all precancerous lesions of bronchial epithelium was found to be 54% in one study (Breuer R H et al., 2005, *Clin Cancer Res* 11:537-43) and was unrelated to various risk factors. In cervical intra-intraepithelial neoplasia, on the other hand, lack of progression or regression was directly related to the degree of cytologic atypia, mitotic activity, and type of human papillomavirus infection (Nasiell K et al., 1983, *Obstet Gyneco;* 61:609-14). Most in situ neuroblastomas do not evolve into clinically apparent tumors (Henson et al., 2001, supra). In some nonepithelial malignant tumors, regression may be common (Krikorian J G et al., 1980, *Cancer* 46:2093-9). For instance, clinical regression was reported in 30% of cases of untreated follicular lymphomas (Horning S J et al., 1984 *N Engl J Med* 311:1471-5). Regression has rarely been reported in testicular germ cell neoplasms, neuroblastoma, melanoma, and other invasive cancers (Simpson K et al., 2007, *Ann Diag Pathol* 11:97-102). Regardless of the method of detection the lesions designated as precancers are often members of a biologically heterogeneous group comprised of some lesions that progress to cancer and other lesions, usually the majority, that persist without developing into invasive cancer or that regress. At present, it is not possible to distinguish precancers that progress from those (of similar morphology) that do not progress or that regress.

Precancer progression: Even though it is difficult to distinguish precancers that progress from those that do not progress, on a practical level again, epithelial precancers that do progress usually show greater cytologic atypia, more mitotic activity, and more genetic abnormalities than those that persist or regress. If a proliferative lesion typically transforms, over time, into a more aggressive lesion with identifiable features of the malignant phenotype not observed in the original lesion, this would be another reason to suspect that the original lesion is a precancer. Examples of non-epithelial proliferative lesions that occasionally transform into a more aggressive and morphologically malignant tumor are shown in Table 7.

Multiplicity of lesions: Carcinogenic agents often produce multiple precancers in animal models. Over time, some of these develop into cancers (McDonnell T J et al., 1991, *Nature* 349:254-6; Solt D B et al., 1977, *Am J Pathol* 88:595-618; Kirkpatrick C J et al., 2000, *Am J Pathol* 156:1455-67). The occurrence of multiple precancers seems also to exist in humans. An individual with hundreds of actinic keratoses is more likely to have one or more squamous cell carcinomas than an individual with only a few keratoses. An individual with hundreds of nevi will likely have a smaller number of atypical nevi and a very small number of malignant melanomas. Colon adenomas that develop in familial adenomatous polyposis are often synchronous and multiple, but it is unusual to find patients with multiple colon carcinomas.

TABLE 6

Most frequently occurring cancers of man all have identifiable precancerous lesions*

| Identifiable Precancerous Lesion | → Cancer that develops |
|---|---|
| Actinic keratosis/squamous cell carcinoma in situ | → Squamous carcinoma of skin |
| Adenocarcinoma in situ of endocervix | → Invasive adenocarcinoma of endocervix |
| Atypical ductal dysplasia/carcinoma in situ | → Invasive ductal carcinoma of breast |
| Atypical endometrial hyperplasia | → Endometrioid adenocarcinoma |
| Barrett's esophagus/dysplasia | → Esophageal adenocarcinoma |
| Bronchial squamous dysplasia/carcinoma in situ | → Squamous cell carcinoma of the lung |

TABLE 6-continued

Most frequently occurring cancers of man all have identifiable precancerous lesions*

| Identifiable Precancerous Lesion | → Cancer that develops |
|---|---|
| Cervical intraepithelial neoplasia | → Cervical squamous carcinoma |
| Colorectal adenoma | → Colorectal carcinoma |
| Gallbladder dysplasia/carcinoma in situ | → Invasive carcinoma of the gallbladder |
| Gastric dysplasia/carcinoma in situ | → Gastric adenocarcinoma |
| In situ medullary thyroid carcinoma | → Medullary thyroid carcinoma |
| In situ melanoma | → Melanoma |
| Intratubular germ cell neoplasia | → Invasive germ cell neoplasms |
| Myelodysplastic syndrome | → Leukemia |
| Oral dysplastic leukoplakia | → Oral squamous carcinoma |
| Pancreatic intraepithelial neoplasia | → Pancreatic adenocarcinoma |
| Progressive transformation of germinal centers | → Hodgkin's disease |
| Prostatic intraepithelial neoplasia | → Prostatic adenocarcinoma |
| Urothelial carcinoma in situ | → Invasive urothelial carcinoma |

Henson DE et al., eds. Pathology of incipient neoplasia. 3rd ed. New York: Oxford University Press, 2001; Greenberg A K et al., 2002, Respir Res. 3: 20-30; Bostwick D G et al., 2004, High-grade prostatic intraepithelial neoplasia. Mod Pathol 17: 360-79.; Henson D E et al., In: Kelloff G et al., eds., Cancer chemoprevention strategies for cancer chemoprevention, vol. 2. Totowa, NJ: Humana Press, 2005: pp69-96; Hruban R H et al., 2004, Am J Surg Pathol 28: 977-87.

When a proliferative lesion is multiple, it may well be a precancer. A number of human cancers are components of inherited neoplastic syndromes, such as MEN type IIa. Patients with this syndrome develop a precancerous lesion, known as C-cell hyperplasia or medullary thyroid carcinoma in situ (Albores-Saavedra J et al., 2001, *Endocr Pathol* 12:365-77). This precancerous lesion is often multicentric, nearly always bilateral, and can be detected by identification of the specific RET germline mutation. Other genetically determined syndromes are characterized by precancerous lesions that are multicentric and diagnosed preoperatively by genetic testing.

Chronologic precedence: Progression of precancers to cancer, if it occurs, takes place over time. Thus, for any given precancer, the average age of individuals in whom the precancer occurs should be younger than the average age of individuals in which the developed cancer occurs. The property of chronological precedence seems to be an inescapable truth. If populations were screened at regular intervals, and if there were methods to reliably detect precancers and cancers, it might be feasible to use epidemiologic data to determine the chronologic precedence of precancers. With few exceptions, this type of study has not been carried out.

TABLE 7

Examples of non-epithelial proliferative lesions that occasionally transform into a more aggressive and morphologically malignant tumor

| Lesion | → Malignant Tumor |
|---|---|
| Fibrous dysplasia | → Osteosarcoma |
| Neurofibroma | → Malignant peripheral nerve sheath tumor |
| Osteochondroma | → Chondrosarcoma of bone |
| Progressive transformation of germinal centers | → Lymphocyte-predominant Hodgkin's disease |

Pharmaceutical and Therapeutic Compositions and Their Administration

The compounds that may be employed in the treatment method of the invention include all the compounds of Formula I described above, as well as the pharmaceutically acceptable salts of these compounds. Pharmaceutically acceptable acid addition salts of the compounds of the invention containing a basic group are formed where appropriate with strong or moderately strong, non-toxic, organic or inorganic acids by methods known to the art. Exemplary of the acid addition salts that are included in this invention are maleate, fumarate, lactate, oxalate, methanesulfonate, ethanesulfonate, benzenesulfonate, tartrate, citrate, hydrochloride, hydrobromide, sulfate, phosphate and nitrate salts.

Pharmaceutically acceptable base addition salts of compounds of the invention containing an acidic group are prepared by known methods from organic and inorganic bases and include, for example, nontoxic alkali metal and alkaline earth bases, such as calcium, sodium, potassium and ammonium hydroxide; and nontoxic organic bases such as triethylamine, butylamine, piperazine, and tri(hydroxymethyl)methylamine.

A composition of this invention may be active per se, or may act as a "pro-drug" that is converted in vivo to the active form.

The compounds of the invention, as well as the pharmaceutically acceptable salts thereof, may be incorporated into convenient dosage forms, such as capsules, impregnated wafers, tablets or injectable preparations. Solid or liquid pharmaceutically acceptable carriers or excipients are preferably employed. The preparations which can be administered orally or which can be used for other modes of administration, including suitable solutions for administration by injection or infusion, preferably contain from about 0.01% to 15%, preferably from about 0.1% to 10% by weight or by volume of active compound(s), together with the carrier or excipient.

Solid carriers include starch, lactose, calcium sulfate dihydrate, terra alba, sucrose, talc, gelatin, agar, pectin, acacia, magnesium stearate and stearic acid. Liquid carriers include syrup, peanut oil, olive oil, saline, water, dextrose, glycerol and the like. Similarly, the carrier or diluent may include any prolonged release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., a solution), such as an ampoule, or an aqueous or nonaqueous liquid suspension. A summary of such pharmaceutical compositions may be found, for example, in Gennaro, A E, *Remington: The Science and Practice of Pharmacy*, Lippincott Williams & Wilkins Publishers; 2003 (or a later edition).

The pharmaceutical preparations are made using conventional techniques of pharmaceutical chemistry and formulation involving such steps as mixing, granulating and compressing, when necessary for tablet forms, or mixing, filling and dissolving the ingredients, as appropriate, to give the desired products for the various routes of administration described herein including oral and parenteral. The pharmaceutical compositions may contain minor amounts of non-toxic auxiliary substances such as wetting or emulsifying agents, pH buffering agents and so forth.

The present invention may be used in the treatment of any of a number of animal genera and species, and are equally applicable in the practice of human or veterinary medicine. Thus, the pharmaceutical compositions can be used to treat domestic and commercial animals, including birds and more preferably mammals, as well as humans.

The present invention provides pharmaceutical combinations or kits which when administered to a subject in need thereof, inhibit cancer cell growth and induce cancer cell death as well as methods of using such combinations to treat many forms of cancer as described, including, but not limited to, bladder, prostate and ovarian cancer. The invention provides a composition and a pharmaceutical composition for improving the effectiveness of certain therapeutically active phenolic compounds described above, preferably hydroxytolans, combined with ascorbate and/or an Hc/OH compound as described.

The term "systemic administration" refers to oral or parenteral administration of a compound described herein, in a manner that results in the introduction of the compound into the subject's circulatory system or otherwise permits its spread throughout the body, such as intravenous (i.v.) injection or infusion, intramuscular, rectal or transdermal administration. The present invention further includes the following routes of administration: subcutaneous, topical, intradermal, intraarterial, intraperitoneal, intralesional including intratumoral, intrathecal, intracranial, intraarticular, intravesical, intraprostatic, intrapericardial, intrapleural, intratracheal, intranasal, intravitreal, vaginal, mucosal, and the like. Administration may be local, regional, or systemic. Administration may be by aerosol (lung instillation), injection, infusion, continuous infusion, localized perfusion bathing target cells directly or via a catheter and/or lavage.

"Regional" administration refers to administration into a specific, and somewhat more limited, anatomical space, such as intraperitoneal, intrathecal, subdural, or to a specific organ. Other examples include intravaginal, intrapenile, intranasal, intrabronchial (or lung instillation), intracranial, intra-aural or intraocular. It is noted that intrathecal administration is not intended to be limited to a more commonly used definition of intracranial spaces. The compounds may be injected or instilled directly into a cavity or space ("thecum") surrounding an organ or body region in which a tumor is present or is causing fluid accumulation. Such spaces include the pleural space, peritoneum, subarachnoid space or dural space, or pericardial space. The generic term for administration into a sheath encasing an organ is termed "intrathecal," defined in Dorland's Medical Dictionary $29^{th}$ Edition, WB Saunders (2000) and Stedman's Medical Dictionary, $27^{th}$ Edition, Lippincott, Williams & Wilkins (2000) as meaning "within a sheath."

"Local administration" refers to administration of a composition or drug into a more limited or circumscribed anatomic space, such as intratumoral injection into a tumor mass or subcutaneous (s.c.) injection.

One of skill in the art will understand that local administration or regional administration often also results in entry of the active compound into the circulatory system, so that such routes, e.g., the s.c. route, may ultimately result in systemic administration of the compound.

The preparation of the present pharmaceutical compositions is known to those of skill in the art. (See for example, Gennaro, supra, or; Watson D, ed., *Pharmaceutical Analysis*, 1999 (or later edition), Harcourt Pub Ltd, London.) For human administration, it will be understood that the preparations meet the sterility, pyrogenicity, general safety and purity standards required by FDA Office of Biological Standards and other relevant regulatory bodies.

Injectable or infusible preparations can be prepared in conventional forms, either as solutions or suspensions, solid forms suitable for dissolution or suspension in liquid prior to injection or infusion, or as emulsions. Though the preferred routes of administration are systemic, such as i.v., the present pharmaceutical composition may be administered topically or e.g., as an ointment, cream or gel, or transdermally or rectally, e.g., as a suppository.

For topical application, the compound may be incorporated into topically applied vehicles such as a salve or ointment. The carrier for the active ingredient may be either in sprayable or nonsprayable form. Non-sprayable forms can be semi-solid or solid and comprise a carrier indigenous to topical application and have a dynamic viscosity preferably greater than that of water. Suitable topical formulations include, but are not limited to, solutions, suspensions, emulsions, creams, ointments, powders, liniments, salves, and the like. If desired, these may be sterilized or mixed with auxiliary agents, e.g., preservatives, stabilizers, wetting agents, buffers, or salts for influencing osmotic pressure and the like. Preferred vehicles for non-sprayable topical preparations include ointment bases, e.g., polyethylene glycol-1000 (PEG-1000); conventional creams such as HEB cream; gels; as well as petroleum jelly and the like. Oils of animal or plant origin such as peanut oil, mineral oil, soybean oil, or sesame oil, corn oil, or synthetic oils may be added. The liquid form of topical pharmaceutical composition may be in the form of a solution of physiological saline, with dextrose or other saccharide, or glycols such as ethylene glycol, propylene glycol or polyethylene glycol. The preparation of such topical composition having suitable pH, isotonicity, and stability, is within the skill in the art.

Also suitable for topic application as well as for lung instillation are sprayable aerosol preparations wherein the compound, preferably in combination with a solid or liquid inert carrier material, is packaged in a squeeze bottle or in admixture with a pressurized volatile, normally gaseous propellant. The aerosol preparations can contain solvents, buffers, surfactants, perfumes, and/or antioxidants in addition to the compounds of the invention.

The topical compositions of the present invention are particularly useful to treat cancerous or pre-cancerous skin conditions and other skin disorders described above. An effective amount of the compound in a topical carrier is administered to an affected area, e.g., skin surface, mucous membrane, eyes, etc. The formulations are administered to the skin or mucosal tissue as an ointment, lotion, cream, microemulsion, gel, solution or the like, as described herein, using a dosing regimen effective to bring about the desired result. The preferred dose of active agent, preferably KST-201, KST-213, KST-301 or KST-401 is in the range of about 0.5 to about 500 µg/kg/day, preferably about 10 to about 200 µg/kg/day, more preferably about 20 to about 150 µg/kg/day. It will be appreciated by those skilled in the art that the optimal quantity and spacing of individual dosages will be determined by the nature and extent of the condition being treated, the site(s) of administration, and the particular individual undergoing treatment, and that such an optimal regimen can be determined by conventional techniques. That is, an optimal dosing regimen, the number and frequency of doses, for any particular subject, can be ascertained using conventional course of treatment determination tests. Generally, the dosing regimen involves administration of the topical formulation at least once daily, and preferably one to four times daily, until symptoms have subsided.

The topical formulations of the invention can also be used as chemopreventive compositions. When used in a chemopreventive method, susceptible skin is treated prior to the development of a visible condition in a subject.

In one embodiment, a topical pharmaceutical composition containing the active compound, preferably a hydroxytolan compound as disclosed herein, is may be prepared in the form of a cream as follows:

TABLE 8

| Phase | Component | Wt. % |
|---|---|---|
| 1 | Polyethylene Glycol and Ethylene glycol Palmitostearate | 5% |
|  | Caprilic/Capric Triglycerides | 5% |
|  | Oleoyl Macrogolglycerides (Labrafil M 1944CS) | 4% |
|  | Cetyl Alcohol | 5.5% |
|  | PPG-2 Myristyl Ether Propionate (Crodamol PMP) | 6% |
| 2 | Xanthan Gum | 0.3% |
|  | Purified Water | 48% |
| 3 | Propylene Glycol | 1% |
|  | Methylparaben | 0.18% |
|  | Propylparaben | 0.02% |
| 4 | Active compound, e.g., KST-201, KST-213, KST-301 or KST-401 | 10% |
|  | Diethylene Glycol Monoethyl Ether (Transcutol) | 15% |

The topical composition may be prepared as follows. The xanthan gum is dispersed in water, and allowed to stand. Phase 1 (the oil phase) is heated to 75° C. Phase 2 is then heated to 75° C. Under high speed agitation, phase 1 is mixed into phase 2. The temperature is maintained at 75° C., and rapid stirring is continued for 10 min. The mixture is cooled slowly while stirring is continued at low speed. At 40° C., Phase is 3 is added. The active compound is then dispersed into diethylene glycol monoethyl ether, heated to 40° C., and then cooled to 30° C. while stirring slowly (Phase 4). At 30° C., Phase 4 is added to the cream, mixed well, and cooled to room temperature with slow mixing. A stable cream is obtained. A microemulsion of the active compound of the invention, e.g., KST-201, KST-213, KST-301 or KST-401, is prepared with the following components:

TABLE 9

| Component | Wt. % |
|---|---|
| Active compound, e.g., KST-201, KST-213, KST-301 or KST-401 | 10% |
| Diethylene Glycol Monoethyl Ether (Transcutol) | 47.4% |
| PEG-8 Caprylic/Capric Triglycerides (Labrasol) | 23.7% |
| Oleoyl Macrogolglycerides (Labrafil M 1944 CS) | 7.9% |
| PEG 400 | 4.7% |
| Water | 0.3% |

The active compound is dispersed into diethylene glycol monoethyl ether. PEG-8 caprylic/capric glycerides and oleoyl macrogolglycerides are added, with agitation. PEG 400 is then slowly added, again, with agitation, followed by addition of water. A stable microemulsion is thus obtained.

The topical composition may further contain other agents which enhance the uptake or activity of the active compound of the invention or complement its activity in treating the disease. Such additional factors and/or agents may be included in the pharmaceutical composition to produce a synergistic effect with the active compound or to minimize side effects.

Other pharmaceutically acceptable carriers for the compositions of the present invention, preferably the topical compositions, are liposomes. These are pharmaceutical compositions in which the active compound is preferably combined with amphipathic agents such as lipids which exist in aggregated form as micelles, insoluble monolayers, liquid crystals, or lamellar layers in aqueous solution. The hydrophobic layer, or lipidic layer, generally, but not exclusively, comprises phospholipids such as lecithin/lysolecithin and sphingomyelin, monoglycerides, diglycerides, sulfatides, steroids such as cholesterol, saponin, bile acids, and more or less ionic surface active substances such as dicetylphosphate, stearylamine or phosphatidic acid, and/or other materials of a hydrophobic nature. Those skilled in the art will appreciate other suitable embodiments of the present liposomal formulations. Preparation of such liposomal formulations is within the level of skill in the art.

Therapeutic compositions or methods for treating tumors and cancer may comprise, in addition to the present compound, one or more additional anti-tumor drugs or agents, such as mitotic inhibitors, e.g., vinblastine; alkylating agents, e.g., cyclophosphamide; folate inhibitors, e.g., methotrexate, antimetabolites, e.g., 5-fluorouracil and cytosine arabinoside, intercalating antibiotics, e.g., adriamycin and bleomycin; enzymes or enzyme inhibitors, e.g., asparaginase, topoisomerase inhibitors such as etoposide; or biological response modifiers, e.g., cytokines and interferons. In fact, pharmaceutical compositions comprising a known cancer therapeutic in combination with the compounds disclosed herein are within the scope of this invention. The pharmaceutical composition may also comprise one or more other medicaments to treat additional symptoms for which the target patients are at risk, for example, anti-infectives including antibacterial, anti-fungal, anti-parasitic, anti-viral, and anti-coccidial agents, since tumor-bearing patients may also suffer from various infections or have diminished resistance to infections.

The pharmaceutical compositions of the present invention may, if desired, be presented in a pack or dispenser device which may contain one or more unit dosage forms containing the active compound. The pack may, for example, comprise metal or plastic foil, such as a blister pack in the case of pills or capsules. The pack or dispenser device may be accompanied by instructions for administration. Compositions comprising a compound of the invention formulated in a compatible pharmaceutical carrier may also be prepared, placed in an appropriate container, and labeled for treatment of an indicated condition.

In the present methods, the compounds can also be administered in sustained release forms or from sustained release drug delivery systems. A description of representative sustained release materials can be found in Gennaro, supra.

The therapeutic dosage administered is an amount which is therapeutically effective in treating the target disease, preferably cancer, as is known or readily ascertainable by those skilled in the art. The dose is also dependent upon the age, health, and weight of the recipient, state or stage of the cancer, nature of concurrent treatment(s) if any, the frequency of treatment, and the nature of the effect desired. Effective doses or amounts can be determined in view of this disclosure by one of ordinary skill in the art by carrying out routine trials with appropriate controls. Comparison of the appropriate treatment groups to the controls will indicate whether a particular dosage is effective. An effective amount of the compound to treat a tumor or cancer is an amount sufficient to achieve a steady state concentration in vivo which results in treatment, healing, prevention, prophylaxis, amelioration, or reduction in the symptoms. In the art of tumor or cancer therapy, this preferably refers to a measurable reduction in a relevant parameter of disease such as attenuating or reversing growth of a primary or a metastatic tumor, reduction in tumor load, preventing or reducing recurrence or metastasis of a primary tumor, or a measurable prolongation of disease-free interval or of survival. For example, a reduction in tumor growth in 20% of patients is considered efficacious or effective. (See, for example, Frei III, E., "Clinical trials of antitumor agents: experimental design and timeline considerations," *Cancer J Sci Am.*, 1997, 3:127-36.) However, an effect of this magnitude is not considered to be a minimal requirement for the dose to be effective in accordance with this invention. Therapeutic or treatment responses can be complete response (CR) or partial responses (PR). DeVita et al., supra). Table 10, below shows accepted definitions, established by the International Union Against Cancer:

TABLE 10

| RESPONSE | DEFINITION |
| --- | --- |
| Complete response (CR) | Disappearance of all evidence of disease |
| Partial response (PR) | >50% decrease in tumor burden; no new lesions; no progression of pre-existing lesions |
| Less than partial response (<PR) | 25-50% decrease in tumor size, stable for at least 1 month |
| Stable disease | <25% reduction in tumor size; no progression or new lesions |
| Progression | >25% increase in size of any one measured lesion or appearance of new lesions despite stabilization or response of disease in other measured sites |

"Tumor burden" is the sum of the products of the areas (products of maximal perpendicular diameters) of each measurable lesion. As used herein, the tumor burden may either (a) stabilize, which is the failure of the tumor burden to increase, i.e., no new lesions and no increase in the area of any one lesion, or (b) decrease A preferred dose for treating a subject preferably a mammal, more preferably human, with a tumor is an amount of up to about 10 mg/kg body weight of the active compound—preferably a tolan compound, more preferably a hydroxytolan, or a combination of compounds as described above. A typical single dosage of the compound is between about 10 µg/kg and about 5 mg/kg body weight. For topical administration, dosages of about 0.1-15% concentration (by weight) of the compound, preferably 1-10%, are suggested. A total daily dosage of about 1 mg to about 350 mg is preferred for intravenous administration. The foregoing ranges are, however, suggestive, as the number of variables in an individual treatment regime is large, and considerable excursions from these preferred values are expected. Although a single application or administration of the present compounds may be sufficient to ameliorate some measurable symptoms or the pathologies, it is expected that multiple doses by one or more routes, possibly for periods as long as weeks, months and longer, will be required for the desired therapeutic outcomes.

When used in combination with VC or an ascorbate homologue, a preferred ratio of the VC or ascorbate homologue to the active compound of Formula I is between about 50 and 900, more preferably between about 100 and 600. For oral administration, the dose of VC or ascorbate homologue may range from about 15 mg to about 0.1 g per kg body weight per day. The dose range of an active hydroxytolan and ascorbate may be determined using the ratios given above. For i.v. or i.p, administration, the dose of the VC or ascorbate homologue is preferably in the range of 7 mg/kg/day to about 3 g/kg/day. In a preferred embodiment, the dose is about 30 mg/kg/day to 1 g/kg/day. The dose of the active compound, preferably a hydroxytolan, may be determined using the ratios shown above.

The (ascorbate/hydroxytolan) combination can be administered by any suitable manner or route, preferably e.g., orally, i.v. or i.p. The two agents can be delivered by different routes, e.g., injection of the hydroxytolan or related compound and oral administration of the ascorbate. In a preferred embodiment, both oral and intravenous administration are utilized during the course of treatment.

The hydroxytolans and other compositions of the present invention may also be used in conjunction with combinations of ascorbate and Hc/OH compounds described above. The amounts of Hc/OH in relation to the hydroxytolan compound and VC are determined using the parameters provided above.
In Vivo Testing of the Active Compounds In Vivo The active compounds and pharmaceutical compositions described herein are tested for therapeutic efficacy in several well established rodent models which are considered to be highly representative of a broad spectrum of human tumors. A non-limiting description of tumor models and angiogenesis models is described below. For a more comprehensive description of murine and rat tumor models, see, for example, Geran, R I et al., 1972, "Protocols for Screening Chemical Agents and Natural Products Against Animal Tumors and Other Biological Systems", *Canc. Chemother. Reports*, 3: (Part 3)1-63; and Talmadge, J E et al., "Murine Models to Evaluate Novel and Conventional Therapeutic Strategies for Cancer", *Amer J Pathol.* 2007, 170:793, which are hereby incorporated by reference in their entirety.

A. Xenograft Model of Subcutaneous (s.c.) Tumor Growth

Nude mice are inoculated with MDA-MB-231 cells—a human breast carcinoma line—or any other human tumor cell line that grows as a solid tumor, including the cell lines exemplified below, such as human prostate cancer cells (DU145 line), human bladder cancer cells (T24 line) and ovarian cancer cells (MDAH2274 line. The tumor cells are inoculated with Matrigel® (e.g., $10^6$ cells in 0.2 mL) s.c. in the right flank of the animals. The tumors are staged to 200 $mm^3$ and then treatment with a test composition is initiated (100 µg/animal/day given q.d. IP). Tumor volumes are obtained every other day and the animals are sacrificed after 2 weeks of treatment. The tumors are excised, weighed and paraffin embedded. Histological sections of the tumors are analyzed by hematoxylin and eosin staining, and staining with various marker-specific monoclonal antibodies such as CD31 and Cd68, Ki-67, and TUNEL staining for apoptosis.

B. Xenograft Model of Metastasis

The compounds of this invention are also tested for inhibition of late metastasis using an experimental metastasis model (Crowley, C W et al., *Proc. Natl. Acad. Sci. USA* 90 5021-25 (1993)). Late metastasis involves the steps of attachment and extravasation of tumor cells, local invasion, seeding, proliferation and angiogenesis. Human prostatic carcinoma cells (PC-3) or cells of another appropriate cell line are transfected with a reporter gene, preferably the green fluorescent protein (GFP) gene, but as an alternative, transfected with a gene encoding the enzyme chloramphenicol acetyltransferase (CAT), luciferase or LacZ, are inoculated into nude mice. This approach permits utilization of either of these markers (fluorescence detection of GFP or histochemical colorimetric detection of enzymatic activity) to follow the fate of these cells. Cells are injected, preferably iv, and metastases identified after about 14 days, particularly in the lungs but also in regional lymph nodes, femurs and brain. This mimics the organ tropism of naturally occurring metastases in human prostate cancer. For example, GFP-expressing PC-3 cells ($1\times10^6$ cells per mouse) are injected iv into the tail veins of nude (nu/nu) mice. Animals are treated with a test composition at 100 µg/animal/day given q.d. IP. Single metastatic cells and foci are visualized and quantitated by fluorescence microscopy or light microscopic histochemistry or by grinding the tissue and quantitative colorimetric assay of the detectable label.

C. Inhibition of Spontaneous Metastasis In Vivo by HPRG and Functional Derivatives In one approach, the rat syngeneic breast cancer system (Xing et al., *Int J. Cancer* 67:423-29 (1996) is used, employing Mat BIII rat breast cancer cells. Tumor cells, for example about $10^6$ suspended in 0.1 mL PBS, are inoculated into the mammary fat pads of female Fisher rats. At the time of inoculation, a 14-day Alza osmotic mini-pump is implanted intraperitoneally to dispense the test compound. The compound is dissolved in PBS (e.g., 200 mM stock), sterile filtered and placed in the minipump to achieve a release rate of about 4 mg/kg/day. Control animals receive vehicle (PBS) alone or a vehicle control peptide in the minipump. Animals are sacrificed at about day 14.

Outcomes: In the rats treated with the active compounds of the present invention, significant reductions in the size of the primary tumor and in the number of metastases in the spleen, lungs, liver, kidney and lymph nodes (enumerated as discrete foci) are observed. Histological and immunohistochemical analysis reveal increased necrosis and signs of apoptosis in tumors in treated animals. Large necrotic areas are seen in tumor regions lacking neovascularization.

D. 3LL Lewis Lung Carcinoma: Primary Tumor Growth

This tumor line arose spontaneously in 1951 as carcinoma of the lung in a C57BL/6 mouse (*Cancer Res* 15:39, 1955. See also Malave, I et al., *J Nat'l Canc Inst* 62:83-8 (1979)). It is propogated by passage in C57BL/6 mice by subcutaneous (sc) inoculation and is tested in semiallogeneic (C57BL/6× DBA/2) $F_1$ mice or in allogeneic C3H mice. Typically six animals per group for subcutaneously (sc) implant, or ten for intramuscular (im) implant are used. Tumor may be implanted sc as a 2-4 mm fragment, or im or sc as an inoculum of suspended cells of about $0.5-2\times10^6$-cells. Treatment begins 24 hours after implant or is delayed until a tumor of specified size (usually approximately 400 mg) can be palpated. The test compound is administered ip daily, for example, for 11 days.

Animals are followed by weighing, palpation and measurement of tumor size. Typical tumor weight in untreated control recipients on day 12 after im inoculation is 500-2500 mg. Typical median survival time is 18-28 days. A positive control compound, for example cyclophosphamide at 20 mg/kg/injection per day on days 1-11, is used. Results computed include mean animal weight, tumor size, tumor weight and survival time. For confirmed therapeutic activity, the test composition should be tested in two multi-dose assays.

E. 3LL Lewis Lung Carcinoma: Primary Growth and Metastasis Model

This model has been utilized by a number of investigators. See, for example, Gorelik, E et al., *J. Nat'l. Canc. Inst.* 65:1257-64 (1980); Gorelik, E et al., *Rec. Results Canc. Res.* 75:20-8 (1980); Isakov, N et al., *Invasion Metas.* 2:12-32 (1982); Talmadge J E et al., *J. Nat'l. Canc. Inst.* 69:975-80 (1982); Hilgard, P et al., *Brit J Canc* 35:78-86 (1977). Test mice are male C57BL/6 mice, 2-3 months old. Following sc, im, or intra-footpad implantation, this tumor produces metastases, preferentially in the lungs. With some lines of the tumor, the primary tumor exerts anti-metastatic effects and must first be excised before study of the metastatic phase (see also U.S. Pat. No. 5,639,725).

Single-cell suspensions are prepared from solid tumors by treating minced tumor tissue with a solution of 0.3% trypsin. Cells are washed 3 times with PBS (pH 7.4) and suspended in PBS. Viability of the 3LL cells prepared in this way is generally about 95-99% (by trypan blue dye exclusion). Viable tumor cells ($3\times10^4$-$5\times10^6$) suspended in 0.05 ml PBS are injected subcutaneously, either in the dorsal region or into one hind foot pad of C57BL/6 mice. Visible tumors appear after 3-4 days after dorsal sc injection of $10^6$ cells. The day of tumor appearance and the diameters of established tumors are measured by caliper every two days.

The treatment is given as one or two doses of peptide or derivative, per week. In another embodiment, the peptide is delivered by osmotic minipump.

In experiments involving tumor excision of dorsal tumors, when tumors reach about $1500 \text{ mm}^3$ in size, mice are randomized into two groups: (1) primary tumor is completely excised; or (2) sham surgery is performed and the tumor is left intact. Although tumors from 500-3000 $\text{mm}^3$ inhibit growth of metastases, 1500 $\text{mm}^3$ is the largest size primary tumor that can be safely resected with high survival and without local regrowth. After 21 days, all mice are sacrificed and autopsied.

Lungs are removed and weighed. Lungs are fixed in Bouin's solution and the number of visible metastases is recorded. The diameters of the metastases are also measured using a binocular stereoscope equipped with a micrometer-containing ocular under 8× magnification. On the basis of the recorded diameters, it is possible to calculate the volume of each metastasis. To determine the total volume of metastases per lung, the mean number of visible metastases is multiplied by the mean volume of metastases. To further determine metastatic growth, it is possible to measure incorporation of $^{125}$IdUrd into lung cells (Thakur, M L et al., *J Lab Clin Med* 89:217-28 (1977). Ten days following tumor amputation, 25 µg of fluorodeoxyuridine is inoculated into the peritoneums of tumor-bearing (and, if used, tumor-resected mice). After 30 min, mice are given 1 µCi of $^{125}$IdUrd (iododeoxyuridine). One day later, lungs and spleens are removed and weighed, and a degree of $^{125}$IdUrd incorporation is measured using a gamma counter.

In mice with footpad tumors, when tumors reach about 8-10 mm in diameter, mice are randomized into two groups: (1) legs with tumors are amputated after ligation above the knee joints; or (2) mice are left intact as nonamputated tumor-bearing controls. (Amputation of a tumor-free leg in a tumor-bearing mouse has no known effect on subsequent metastasis, ruling out possible effects of anesthesia, stress or surgery). Mice are killed 10-14 days after amputation. Metastases are evaluated as described above. Statistics: Values representing the incidence of metastases and their growth in the lungs of tumor-bearing mice are not normally distributed. Therefore, non-parametric statistics such as the Mann-Whitney U-Test may be used for analysis.

Study of this model by Gorelik et al. (1980, supra) showed that the size of the tumor cell inoculum determined the extent of metastatic growth. The rate of metastasis in the lungs of operated mice was different from primary tumor-bearing mice. Thus in the lungs of mice in which the primary tumor had been induced by inoculation of larger doses of 3LL cells ($1-5\times10^6$) followed by surgical removal, the number of metastases was lower than that in nonoperated tumor-bearing mice, though the volume of metastases was higher than in the nonoperated controls. Using $^{125}$IdUrd incorporation as a measure of lung metastasis, no significant differences were found between the lungs of tumor-excised mice and tumor-bearing mice originally inoculated with $10^6$ 3LL cells. Amputation of tumors produced following inoculation of $10^5$ tumor cells dramatically accelerated metastatic growth. These results were in accord with the survival of mice after excision of local tumors. The phenomenon of acceleration of metastatic growth following excision of local tumors had been repeatedly observed (for example, see U.S. Pat. No. 5,639,725). These observations have implications for the prognosis of patients who undergo cancer surgery.

F. Bioluminescence Imaging (BLI) of Cell Proliferation in a Mouse Glioma Model

This model has been described by Uhrbom et al, *Nature Medicine* 10:1257-60 (2004). See also: Becher, O J and Holland, E C, *Cancer Res* 2006; 66:3355-9 (2006), which reference are hereby incorporated by reference in their entirety. BLI has previously been used to monitor the formation of grafted tumors in vivo and measure cell number during tumor progression and response to therapy. The development and optimization of successful cancer therapy strategies may well require detailed and specific assessment of biological processes in response to mechanistic intervention. This model uses BLI to monitor the cell cycle in a genetically engineered, histologically accurate model of glioma in vivo. In these platelet-derived growth factor (PDGF)-driven oligodendrogliomas, G1 cell-cycle arrest is generated by blockade of either the PDGF receptor or mTOR using small-molecule inhibitors. Generation of Ef-luc and Ef-luc N-tv-a transgenic mice. A 1714-bp SmaI-XbaI fragment of the pGL3-Basic vector encoding a modified firefly luciferase (Promega) is cloned into a plasmid behind a 273-bp PCR-generated fragment of the human E2F1 promoter. The PCR primers used are E2F1-1 and E2F1-2; an EcoRI site is added at each end of the E2F1 promoter (see Uhrbom et al., supra, for their nucleotide sequences as well as the primers below).

The gene encoding luciferase is followed by a polyadenylation sequence. In the development of this model, chimeric founder mice were generated by pronuclear microinjection of the linearized Ef-luc construct into fertilized FVB oocytes. Genotyping of transgenic mice was done by PCR using primers E2F1-1 and EFLUC-1, yielding a product of 335 bp. EFLUC-positive mouse lines were screened for correct expression of the transgene in vitro. 10 chimera thunders were identified that led to 8 founders with germline transmission; three of these showed tight cell-cycle regulation of expression in vitro. The luciferase activity is measured in primary cultured cells obtained from the brains of newborn mice (see: Dai, C al. *Genes Dev.* 15:1913-25 (2001). Equal numbers of cells are cultured in the presence of 10% fetal bovine serum for 1 d or in 0.5% fetal bovine serum for 4 d before lysis. Luciferase activity is measured using the Luciferase Assay System (Promega) according to the manufacturer's protocol.

Generation of Mouse Brain Tumors.

Double-transgenic neonatal Ef-luc N-tva mice were injected intracranially with 1 µl DF-1 cells producing RCAS-PDGFB retrovirus (see: Shih A H et al., *Cancer Res.* 64:4783-9 (2004); Shih A H and Holland E C, *Cancer Lett.* 232:139-47 (2006)). Mice are monitored carefully for symptoms of tumor development (hydrocephalus, lethargy). All injected mice are routinely screened with BLI, and image-positive mice are followed over time, treated and followed over time, or killed.

BLI of Ef-luc N-tv-a Mice.

Mice are anesthetized with 3% isofluorane before retroorbital injection with 75 mg/kg body weight n-Luciferin (Xenogen). Three minutes after injection of the n-Luciferin, images are acquired for 2 min with, for example, the Xenogen IVIS system (Xenogen) using Living Image™ analysis and acquisition software (Xenogen). A photographic image is taken, onto which the pseudocolor image representing the spatial distribution of photon counts is projected. A circular region has been defined between the ears that is conveniently used as a standard across experiments. From this region the photon counts are compared between different mice.

Drug Treatment of Tumor Bearing Ef-luc N-tv-a Mice.

Image-positive Ef-luc N-tv-a mice are treated daily with the test or control compound at several concentrations, e.g., 100 mg/kg body weight or 40 mg/kg body weight, or are given buffer only for the indicated number of days. All doses are preferably administered through intraperitoneal injection. Commonly, there are 5 mice per treatment condition. Transgenic images may be taken 24-144 h after initiation of treatment. The stock solution of the test compound may be stored frozen −20° C.

Histological Analysis, Immunohistochemistry and TUNEL Analysis.

Brains of killed mice are removed, fixed in formalin and embedded in paraffin. Immunohistochemical stainings are performed using antibodies for PCNA (Oncogene), caspase-3 (Cell Signaling), Ki-67 (Novacastra), and histone H3 (Upstate). TUNEL analysis (Roche) is performed according to the manufacturer's protocol.

G. Corneal Angiogenesis Model

The protocol used is essentially identical to that described by Volpert et al. (*J. Clin. Invest.* 98:671-679 (1996)). Briefly, female Fischer rats (120-140 gms) are anesthetized and pellets (5 µl) comprised of Hydron®, bFGF (150 nM), and the compounds to be tested are implanted into tiny incisions made in the cornea 1.0-1.5 mm from the limbus. Neovascularization is assessed at 5 and 7 days after implantation. On day 7, animals are anesthetized and infused with a dye such as colloidal carbon to stain the vessels. The animals are then euthanized, the corneas fixed with formalin, and the corneas flattened and photographed to assess the degree of neovascularization. Neovessels may be quantitated by imaging the total vessel area or length or simply by counting vessels.

H. Matrigel® Plug Assay

This assay is performed essentially as described by Passaniti et al. (*Lab Invest.* 67:519-528 (1992). Ice-cold Matrigel® (e.g., 500 µL) (Collaborative Biomedical Products, Inc., Bedford, Mass.) is mixed with heparin (e.g., 50 µg/ml), FGF-2 (e.g., 400 ng/ml) and the compound to be tested. In some assays, bFGF may be substituted with tumor cells as the angiogenic stimulus. The Matrigel® mixture is injected subcutaneously into 4-8 week-old athymic nude mice at sites near the abdominal midline, preferably 3 injections per mouse. The injected Matrigel® forms a palpable solid gel. Injection sites are chosen such that each animal receives a positive control plug (such as FGF-2+heparin), a negative control plug (e.g., buffer+heparin) and a plug that includes the compound being tested for its effect on angiogenesis, e.g., (FGF-2+heparin+compound). All treatments are preferably run in triplicate. Animals are sacrificed by cervical dislocation at about 7 days post injection or another time that may be optimal for observing angiogenesis. The mouse skin is detached along the abdominal midline, and the Matrigel® plugs are recovered and scanned immediately at high resolution. Plugs are then dispersed in water and incubated at 37° C. overnight. Hemoglobin (Hb) levels are determined using Drabkin's solution (e.g., obtained from Sigma) according to the manufacturers' instructions. The amount of Hb in the plug is an indirect measure of angiogenesis as it reflects the amount of blood in the sample. In addition, or alternatively, animals may be injected prior to sacrifice with a 0.1 ml buffer (preferably PBS) containing a high molecular weight dextran to which is conjugated a fluorophore. The amount of fluorescence in the dispersed plug, determined fluorimetrically, also serves as a measure of angiogenesis in the plug. Staining with mAb anti-CD31 (CD31 is "platelet-EC adhesion molecule or PECAM") may also be used to confirm neovessel formation and microvessel density in the plugs.

I. Chick Chorioallantoic Membrane (CAM) Angiogenesis Assay

This assay is performed essentially as described by Nguyen et al. (*Microvascular Res.* 47:31-40 (1994)). A mesh containing either angiogenic factors (bFGF) or tumor cells plus inhibitors is placed onto the CAM of an 8-day old chick embryo and the CAM observed for 3-9 days after implantation of the sample. Angiogenesis is quantitated by determining the percentage of squares in the mesh which contain blood vessels.

J. In Vivo Assessment Angiogenesis Inhibition and Anti-Tumor Effects Using the Matrigel® Plug Assay with Tumor Cells In this assay, tumor cells, for example $1-5 \times 10^6$ cells of the 3LL Lewis lung carcinoma or the rat prostate cell line Mat-LyLu, are mixed with Matrigel® and injected into the flank of a mouse following the protocol described in Sec. B above. A mass of tumor cells and a powerful angiogenic response can be observed in the plugs after about 5 to 7 days. The anti-tumor and anti-angiogenic action of a compound in an actual tumor environment can be evaluated by including it in the plug. Measurement is then made of tumor weight, Hb levels or fluorescence levels (of a dextran-fluorophore conjugate injected prior to sacrifice). To measure Hb or fluorescence, the plugs are first homogenized with a tissue homogenizer.

Having now generally described the invention, the same will be more readily understood through reference to the following examples which are provided by way of illustration, and are not intended to be limiting of the present invention, unless specified.

EXAMPLE I

Structure-Activity Relationship-Based Discovery of Novel Compound and their Effects on Cells and Animals Infected with Herpes Simplex Virus-Type 1 (HSV-1)

These new compounds, discovered using SAR analysis as described above, and resveratrol were evaluated for their cytotoxicity against HSV-1 infected Vero cells and mice infected with HSV-1

Results summarized in Table 11 shows the cytotoxicity of the compounds to HSV-1 infected cells as the cytopathic or cytotoxic dose-50 ($CD_{50}$) the dose at which 50% of the target cells are killed, as well as the log $CD_{50}$ after 48 hours of exposure.

NAB group 32 contains two compounds, Tolan-2 (also designated herein as KST-201) and Stil-2. Based on the NAB, they were classified as topological isomers. However, chemically they differ because Stil-2, a dihydrostilbene, contained a double bonded linker, while Tolan-2 contained a triple bonded linker. The cytotoxicity of the two molecules on Vero cells differed markedly: Tolan-2 was less toxic than Stil-2.

NAB group 35 contains resveratrol, a trihydroxystilbene and Tolan-3 (also designated herein as KST-301, a trihydroxytolan. Once again, the two molecules differ chemically because resveratrol has a double bonded linker and Tolan-3 has a triple bonded linker. This tolan was also less toxic than hydroxystilbene.

NAB group 37 contains two molecules, Stil-4 (tetrahydroxystilbene), and Tolan-4 (also designed herein as KST-401), a tetrahydroxytolan. Again the stilbene derivative was more toxic than the tolan derivative. This led the present inventor to conclude that hydroxylated tolans are less toxic to host cells than their corresponding stilbene derivatives.

Once the 50% cytopathic dose ($CD_{50}$) for each polyphenol had been established, the polyphenols were tested for anti-HSV-1 activity at three concentrations corresponding to the $CD_{50}$, 75% of the $CD_{50}$ and 50% of the $CD_{50}$. For this purpose HSV-1 replication at 24, 48 and 72 h was examined in the presence or absence of varying concentrations of the polyphenol.

Treatment of HSV-1-infected Vero cells with Stil-2 and Stil-4 exhibited no substantial reduction in viral replication at the concentrations examined. A substantial viral inhibition occurred after treatment with tolan-4 for 24 h, though by 48 h, viral replication in the treated cells was nearly the same as for untreated controls. HSV-1 viral production in Vero cells was substantially inhibited by Tolan-11 (also designated herein as KST-213) albeit only after 72 hrs exposure. Both Tolan-2 and Tolan-3 showed significant anti-HSV activity. it Tolan-2 and Tolan-3 appeared to be more effective in vitro than resveratrol, especially when considering both the cytotoxicity results and those measuring inhibition of HSV-1 replication.

TABLE 11

Structure Activity Relationship of Hydroxytolan Compounds and Comparison to Resveratrol and other Stilbenes

| Name | NAB | Structure | $CD_{50}$ μM | Log $CD_{50}$ |
|------|-----|-----------|--------------|---------------|
| Stil-1 | 31 | 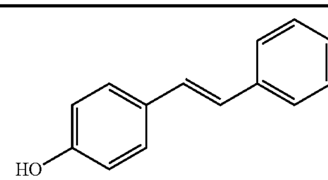 | 131 | 2.12 |
| Stil-2 | 33 | 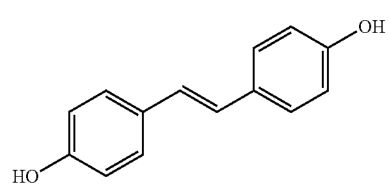 [SMILES: Oc1ccc(/C=C/c2ccc(O)cc2)cc1] | 53.3 | 1.73 |

TABLE 11-continued

Structure Activity Relationship of Hydroxytolan Compounds and Comparison to Resveratrol and other Stilbenes

| Name | NAB | Structure | CD$_{50}$ μM | Log CD$_{50}$ |
|---|---|---|---|---|
| Tolan-2 | 33 | HO-⌬-C≡C-⌬-OH | 106 | 2.03 |
| Resveratrol | 35 | (3,5-dihydroxyphenyl)-CH=CH-(4-hydroxyphenyl) | 264 | 2.42 |
| Tolan-3 | 35 | HO-⌬-C≡C-⌬(3,5-diOH) | 350 | 2.54 |
| Stil-4 | 37 | (3,5-diOH-phenyl)-CH=CH-(3,5-diOH-phenyl) | >200 | 2.30 |
| Tolan 4 | 37 | (3,5-diOH-phenyl)-C≡C-(3,5-diOH-phenyl) | 103 | 2.01 |
| Tolan 11 | 39 | HO-⌬-C≡C-⌬-CF$_3$ | 48.2 | 1.68 |

A 130-fold decrease in viral titer was observed at a concentration of 75 μM Tolan-2 after 48 h. Viral inhibition was greatest in HSV-1 infected cells treated with Tolan-3—a 55,000-fold reduction in viral titer by 175 μM Tolan-3 after 48 h. Tolan-3 activity persisted through 72 hrs. Tolan-2 and Tolan-3 exhibited greater inhibition at lower concentrations than did resveratrol. Of all the polyphenols tested, Tolan-3 showed the strongest inhibition of HSV-1 (Tables 12-14).

Because Tolan-2 and Tolan-3 appeared to be the most promising compounds vs resveratrol, a direct comparison was conducted. Comparison of the selectivity index (SI) of resveratrol, Tolan-2 and Tolan-3 was done. The SI is the ratio of the CD$_{50}$ divided by a selected inhibitory concentration (IC %). The larger the SI value, the more active the compound. The IC's selected for resveratrol, Tolan-2 and Tolan-3 were the concentration at which 50% of HSV-1 replication was inhibited. The IC$_{50}$ of resveratrol, Tolan-2 and Tolan-3 were determined in viral assays performed at lower compound concentrations. The IC$_{50}$ for Tolan-2 was 15.6 μM. The IC$_{50}$ for Tolan-3 was 6.37 μM and the IC$_{50}$ for resveratrol was 23.4 μM. The SI$_{50}$ for resveratrol, Tolan-2 and Tolan-3 were calculated 48 h post-infection. The SI$_{50}$ was 9.3 for resveratrol, 6.8 for Tolan-2 and >63 for Tolan-3. Thus Tolan-3 was the most active of the polyphenols tested and was therefore selected for further detailed studies.

TABLE 12

Anti-HSV-1 Activity of Polyphenols Tested at 50% of their CD$_{50}$

| Compound | Concentration tested (μM) | Fold-Reduction in Viral Replication Hours Post-Infection | | | Anti-HSV-1 Activity |
|---|---|---|---|---|---|
| | | 24 | 48 | 72 | |
| Stil-2 | 35 | 1.8 | 1.6 | 1.6 | − |
| Stil-4 | 100 | 2.3 | 0.3 | 0.7 | − |
| Tolan-2/KST-201 | 50 | 20 | 8.6 | 20 | + |
| Tolan-3/KST-301 | 175 | 3,700 | 55,000 | 79,000 | + |

TABLE 12-continued

Anti-HSV-1 Activity of Polyphenols Tested at 50% of their $CD_{50}$

| Compound | Concentration tested (μM) | Fold-Reduction in Viral Replication Hours Post-Infection | | | Anti-HSV-1 Activity |
|---|---|---|---|---|---|
| | | 24 | 48 | 72 | |
| Tolan-4/KST-401 | 77 | 13 | 2.1 | 1.6 | – |
| Tolan-11/KST-213 | 24 | 2.8 | 3.7 | 3.8 | – |

To determine whether Tolan-3 directly inactivated the virus, Tolan-3 was incubated with HSV-1 at room temperature for 1, 30 or 60 minutes while controls were also incubated with HSV-1 at room temperature without Tolan-3. The treated or control virus was plated onto Vero cells. Tolan-3 did not directly inactivate HSV-1 during the 60 minute incubation. In addition, Tolan-3 treatment did not inhibit HSV-1 attachment or penetration.

TABLE 13

Anti-HSV-1 Activity of Polyphenols at 75% of the $CD_{50}$

| Compound | Concentration tested (μM) | Fold Reduction in Viral Replication Hours Post-Infection | | | Anti-HSV-1 Activity |
|---|---|---|---|---|---|
| | | 24 | 48 | 72 | |
| Stil-2 | 52.5 | 2.2 | 2.1 | 1.6 | – |
| Stil-4 | 150 | 2.4 | 0.3 | 1.5 | – |
| Tolan-2/KST-201 | 75 | 380 | 130 | 950 | + |
| Tolan-3/KST-301 | 263 | 26,000 | 43,000 | 2,200,000 | + |
| Tolan-4/KST-401 | 103 | 60 | 1.4 | 1.7 | +/− |
| Tolan-11/KST-213 | 36 | 5.7 | 43 | 1,400 | −/+ |

Together these results suggested that the antiviral effects of Tolan-3 are a result of its effects on cells (not the virus). Viral inhibition by Tolan-3 appeared to occur after viral entry into cells. To determine whether the antiviral effect was the result of cytotoxicity HSV-1 infected cell were treated with 350 μM Tolan-3 for 24 h. Subsequently, the compound was removed and replaced with culture medium alone, and the incubated continued for 48 or 72 more hrs. In a second experiment, HSV-1 infected Vero cells were incubated with 350 μM Tolan-3 for 48 h. Thereafter, the Tolan-3 was removed and replaced by medium and the incubation continued for an additional 24 h. Viral titers were calculated by a standard plaque assay.

The reversibility studies showed that HSV-1 replication recovered if Tolan-3 was removed from infected Vero cells as late as 48 hours post infection (FIG. 1). Thus, the inhibitory effect not directly due to host cell cytotoxicity; infectious viral particles were still present in the treated samples.

Finally, these results corroborate the conception that Tolan-3 (and the other compounds of the present invention) affecting the host cells not the virus. Since Tolan-3 treatment was shown to induce a transient block in $G_2$/M phase of the cell cycle, subsequent investigations focused on cell cycle gene transcripts.

Evidence for an effect in vivo was sought in a study in which the skin of hairless mice was infected with HSV-1 by scarification (Docherty, J J et al., 2004, *Antiviral Res.* 61:19-26) and was then treated topically with resveratrol or Tolan-3. A 10% w/v solution of resveratrol in DMSO was applied topically to the epidermal infection site 3×/day for 5 days; this significantly reduced the severity of the lesions when compared to untreated controls animals treated with the DMSO vehicle. The lesions were scored as in the description for FIG. 2.

Control animals had a maximum average lesion score of 3.8-4 by days 8 and 9, while treated animals had a maximum lesion score of 0.8-1.2. In addition, 83-100% of untreated or vehicle treated animals developed HSV infections, while only 43% of resveratrol-treated animals showed any evidence of infection. Therefore, a topical 10% resveratrol (w/v) solution applied to the infected area reduced the severity of HSV-1 lesions in vivo and prevented lesion formation in 57-67% of the treated animals.

Figure 2:
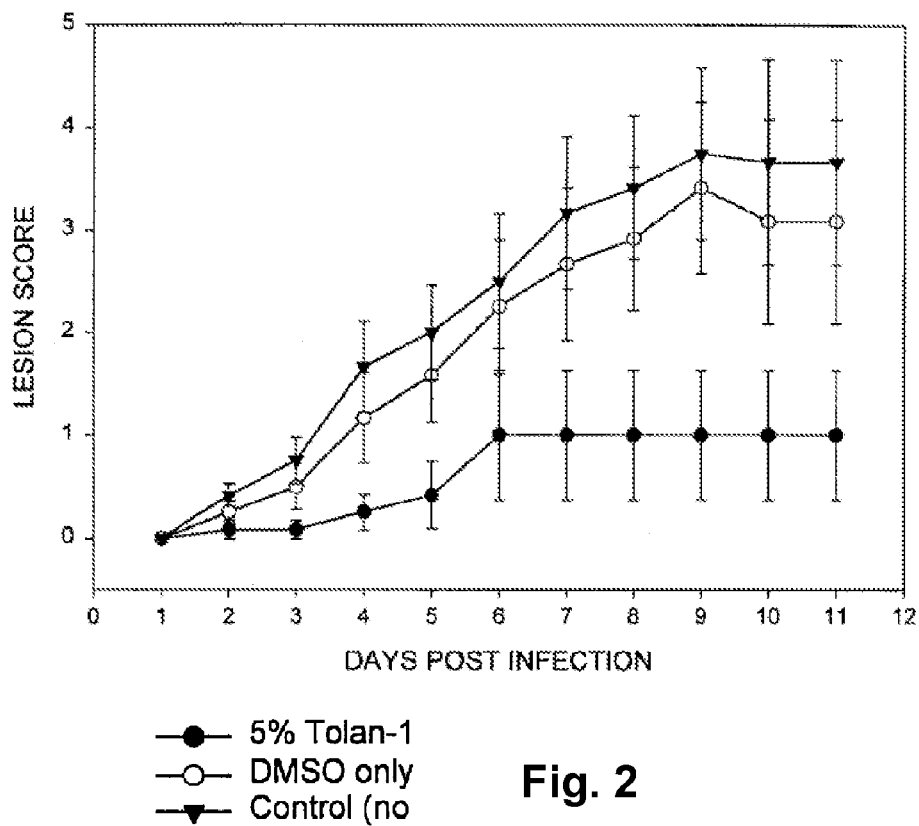
FIG. 2. HSV-1-induced Lesion Development: Treatment with 10% w/v KST-301/Tolan-3. A 10% w/v solution of KST-301 in DMSO was applied topically to the epidermal infection site 3×/day for 5 days. Controls animals received the same volume of the DMSO vehicle at the same intervals. Lesions were scored as 0=no visible lesions, +1=papules around the infection site, +2=papules are ulcerated around the infection site with eschar formation, +3=ulcerated zosteriform spread along peripheral nerves to the flank of the animal, +4=ulcerated lesions open on the flank, and +5=death of the animal.
Figure 3:
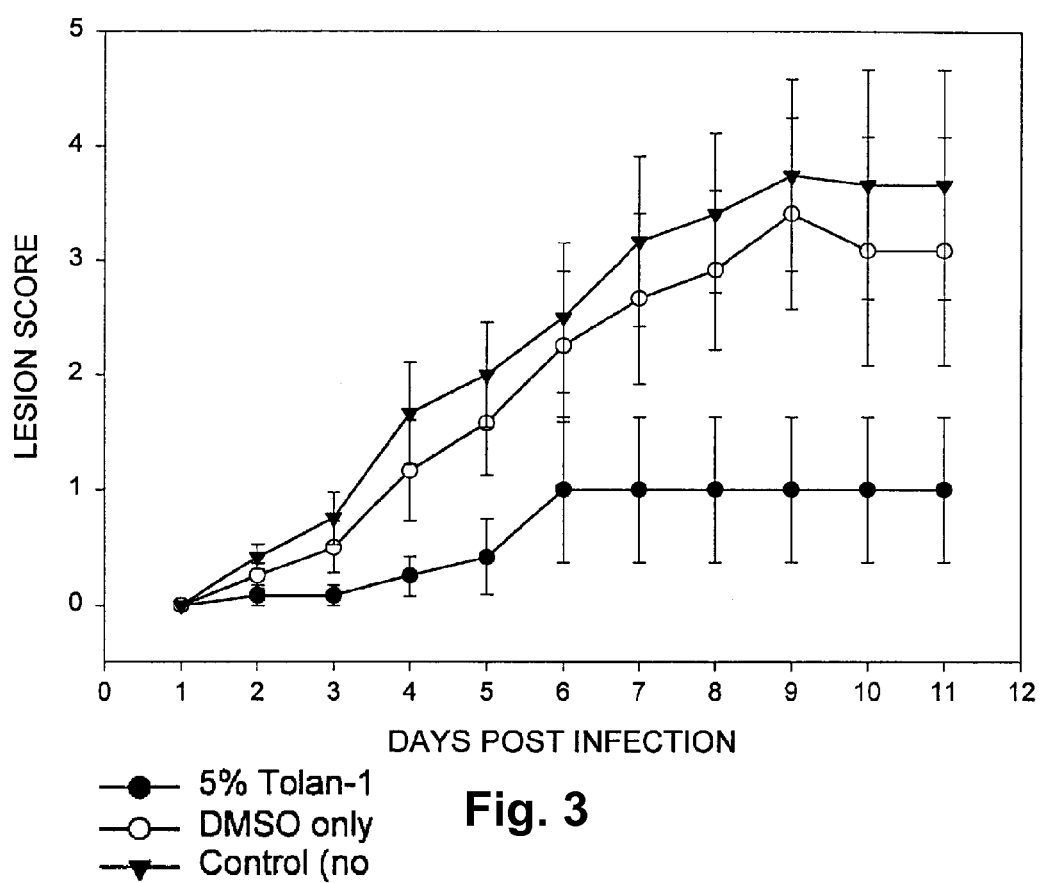
FIG. 3. HSV-1-induced Lesion Development: Treatment with 5% w/v KST-301/Tolan-3. A 5% solution of KST-301 was applied. See description for FIG. 2.

The study was repeated using a 10% w/v solution of Tolan-3 in DMSO (FIG. 2). Severity of the HSV lesions was significantly reduced compared to control and vehicle-treated animals. Likewise, an even more dilute solution of Tolan-3, 5% w/v (FIG. 3), significantly reduced the number and severity of HSV lesions. Control animals had maximum average lesion scores of 3.8-4 by days 8 and 9, whereas treated animals had maximum average lesion scores of 0.8-1.2. Whereas 83-100% of the control and vehicle-treated animals developed HSV infections, only 33% of the Tolan-3 treated animals showed evidence of infection. Thus, Tolan-3 not only reduced severity of HSV lesions in vivo, preventing lesions in 67% of the animals, but this compound also inhibited lesion formation at half the concentration of its "progenitor" compound, resveratrol Tolan-3-treated animals showed no apparent dermal toxicity such as erythema, scaling, crusting, lichenification, or excoriation. On the contrary, Tolan-3 treatment appeared to facilitate lesion healing.

One of the primary conclusions of the above studies was that the tolan compounds of the present invention acted on cells, specifically here, cells infected with HSV-1 and killed them. This effect translated into in vivo efficacy in treating HSV-1 infection.

EXAMPLE II

Selective Cytotoxicity of Hydroxytolans to Cancer Cells vs. Normal Cells

Comparison to Resveratrol

Because the antiviral activity of the tolans appeared to be due to tolan-induced modulation of the host cell rather than a direct effect on the virus, the present inventor turned his attention to antitumor activity of these compounds.

As a first step, the antitumor activity of the tolans was assessed against a panel of three cancer cells lines that produce solid tumors upon implantation into animals. DU145 is an androgen-independent prostate cancer cells. T24 is a transitional cell bladder carcinoma cell. MDAH2274 ("MDAH") is an endometroid ovarian adenocarcinoma cell. To assess the selectivity of this antitumor activity, the toxicity of the tolans to normal human fibroblasts (MHRF) was examined. Subsequently, studies with Tolan-3 (KST-201) were expanded to test its action on a wide range of tumor cell lines.

Cell killing was evaluated using the colorimetric MTT assay. The assay measures the formation of a colored product from a chromogenic precursor, the tetrazole 3-[4,5-dimethylthiazol-2-yl]-2,5 diphenyltetrazolium bromide (MTT). The yellow MTT is reduced to purple formazan in the mitochondria of living cells. A solubilization solution (typically dimethyl sulfoxide or sodium dodecyl sulfate in dilute hydrochloric acid) is added to dissolve the insoluble purple formazan product into a colored solution. The absorbance of this colored solution is quantified by measuring at a certain wavelength (usually between 500 and 600 nm) by a spectrophotometer. The amount of purple formazan product generated is proportional to the number of viable cells (Mosmann, T., 1983, *J. Immunol. Meth.* 65:55-63; Wilson, A. P., *Cytotoxicity and Viability Assays*. In: *Animal Cell Culture: A Practical Approach,* 3rd ed. (Masters, J R W, ed.) Oxford University Press: Oxford, Vol. 1, pp. 175-219. 2000). This MTT assay is used widely to assess the cytotoxicity and selectivity of compounds such as anti-cancer drugs. The assay is suitable for rapid toxicity characterization of a test agent such as a drug formulation. One way of assigning a cytotoxic activity to an agent is by converting the raw date to a $CD_{50}$ value, which represent the amount (dose) of the agent needed to achieve 50% of the maximal cytotoxic activity. A lower $CD_{50}$ indicates a greater cytotoxic activity (as a lower amount of the agent is needed to achieve a fixed level of cytotoxicity). Two agents can be compared by examining the fold-increase or decrease in their $CD_{50}$ values.

The results are shown in Table 14 below. When normal human fibroblasts (MHRF) were exposed to resveratrol for 1, 2 or 3 days, the doses that resulted in 50% cytotoxicity ($CD_{50}$) ranged from 155 μM for a 1-day exposure, to 44 μM for a 3-day exposure.

For human prostate cancer cells of the DU145 line, the $CD_{50}$ values ranged from 92 μM to 28 μM. For human bladder cancer cells (T24) and ovarian cancer cells (MDAH2274), the $CD_{50}$ values ranged from 36 μM to 23 μM and from 37 μM to 15 μM, respectively.

Thus, resveratrol was 1.6 fold more potent against DU145 cells compared to control MHRF fibroblasts. Likewise, this compound was 2-fold and 4-fold more potent in killing T24 and MDAH2274 tumor cells vs. control MHRF fibroblasts.

Normal human fibroblasts (MHRF) and the same three tumor cell lines were exposed to KST-201 (4,4'-dihydroxytolan) for 1, 2 or 3 days and evaluated as above. The results appear in Table 15.

TABLE 14

Cytotoxicity ($CD_{50}$) of Resveratrol

| Incubation Time in days | $CD_{50}$ against cell lines: | | | |
|---|---|---|---|---|
| | MHRF | DU145 | T24 | MDAH |
| 1 | 154.8 ± 16.5 † | 92.2 ± 2.90 | 35.7 ± 1.00 | 36.9 ± 2.45 |
| 2 | 50.9 ± 0.6 | 58.2 ± 0.40 | 29.1 ± 0.05 | 23.1 ± 0.14 |
| 3 | 44.3 ± 3.0 | 27.9 ± 0.65 | 22.6 ± 0.25 | 14.6 ± 0.12 |

† = $CD_{50}$: Resveratrol concentration (μM) giving 550% cytotoxicity determined in an MTT assay.

The $CD_{50}$ on control MHRF fibroblasts ranged from 299 μM (1-day exposure) to 153 μM (3-day exposure). For DU145 human prostate cancer cells, the $CD_{50}$ values ranged from 57 μM to 9.4 μM. The $CD_{50}$ values for bladder cancer (T24) and ovarian cancer (MDAH2274) ranged from 83 μM to 8.5 μM and from 22 μM to 3.1 μM.

The results showed that hydroxytolan was 16-fold more potent against DU145 prostate cancer cells compared to control MHRF fibroblasts. Likewise, hydroxytolan was 18-fold more active in killing T24 bladder cancer cells and 50-fold more active in killing MDAH 2274 ovarian cancer cells (vs. fibroblasts).

TABLE 15

Cytotoxicity ($CD_{50}$) of Hydroxytolan KST-201

| Incubation Time (days) | $CD_{50}$ against cell lines: | | | |
|---|---|---|---|---|
| | MHRF | DU145 | T24 | MDAH |
| 1 | 298.8 ± 3.52 † | 57.3 ± 0.81 | 82.6 ± 1.62 | 21.5 ± 7.35 |
| 2 | 194.1 ± 9.60 | 16.8 ± 0.63 | 31.1 ± 0.81 | 10.5 ± 2.70 |
| 3 | 153.2 ± 4.40 | 9.4 ± 0.36 | 8.5 ± 0.34 | 3.1 ± 0.12 |

† = $CD_{50}$: Hydroxytolan concentration (μM) giving 50% cytotoxicity determined in an MTT assay.

When comparing the activities of hydroxytolan (Table 15) to resveratrol (Table 14), it is noteworthy that the hydroxytolan was 3.5 fold less toxic to normal fibroblasts than was resveratrol, while being 3-fold more toxic to DU145 prostate cancer cells, 2.8 fold more toxic to T24 bladder cancer cells and 4.7 fold more toxic to MDAH 2274 ovarian cancer cells.

Because of the above tumor-selective cytotoxic effects of the tolan compounds and the successful action in vivo when applied topically to skin, the action of these compounds was expanded to additional tumor cells types. Results are shown in Table 16, below The results indicate that KST-201 was as or more effective than resveratrol, while having less of an effect on normal cells, a desired trait in an anti-cancer drug.

Figure 4:
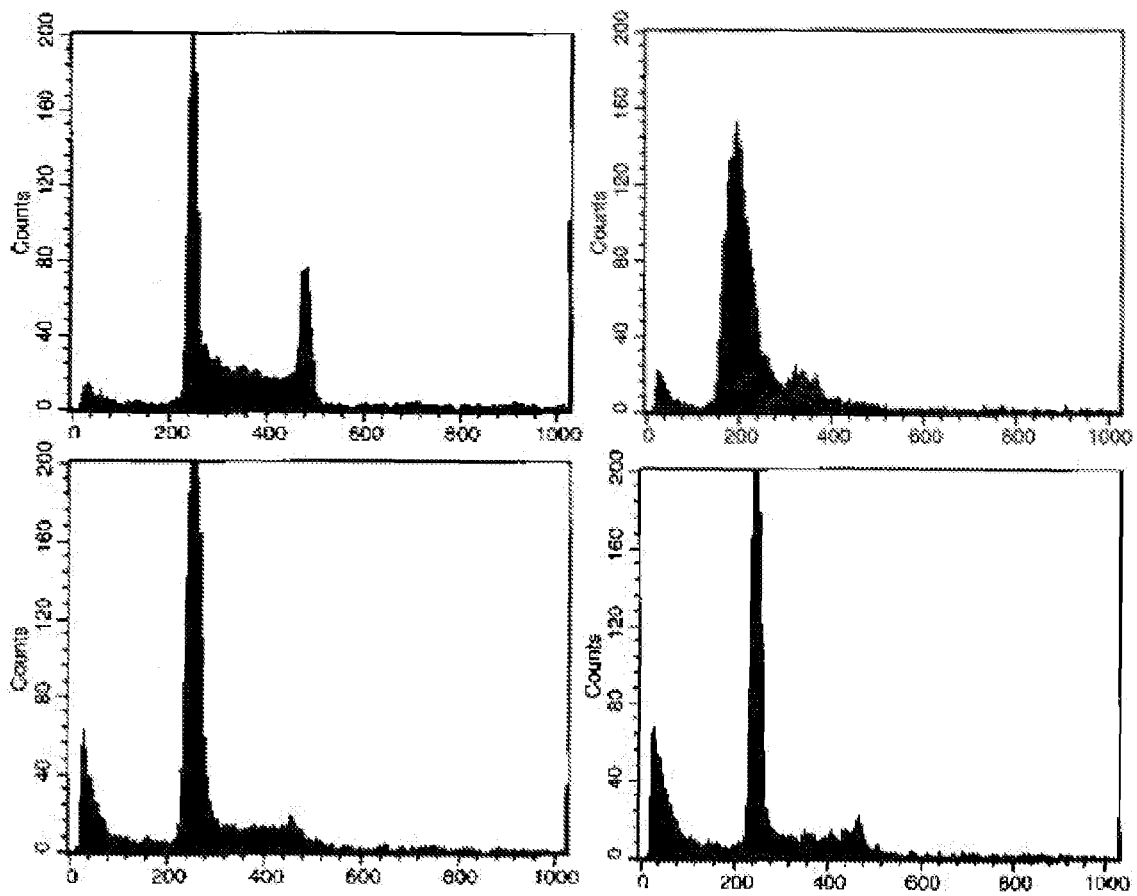
FIG. 4. Flow Cytometric Cell Cycle Analysis of KST-Treated DU145 Cells

Initially, the mechanism(s) responsible for the antitumor activity of KST-201 were tested in the DU145 cell line. Since inhibition of the cycle was shown to be important in the antiviral mechanism of the tolans, the effects of KST-201 treatment on cell cycle progression was studied. Results are shown in FIG. 4 and summarized in Table 17.

TABLE 16

$CD_{50}$ Cytopathic Doses of Resveratrol and KST-201 (3 Days)

| Cell Line | Tumor or Cell Type | Resveratrol $CD_{50}$ (μM) | KST-201 $CD_{50}$ (μM) |
|---|---|---|---|
| T24 | Bladder | 157 ± 5.5 | 8.5 ± 0.3 |
| HCT116 | Colon | 94 ± 0.1 | 129 ± 4.0 |
| HT29 | Colon | 163 ± 0.3 | 79 ± 0.8 |
| WiDR | Colon | 142 ± 6.4 | 80 ± 0.9 |
| NCIH460 | Lung | 43 ± 20 | 42 ± 2.0 |
| A375 | Melanoma | 19 ± 0.2 | 4.6 ± 0.1 |
| MeWo | Melanoma | 185 ± 3.7 | 156 ± 2.5 |
| SKMEL28 | Melanoma | 69 ± 1.2 | 82 ± 10 |
| MHRF | Normal Fibroblasts | 47 ± 6.0 | 153 ± 4.4 |

The cell cycle distribution of sham-treated (FIG. 4, upper left) DU145 cells or DU145 cells treated with KST-201 at 14 μM (FIG. 4, upper right), 28 μM (FIG. 4, lower left) or 56 μM (FIG. 4, lower right) were determined by flow cytometry.

TABLE 17

Cell Cycle Analysis of KST-201 treated
DU 145 Cells by Flow Cytometry

| KST-201 (µM) | Phase of Cell Cycle | | |
|---|---|---|---|
| | $G_0/G_1$ | S | $G_2/M$ |
| 0 | 46 | 40 | 14 |
| 14 | 72 | 28 | — |
| 28 | 77 | 20 | 3 |
| 56 | 78 | 18 | 4 |

As was the case with resveratrol, treatment, KST-201 at all 3 doses led to a $G_0/G_1$-S cell cycle arrest. Accumulation of peaks in the sub-$G_0/G_1$ compartment at 28 µM and 56 µM doses are indicative of apoptotic cell death.

Caspase-3 Activity

The proteolytic activity of caspase-3 in DU145 cells, was measured using a fluorimetric immunosorbent enzyme assay kit. DU145 cells ($2 \times 10^7$) were grown in a 60 mm tissue culture dish for 24 hours at 37° C. in 5% $CO_2$ and were treated with resveratrol or KST201. After washing and centrifuging, the cell pellet was collected and incubated with dithiothreitol (DTT) lysis buffer on ice. The cell lysate was then transferred to a centrifuge tube for measurement of proteolytic cleavage by caspase-3 utilizing a fluorimetric immunosorbent enzyme assay kit (Roche, Indianapolis, Ind.). Antibody against caspase-3 was diluted in the coating buffer and immobilized to the surface of 96-well plates followed by washing steps. Compound-treated cell lysates and the untreated controls were added to the plate and incubated for one hour at 37° C. Any caspase-3 in the samples was captured by the immobilized antibody. The caspase-3 enzyme cleaved its fluorogenic substrate Ac-DEVD-AFC when it was added to the wells, resulting in. free fluorescent AFC that was measured in a Fluoroskan® Ascent FL plate reader (Thermo, Waltham, Mass.) with a filter set at an excitation/emission of 390 nm/590 nm. The fluorescence intensity was proportional to the concentration of AFC determined by a standard curve, generated by different dilutions of AFC standard included in the kit. The amount of activated caspase-3 in the sample was derived from this curve.

Figure 5:
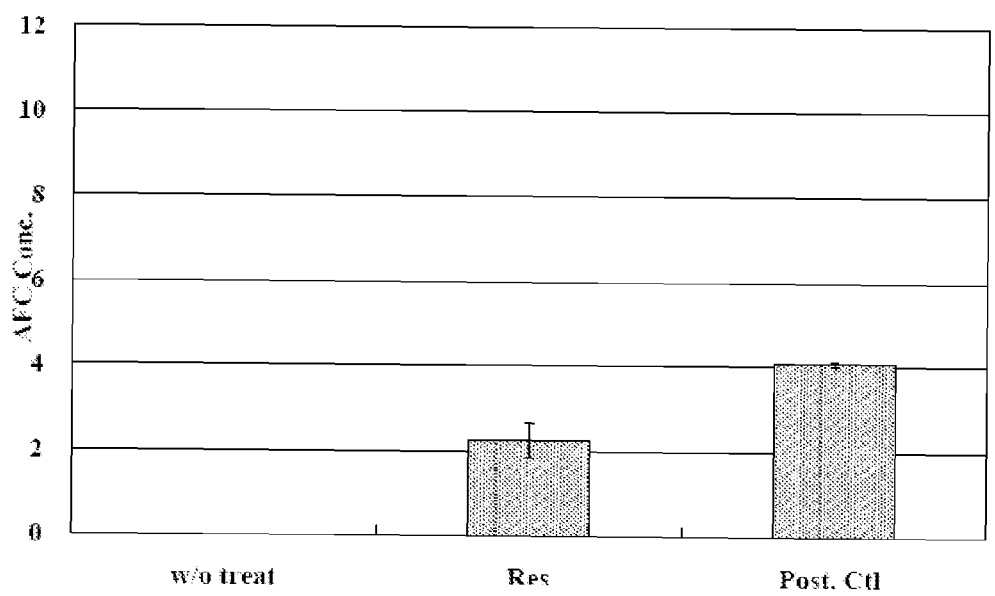
FIG. 5. Measurement of Caspase-3 Activity in Resveratrol-treated DU145 cells. DU145 cells were treated at $CD_{50}$ of resveratrol for 24 hours. Activity of proteolytic cleavage was determined fluorometrically using Ac-DEVD-AFC as a substrate for activated caspase-3 immobilized on the well surface. The results represent mean±SD of triplicate determinations. The positive control ("Post. Ctl") was camptothecin-induced apoptosis in U937 cells.
Figure 6:
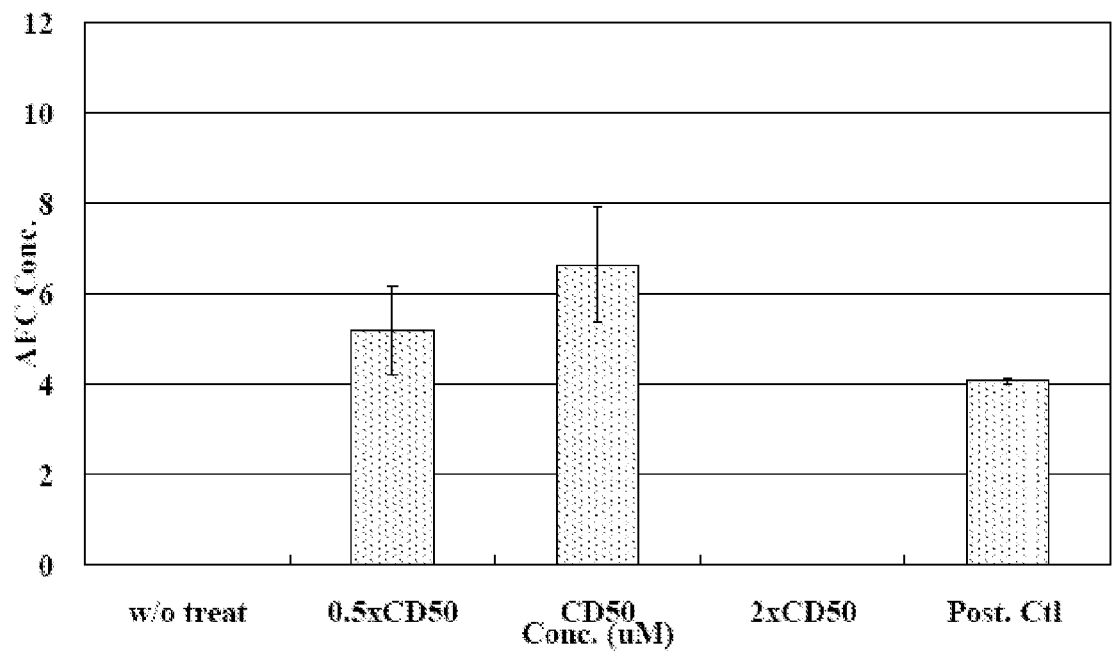
FIG. 6. Measurement of Caspase-3 Activity of KST-201-treated DU145 cells as a function of dose. DU145 was treated at 0.5-fold $CD_{50}$, $CD_{50}$ and 2-fold $CD_{50}$ of KST201 for 24 hours. Activity of proteolytic cleavage (caspase-3 activity) and other details are as above.
Figure 7:
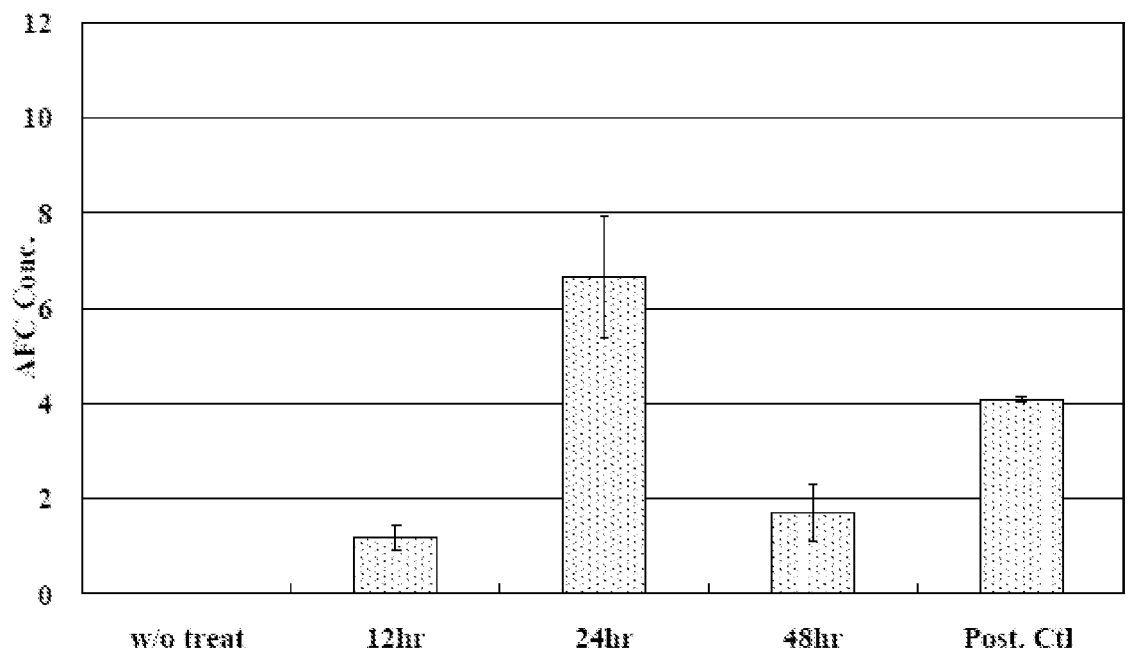
FIG. 7. Time course of Caspase-3 Activation by KST201 in DU145 cells as a measure of apoptosis. DU145 cells were treated at $CD_{50}$ of KST201 for 12, 24 or 48 hours. Details are as described for FIG. 5.

Apoptotic activity of resveratrol (FIG. 5) and KST-201 (FIGS. 6 and 7) was measured as caspase-3 activation. Caspase-3 was activated significantly after 24-hr treatment with KST-201 at its $CD_{50}$ concentration. KST201 effectively activated caspase-3 at $0.5 \times CD_{50}$ after 24 hr; increasing duration or concentration to 48 hours or to $2 \times CD_{50}$, respectively, resulted in loss of caspase-3 activity (FIG. 7). The majority of cells apparently passed the early stage of apoptosis rapidly and were undergoing necrosis and degradation of caspase-3 at the later times. Increased of caspase-3 activity was observed after 24 hrs of treatment (FIG. 7). Caspase activation by KST-201 was 2- to 3-fold greater than that observed following resveratrol treatment (see FIG. 5). Compared to resveratrol, KST201 blocked the cell cycle and induced apoptosis at lower concentrations. The induction of cell cycle arrest by KST-201 was consistent with the cell cycle arrest induced by this compound in HSV-1-infected Vero cells described above.

The observed induction of apoptosis suggested a mechanism mediated by the NF-κB pathway. As discussed below, NF-κB is a likely target because of (a) the structural similarity of KST-201 to resveratrol and (b) the anti-inflammatory activities of resveratrol that are believed to be mediated by its inhibition of the NF-κB and AP-1 signaling pathways, their upstream kinases and their downstream targets (including inducible COX2, inducible NOS and MMP9-9. Moreover, the constitutive expression of NF-κB in a large variety of tumor cells is known to suppress apoptosis, thereby maintaining tumor cell viability.

EXAMPLE III

KST-201 Action on NF-κB

The compounds of the present invention may be considered resveratrol analogs. Because resveratrol inhibits NF-κB, several of the preferred compounds of this invention were evaluated for NF-κB activity using an NF-κB p65 activity assay An ELISA kit (Pierce, Rockford, Ill.) was used to detect the active forms of NF-κB p65 by measuring its binding to a consensus DNA sequence. $3 \times 10^6$ prostate cancer cells of the DU145 line were grown in a 60 mm tissue culture dishes for 24 hours at 37° C. and 5% $CO_2$ and were treated with resveratrol or KST201. As controls, untreated cells were prepared under the same conditions. Cells were collected by scraping and incubated in ice-cold RIPA lysis buffer containing 1% NP40, 0.5% sodium deoxycholate, 0.1% SDS and protease inhibitor cocktail. After centrifugation, the supernatant was transferred to a streptavidin-coated 96-well plate. Active p65 in the sample binds to the immobilized DNA molecules.

To ensure the signal specificity, competitive DNA fragments containing a NF-κB binding site were used to prevent the binding of NF-κB to the consensus sequence. A primary antibody specific for p65 and a secondary HRP-conjugated antibody were added to each well sequentially, resulting in an immobilized p65-HRP complex. Unbound antibodies were washed away. A mixture of luminol/enhancer and peroxide solution was added into each well as a chemiluminescent substrate for HRP. The chemiluminescent signal, proportional to the relative amount of active p65 in the sample, was detected using the Fluoroskan Ascent FL plate reader (Thermo, Waltham, Mass.).

Quantification of DNA-Binding Activity of NF-κB p65 in Resveratrol and KST201-Treated DU145 Cells Cell lysates were prepared from DU145 cells treated with resveratrol or KST201 at different concentrations and time points. DNA sequences containing p65-binding site were immobilized to wells of 96-well plates, allowing activated p65 to bind. After washing, the amount of bound p65 was detected and quantified by the above method. The DNA-binding of active p65 was determined by the intensity of chemiluminescence produced by DNA-p65-HRP complex immobilized on well surfaces. The results represent the mean±SD of triplicate determinations. An inhibitor of p65 binding to DNA was added to confirm specificity.

Results

Figure 8:
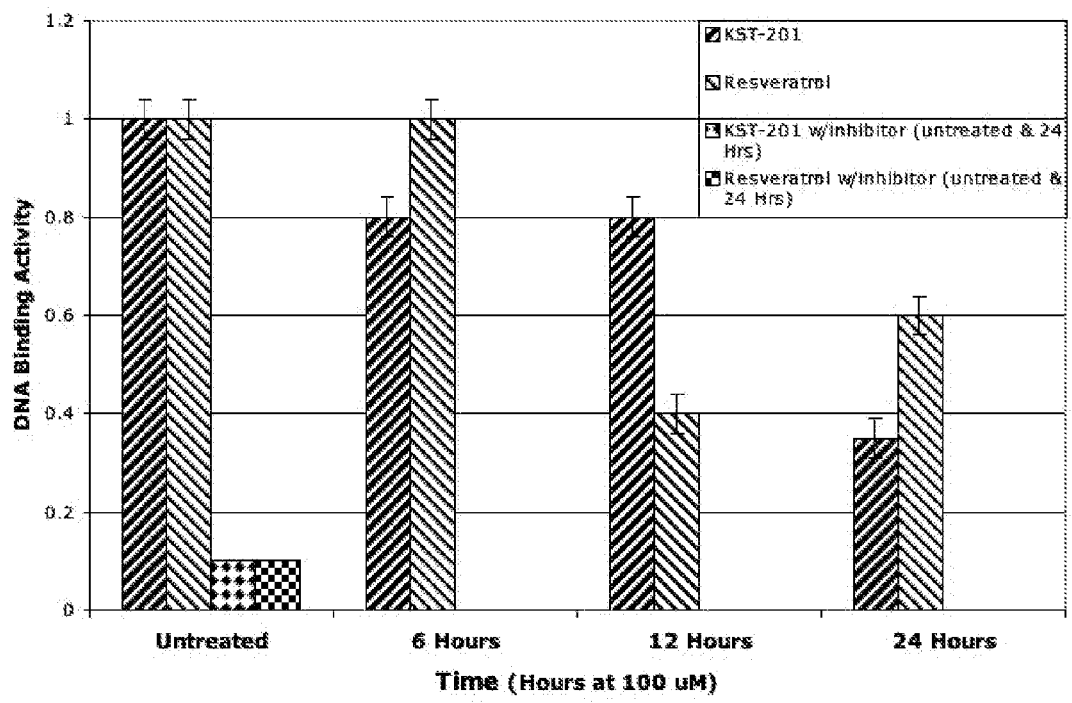
FIG. 8—Effect of KST-201 and Resveratrol on NF-κB Activation (time course). An ELISA kit (Pierce, Rockford, Ill.) was used to detect the active forms of NF-κB p65 by measuring its binding to a consensus DNA sequence. A primary antibody specific for p65 and a secondary horse-radish peroxidase (HRP)-conjugated antibody were used sequentially to produce immobilized p65-HRP complexes. A chemiluminescent substrate for HRP was added and the reaction read using the Fluoroskan Ascent FL plate reader FIG. 9. Effect of KST-201 and Resveratrol on NF-κB Activation (Dose Response). This experiment was carried out as described in the Examples using assay method for FIG. 8.
Figure 9:
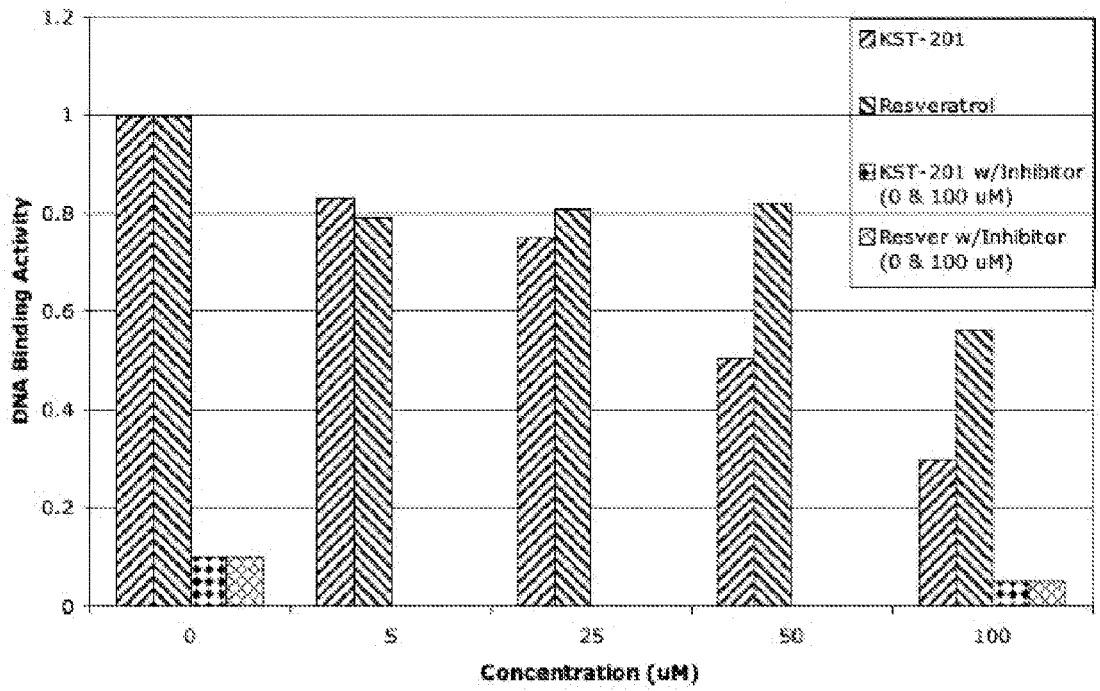

NF-κB was constitutively activated in DU145 cells, and the basal level was measured for normalization of data obtained from treated cells. The results are shown in FIG. 8 (Time course) and FIG. 9 (dose response). Resveratrol slightly influenced the DNA binding activity, which decreased to ~80% of its basal activity after 24-hour treatment at 5, 25 and 50 µM. Remarkably, the DNA binding of p65 was suppressed to 55.3% and 40.2% of its basal activity by 100 µM resveratrol after 12 and 24 hours, respectively. After 24-hour treatment, KST201 was a more effective inhibitor of NF-κB at the concentrations of 50 and 100 µM than resveratrol. Unlike resveratrol, a 12-hour treatment with KST201 was not sufficient to reduce DNA-binding activity of NF-κB (by at least 50%).

The NF-κB p65 activity assay described above was used to investigate NF-κB inhibitory activity of resveratrol and KST201. DU145 cells were treated at 5, 25, 50 and 100 µM of agent for 24 hours.

EXAMPLE IV

Effects of Hydroxytolan Compounds on Cyclooxygenase Enzymes COX-1 and COX-2

The cyclooxygenase (COX) enzymes are also called Prostaglandin H Synthase or PGHSC. COX enzymes have both cyclooxygenase and peroxidase activities. COX catalyzes the first step in the biosynthesis of prostaglandins (PGs), thromboxanes, and prostacyclins; the conversion of arachidonic acid to $PGH_2$. It is now well established that there are two distinct isoforms of COX. Cyclooxygenase-1 (COX-1) is constitutively expressed in variety of cell types and is involved in normal cellular homeostasis. A variety of mitogenic stimuli such as phorbol esters, lipopolysaccharides, and cytokines lead to the induced expression of a second isoform of COX, cyclooxygenase-2 (COX-2). COX-2 is responsible for the biosynthesis of PGs under acute inflammatory conditions (Xie, W et al., 1991, *Proc Natl Acad Sci USA* 88:2692-6). This inducible COX-2 is believed to be the target enzyme for the anti-inflammatory activity of nonsteroidal anti-inflammatory drugs. The COX Inhibitor Screening Assay directly measures $PGF_{2a}$, produced by $SnCl_2$ reduction of COX-derived $PGH_2$.

The prostanoid product can be quantified via enzyme immunoassay (EIA) using a broadly specific antibody that binds to all the major prostaglandin compounds. COX assays from Cayman Chemical, Ann Arbor, Mich., are more accurate and reliable than assays based on peroxidase inhibition. The Cayman COX Inhibitor Screening Assay includes both ovine COX-1 and human recombinant COX-2 enzymes in order to screen isozyme-specific inhibitors. This assay is an excellent tool which can be used for general inhibitor screening.

COX was assayed by measuring production of $PGF_2$, generated by stannous chloride ($SnCl_2$) in the presence of $PGH_2$ using a commercial kit from Cayman Chemical, (Ovine COX Inhibitor Screening Assay, Catalog #560131). See, for example, World Wide Web URL caymanchem.com/app/template/Product.vm/catalog/560131/a/z. Other assays, for example, chemiluminescent and other colorimetric assays from the same manufacturer may be used as alternatives.

This assay measures the production of $PGF_{2a}$, generated by $SnCl_2$, in the presence of $PGH_2$. The initial reactions take place in test tubes at 37° C. The "background" tubes contain reaction buffer mixed with heme. The "100% activity" tubes contain reaction buffer, heme, a known source of the COX enzyme being tested and solvent. In the "sample" tubes, reaction buffer, heme, inhibitor at three concentrations and enzyme are added.

Tubes were incubated for 15 minutes at 37° C. Then the substrate, arachidonic acid, was added and the tubes incubated for 2 minutes. HCl (1M) was used to stop the reaction. Stannous chloride was used to trap the reaction product and reduce it to a more stable form. The tubes were incubated a final time for 5 minutes at room temperature. The contents of the Sample tubes and 100% Activity Tubes were then diluted while the Background tubes were not.

A 96-well plate coated with mouse anti-rabbit IgG was then used and various components were added—assay standards, nonspecific binding controls, maximum binding controls, and the inhibitor dilutions—along with the tracer and antiserum. The plate was incubated at room temperature for 18 hours, washed five times with wash buffer, developed with Ellman's Reagent and the colored reaction product was read on an automatic microplate reader at 410 nm. The $IC_{50}$ for the respective COX enzyme was graphically determined from a three-point curve. For further description of this method, see, for example, Seaver, B et al., (2004). *J. Herbal Pharmacother.* 4:11-18.

Test solutions of resveratrol or KST-201 were mixed with COX1 or COX2, heme, arachidonic acid and saturated $SnCl_2$ solution in tubes were transferred to a 96-well plate as above, and the generation of a colored product followed by colorimetry using Ellman's reagent. The intensity of color was inversely proportional to the amount of free prostaglandins quantitatively representing the COX enzymatic activity, under the influence of the test compounds.

Figure 10:
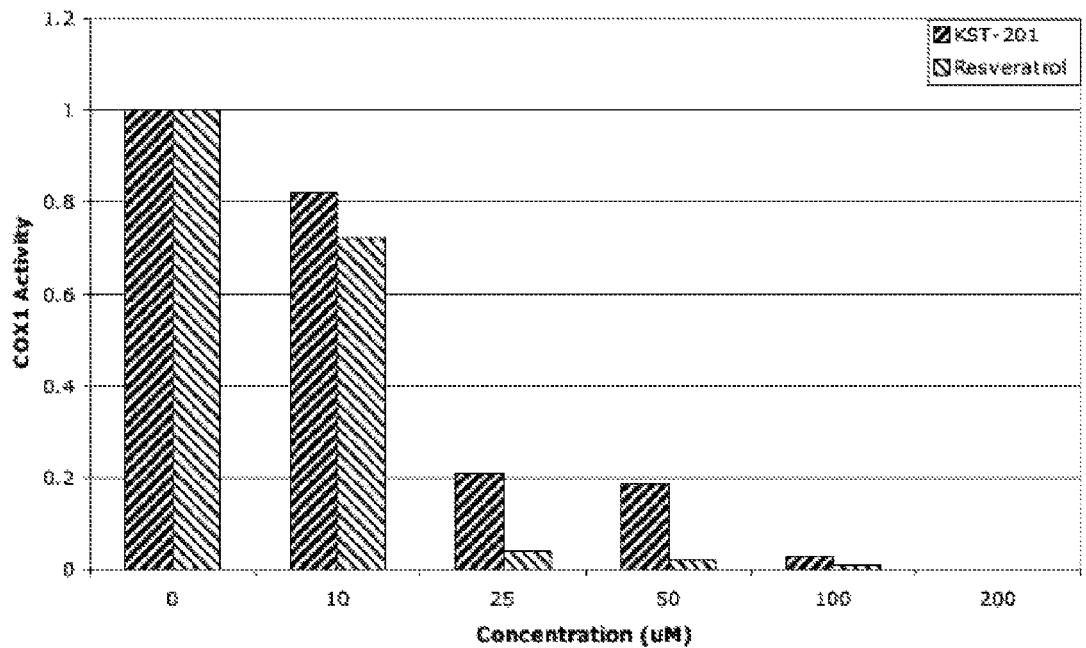
FIG. 10 shows the inhibition of cylooxygenase-1 (COX1) enzyme activity by the hydroxylated tolan compound KST-201 and resveratrol Inhibition of prostaglandin (PG) biosynthesis was evaluated as a decrease in $PGF_{2\alpha}$ as measured by $SnCl_2$ reduction of COX-derived $PGH_2$ produced in the cyclooxygenase reaction. The indicated concentration of these agents were tested in the presence of COX1. COX activity was quantified by measuring the amount of final product $PGF_{2\alpha}$ which competed with acetylcholinesterase (AChE)-linked PGs for binding to its antibody immobilized to the surface of microplate wells. Color was developed by adding an AChE substrate and was inversely related to the amount of $PGF_{2\alpha}$±SD of triplicate determinations.
Figure 11:
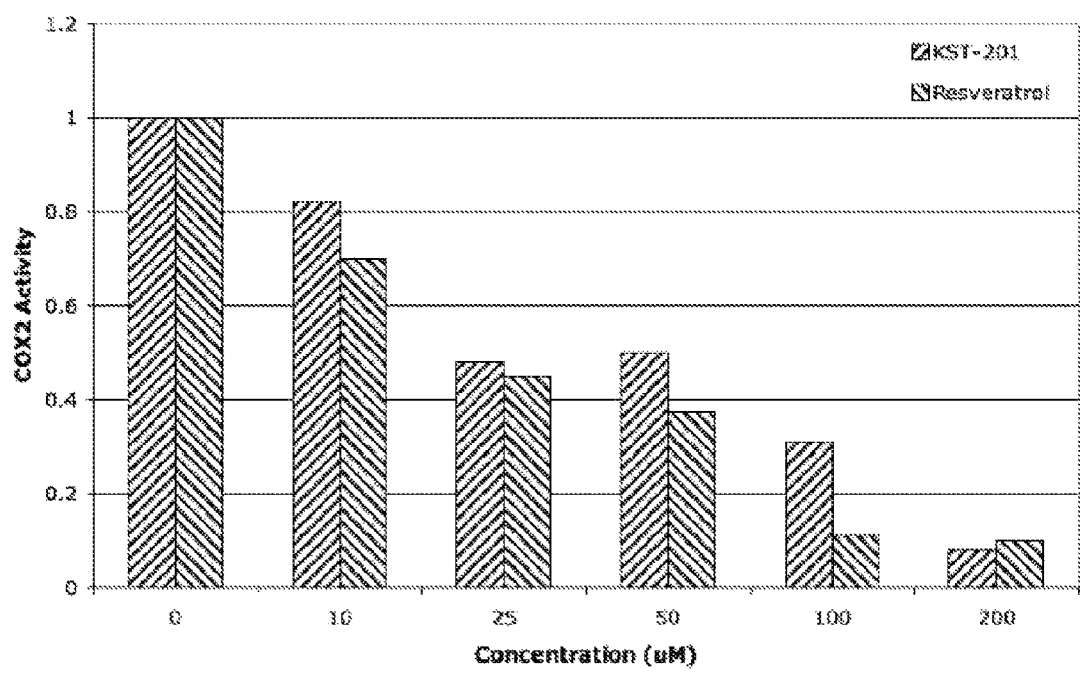
FIG. 11 shows inhibition of cyclooxygenase-1 (COX2) enzyme activity by KST-201 and resveratrol. Inhibition of prostaglandin (PG) biosynthesis was evaluated as above. The indicated concentration of these agents were tested in the presence of COX2. See description of FIG. 10 for details.
Figure 12A:
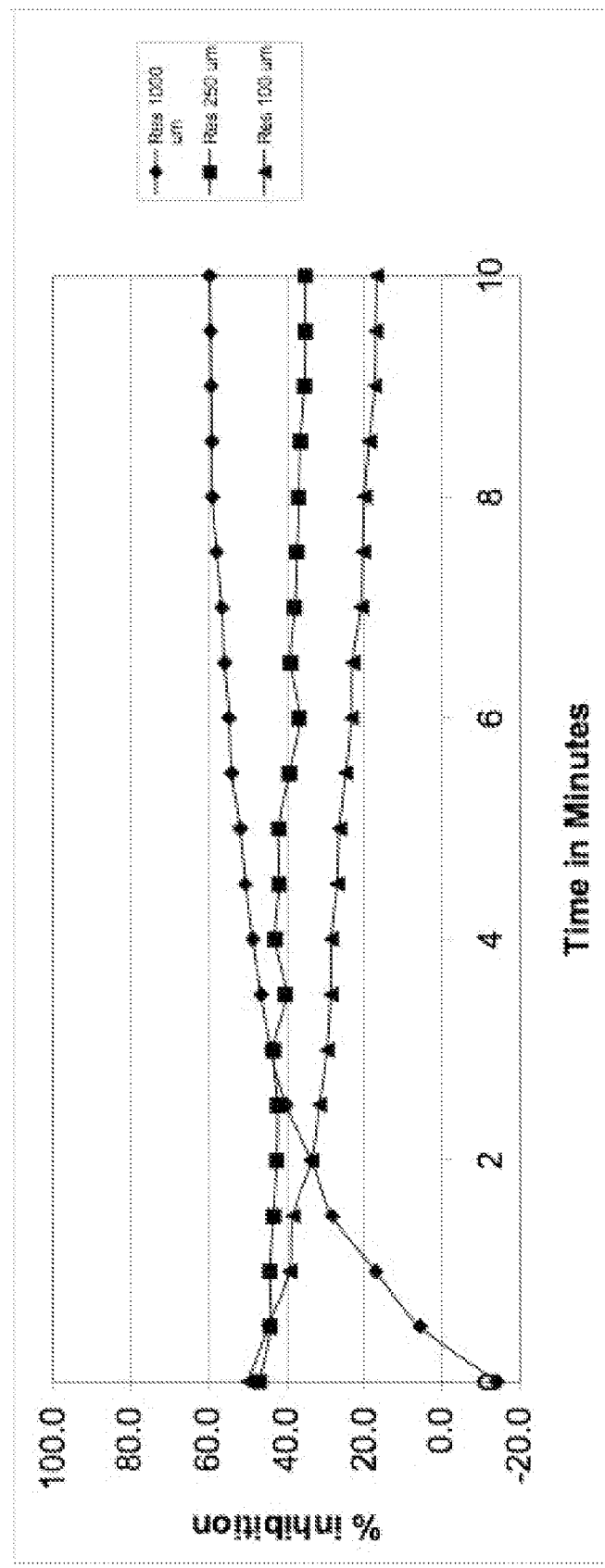
FIG. 12A-12D. Inhibition of mushroom tyrosinase Activity by resveratrol (FIG. 12A), KST-201 (FIG. 12B), KST-301 (FIG. 12C) and, KST-401 (FIG. 12D).
Figure 12B:
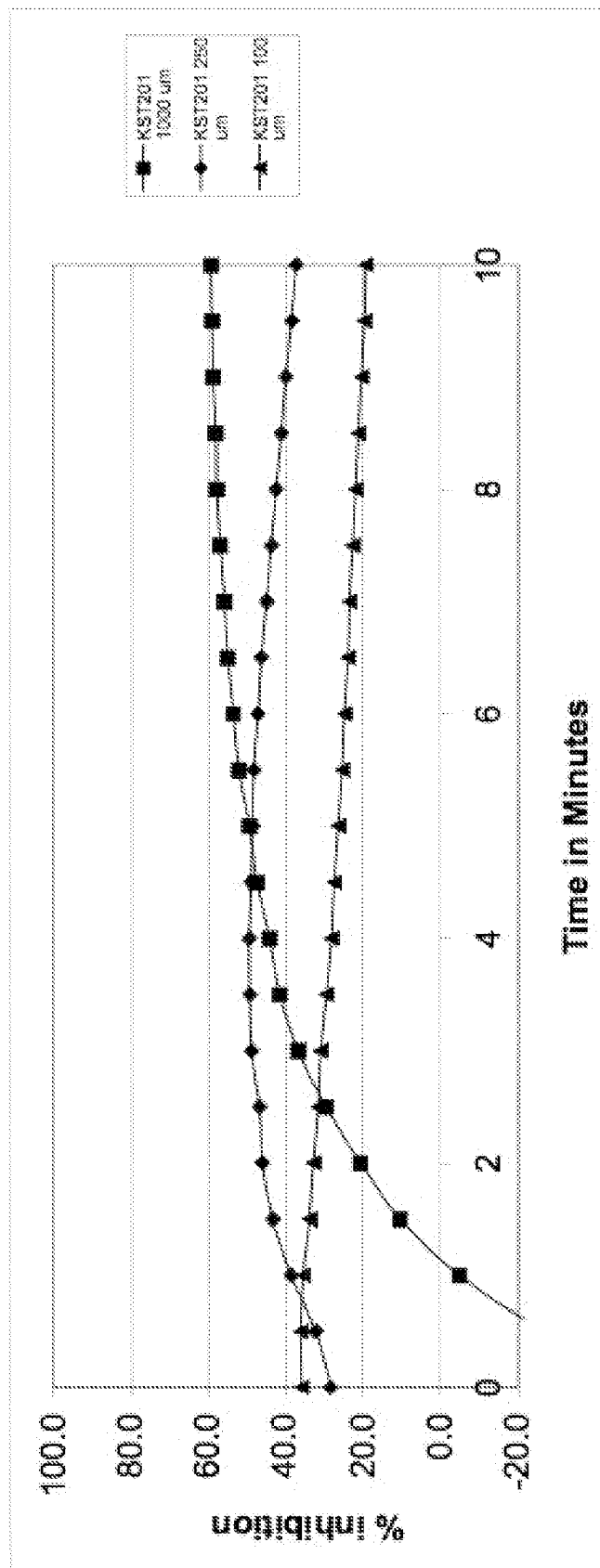
Figure 12C:
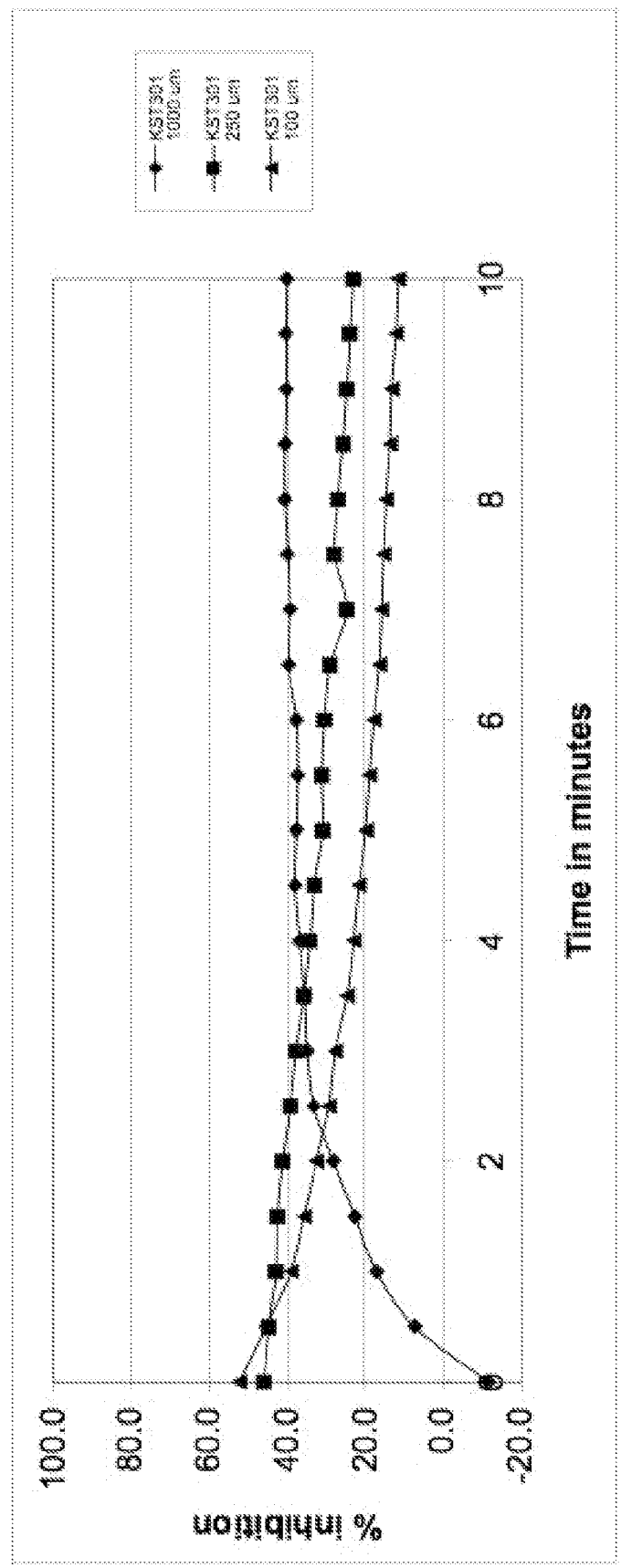
Figure 12D:
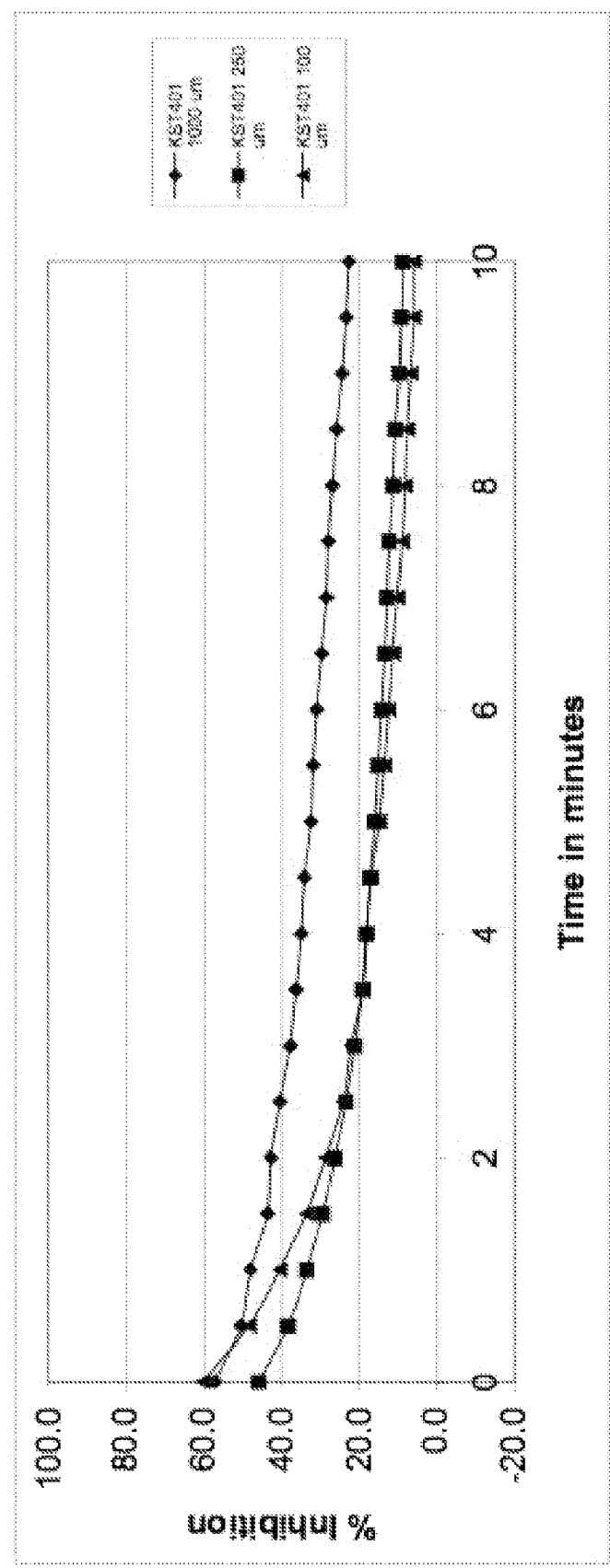

In dose response studies of resveratrol and KST201 on COX1 (FIG. 10) and COX2 (FIG. 11) enzyme activity, doses of 10, 25, 50, 100 and 200 µM of each agent was tested against both COX isomers. As noted, COX activity was quantified by measuring the amount of final product PGF2-α which competed with AChE-linked PGs for binding to an antibody immobilized to microplates. Results represent mean±SD of triplicate determinations.

Resveratrol and KST201 decreased both COX1 and COX2 catalysis of the conversion of the PG precursor to PG. Treatment with concentrations of resveratrol ranging from 10 µM to 200 µM reduced the enzymatic activity of both COX isomers: COX1 was reduced from 5% of initial activity down to complete inhibition; COX2 was reduced from 31% down to 6% of initial activity. KST201 showed less anti-COX activity than did resveratrol, inhibiting the activity of both enzymes by about 50%.

It was concluded that KST-201 and the other hydroxylated tolan compounds disclosed herein will inhibit any biological function that depends upon full COX1 or COX2 activity, and may act preferentially on one or the other isoform. Thus these compounds can be used to treat any disease or condition in which the biochemical pathways that require COX1 or COX2 activity play a pathophysiologic role, including, but not limited to, cancer and the various skin disorders or conditions indicated above.

EXAMPLE V

Anti-Melanoma Activity of Hydroxytolans

Inhibition of Tyrosinase

Meyskens and co-workers (Meyskens, F L et al., 1999, *Clin. Cancer Res.* 5: 1197-1202) showed that the response of redox-sensitive transcription factors NF-κB and AP-1 was different in melanoma cells compared to normal melanocytes because different members of each family of transcription factors were involved and NF-κB was mutated in melanoma. As a consequence, the response to redox stress resulted in further up regulation of these transcription factors in melanoma cells while down regulation occurred in melanocytes. These results demonstrated the importance of the ability of KST-201 to downregulate NF-κB expression. In addition, the melanin in melanoma cells has been shown to behave differently than in melanocytes and become a superoxide generator when it was oxidized (Yang and Meyskens, 2005, *Mol. Pharmacol.* 67:298-308; Yang et al., 2005, supra).

In light of the above, decreasing melanin levels in melanoma cells should lead to a positive outcome in treating melanoma.

Indeed, treatment of human melanocytes with resveratrol led to their depigmentation which is due in part to the direct inhibition of tyrosinase (the rate limiting enzyme in melanin synthesis). Concomitantly with the resveratrol-induced decrease in tyrosinase levels was a profound decrease in dopachrome tautomerase (DCT) protein, another enzyme involved in melanin synthesis. This was accompanied by a corresponding reduction in DCT mRNA. This but also has potential chemotherapeutic implications applications Because decreased DCT levels are associated with increased sensitivity to chemo- and radiotherapy (Newton, et al., 2007), and resveratrol induced decreases in DCT, contributes to its skin depigmentation properties, the present inventor conceived that the tolan compounds designed as analogues of resveratrol would be inhibitors of tyrosinase. This was tested in the studies described below.

Inhibition of Mushroom Tyrosinase Activity

All chemical used for reagents were purchased from Sigma Chemical Company. KST201 at each tested concentration (1000, 250 and 100 µM) was dissolved in 10% ethanol from a master mixture of the drug prepared at 0.1M in 100% ethanol.

Mushroom tyrosinase (Sigma) was diluted in 50 mM phosphate buffer, pH 6.5 to yield a concentration of 16 U/µl. Kojic acid and resveratrol were used as controls for inhibition. A master mix containing 0.5 mM L-DOPA [3,4-dihydroxy-1-phenylalanine], 10 mM Sodium L-tyrosine in 50 mM phosphate buffer, pH 6.5 was prepared. The KST-201 dilutions were preincubated with the enzyme for 20 minutes. The samples were pipetted into 24 well plates and the master mixture added quickly. The reaction was read using a kinetic format in which wells were read every 30 seconds over a course of 10 minutes at a wavelength of 475 nm using a Synergy HT Plate reader. A kinetic curve was generated for each sample compared to a total reaction with mushroom tyrosinase without a drug (total).

The inhibitory effects of resveratrol and hydroxytolan compounds KST-201, K KST-301 and KST-401 on mushroom tyrosinase activity were evaluated and results are shown in FIGS. 12A-12D. These three tolan compounds were active inhibitors. The activity of the other three KST compounds compared to resveratrol is:

KST-201 (59.2±13% inhibition) was about equal to resveratrol (59.9±7.4%)

KST-301 (40.1±9.9%) and KST-401 (22.7±6.5%) were active, though less potent than resveratrol.

In combination with the results shown in Example II above that illustrate the cytotoxic action of hydroxytolans on human melanoma cells, and, additionally, the impact of these compounds in vivo against HSV-1 infection (which, as noted, is manifest at the cellular level, it is concluded that the hydroxytolan compounds and other resveratrol analogs of the present invention are effective anti-tumor and anti-cancer agents for humans.

EXAMPLE VI

Combination of Hydroxytolan (HT01) and Ascorbate (VC) Against Ovarian Cancer Cells Vitamin C (ascorbic acid) was dissolved in culture medium (MEM) as stock solutions of 4 mM VC. KST-201 was dissolved in DMSO as 2 mM stock and was then subsequently diluted in MEM so that the final DMSO concentration in any well was less than 1%.

Human ovarian cancer cells (MDAH 2274) were exposed to VC for 1, 2 or 3 days, and the $CD_{50}$ was evaluated using the MTT assay as in Example II. Results are shown in Table 18. The $CD_{50}$ of VC ranged from 937 µM for 1 day of exposure to 879 µM for 3 days of exposure. Exposure of MDAH 2274 cells to the hydroxytolan for 1, 2 or 3 days, yielded $CD_{50}$ values ranging from 21.5 µM (1 day) to 3.1 µM (3 days).

Finally, when the ascorbate was combined with the hydroxytolan in a ratio of 400:1 (VC to HT), the 1 day $CD_{50}$ values were 466 for VC, 1.16 µM for KST-201, and the 2-day $CD_{50}$ values were 393 µM for VC and 0.98 µM for KST-201 after 3 days.

TABLE 18

Cytotoxicity of Ascorbate and Hydroxytolan against Human Ovarian Cancer Cells (MDAH 2274)

| Incubation Time | $CD_{50}$ (µM) of compounds tested individually | | $CD_{50}$ (µM) of each Compound tested in combination* | |
|---|---|---|---|---|
| In days | Ascorbate | Hydroxytolan | Ascorbate | Hydroxytolan |
| 1 | 937 ± 2.5 | 21.5 ± 7.4 | 466 ± 39.1 | 1.16 ± 0.09 |
| 2 | 900 ± 46.7 | 10.5 ± 2.7 | 389 ± 9.6 | 0.97 ± 0.02 |
| 3 | 879 ± 48.4 | 3.1 ± 0.1 | 393 ± 6.0 | 0.98 ± 0.02 |

*VC: KST-201 ratio in mixture was 400:1

Results of additional experiments demonstrated, the VC:HT combination killed tumor cells within 8 hours of exposure. The $CD_{50}$ values for 1 day of exposure are indicative of the $CD_{50}$ values after 8 hours.

Thus ascorbate alone had a $CD_{50}$ of 937±2.50 µM and hydroxytolan alone had a $CD_{50}$ of 21.5±7.4 µM. When these compounds were combined, the $CD_{50}$ value of VC in the combination decreased to 466±39 µM (i.e., the cytotoxic potency was about doubled) and the $CD_{50}$ value of the HT decreased to 1.16±0.1 µM (i.e., the cytotoxic potency increased about 20-fold.

This shows that the combination of hydroxytolans with ascorbate renders the hydroxytolan surprisingly more active in its ability to kill cancer cells.

EXAMPLE VII

Combination of Hydroxytolan and Ascorbate Against Prostate Cancer Cells

Vitamin C and KST-201 were prepared as above. When KST-201 was combined with VC, the KST-201 concentration was adjusted to yield VC:KST-201 ratios ranging from 100:1 to 500:1. The studies reported below employed a mixture of VC and KST-201 at a VC:KST-201 ratio of 200:1.

After 1 or 2 days of incubation at 37° C. in humidified $CO_2$ in air, the MTT assay was performed to evaluate the number of remaining viable T24 cells in each well. Results are shown in Table 19.

TABLE 19

Cytotoxicity of Ascorbate Hydroxytolan Combination against T24 Human Bladder Cancer Cells

| Incubation Time | $CD_{50}$ (µM) of compounds tested Individually | | $CD_{50}$ (µM) of each Compound tested in combination* | |
|---|---|---|---|---|
| (days) | VC | KST-201 | VC | KST-201 |
| 1 | 849 ± 70.1 | 21.5 ± 7.4 | 638 ± 16 | 3.19 ± 0.08 |
| 2 | 896 ± 59.8 | 10.5 ± 2.7 | 634 ± 55 | 3.17 ± 0.27 |

*VC: KST-201 ratio in mixture was 200:1

The $CD_{50}$ of VC on T24 cells ranged from 849 µM for 1 day of exposure to 896 µM for 2 days of exposure. Exposure T24 cells to KST-201 for 1 or 2 days, yielded $CD_{50}$ values ranging from 21.5 µM (1 day) to 10.5 µM (2 days). When the ascorbate was combined with KST-201 in a ratio of 200:1 (VC to KST-201), the $CD_{50}$ values ranged from 638 for VC and 3.19 µM for KST-201) after 1 day to 634 for VC and 3.17 µM for KST-201 after 2 days.

Thus when the compounds were given together, the cytotoxic potency of VC increased about 1.3-fold and the cytotoxic potency of KST-201 increased as much as about 7-fold).

EXAMPLE VIII

Effects of Hydroxytolan Compounds on Cancer In Vivo

A, Prostate Cancer:

A group of 40 men aged 55-75 suffering from prostate cancer receive a daily dosage of between 10 µg and 5 mg/Kg body weight of KST-201, KST-213, KST-301 or KST-401 (10 patients per compound). Examination of the patients by clinical, radiographic and histopathological tests show significant shrinkage in tumors, and signs of cell death in 38% of the patients; there are no significant differences between the four treatment groups.

B, Bladder Cancer

A group of 20 men and 20 women aged 50-75 with bladder cancer are treated by intravenous injection of between 10 µg and 5 mg/kg of KST-201, KST-213, KST-301 or KST-401. Each compound is given to a group of 5 men and 5 women) over a period of three months. Clinical, radiographic and histopathological tests show significant remission in 35% of patients, accompanied by signs of cell death in 45%. There are no significant differences between the results with the four compounds.

C. Breast Cancer

A group of 40 women with a past history of breast cancer who had been treated by surgery or radiation, or both, and women who had a strong family history of breast cancer are studied. This study investigates whether KST-201, KST-213, KST-301 and KST-401 administered transdermally each day through a skin patch aid in preventing breast cancer or metastatic cancer following cancer therapy. Patches are prepared with a lipophilic carrier which is readily absorbed through the skin (glycerol cold cream containing glycerin and peanut oil). The HT compound is mixed with the lipophilic cream such that each patch comprises 10 mg to 100 mg of active compound. The patch is applied to the skin each day, and rapid absorption occurs. After two hours, the patch is removed. Over a one-year study period, it is observed that this high-risk group does not show any evidence of breast cancer or other metastatic cancer.

D. Ovarian Cancer

A study is carried out in a group of 40 women with ovarian cancer of various grades to determine the effect of treatment with compounds of KST-201, KST-213, KST-301 and KST-401. The administration protocol involves daily administration of a gelatin capsule containing 200 mg of active compound. A significant decrease is observed in the rate of production of relevant ovarian cancer markers (Muc-1 protein determined by immunoassay, sperm protein 17 (Sp17) DNA determined by RT-PCR and Sp17 determined by immunocytochemistry and flow cytometry). Tumors regress or show no further growth during the study period.

E. Colon Cancer

Eight patients suffering from advanced colon cancer are treated daily for three weeks with an intravenous infusion of 2 g of the compounds KST-201, KST-213, KST-301 or KST-401 dissolved in saline. Two patients are assigned to each compound. The compounds are dissolved in sterile saline. Each of the patients' pain and discomfort is significantly reduced, and significant reduction in the cancer marker carcinoembryonic antigen (CEA) is observed. Progression of the tumor is also arrested over the treatment period.

Another eight patients with terminal colon cancer are treated by daily bolus injections (intravenous or intramuscular) of 2 g of KST-201, KST-213, KST-301 or KST-401. Over the period of the study, there is a marked reduction in pain and discomfort, a reduction in circulating levels of CEA, and dissemination of the tumors is diminished.

All references cited herein, including journal articles or abstracts, published or corresponding U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by references.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method of treating bladder cancer, breast cancer, colon cancer, ovarian cancer or prostate cancer in a subject, comprising administering to a subject with bladder cancer, breast cancer, colon cancer, ovarian cancer or prostate cancer in need of such cancer treatment, an effective amount of one or more of the following compounds:

(i) KST-201, the structural formula of which is:

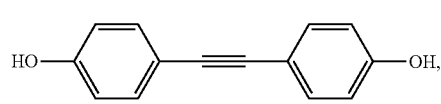

Formula II (ii) KST-213, the structural formula of which is:

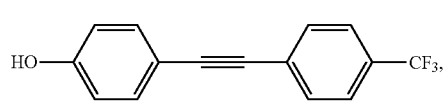

Formula III (iii) KST-301, the structural formula of which is:

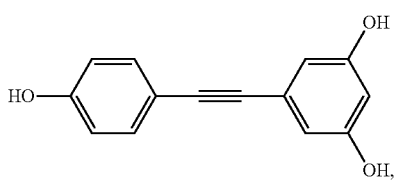

Formula IV or
(iv) KST-401, the structural formula of which is:

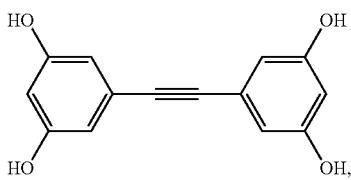

Formula V thereby treating said cancer.

2. The method of claim 1 wherein the one or more compounds is administered orally, intravenously, intraperitoneally, topically, intrathecally, intramuscularly, subcutaneously, transdermally, intranasally or rectally.

3. The method of claim 1, wherein the cancer is one that developed from a precancerous lesion.

4. A method of treating melanoma in a subject, comprising administering to a subject with melanoma in need of such melanoma treatment, an effective amount of KST-201, the structural formula of which is:

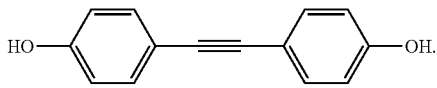

Formula II

5. The method of claim 4, wherein the melanoma developed from a precancerous lesion.

6. The method of claim 5, wherein the melanoma developed from actinic keratosis.

7. The method of claim 4 wherein the KST-201 is administered orally, intravenously, intraperitoneally, topically, intrathecally, intramuscularly, subcutaneously, transdermally, intranasally or rectally.

* * * * *